(12) United States Patent
Anderson et al.

(10) Patent No.: US 7,381,560 B2
(45) Date of Patent: Jun. 3, 2008

(54) EXPRESSION AND USE OF ANTI-CD20 ANTIBODIES

(75) Inventors: Darrell R. Anderson, Escondido, CA (US); Nabil Hanna, Rancho Santa Fe, CA (US); Roland A. Newman, San Diego, CA (US); Mitchell E. Reff, San Diego, CA (US); William H. Rastetter, Rancho Santa Fe, CA (US)

(73) Assignee: Biogen Idec Inc., Cambridge, MA (US)

( * ) Notice: Subject to any disclaimer, the term of this patent is extended or adjusted under 35 U.S.C. 154(b) by 1409 days.

(21) Appl. No.: 09/911,692

(22) Filed: Jul. 25, 2001

(65) Prior Publication Data

US 2003/0095963 A1 May 22, 2003

Related U.S. Application Data

(60) Continuation of application No. 08/475,813, filed on Jun. 7, 1995, now Pat. No. 6,682,734, which is a division of application No. 08/149,099, filed on Nov. 3, 1993, now Pat. No. 5,736,137, which is a continuation-in-part of application No. 07/978,891, filed on Nov. 13, 1992, now abandoned.

(51) Int. Cl.
*C12N 5/10* (2006.01)
*C12N 15/00* (2006.01)
*C12P 21/08* (2006.01)

(52) U.S. Cl. ............... 435/328; 435/358; 435/361; 435/353; 435/334; 435/343.1; 435/344; 435/326; 435/344.1; 435/69.1; 435/69.6

(58) Field of Classification Search .......... 435/326, 435/358, 361, 353, 328, 334, 343.1, 344, 435/344.1, 69.1, 69.6
See application file for complete search history.

(56) References Cited

U.S. PATENT DOCUMENTS

| | | | |
|---|---|---|---|
| 4,831,175 A | 5/1989 | Gansow | |
| 4,975,278 A | 12/1990 | Senter et al. | |
| 5,099,069 A | 3/1992 | Gansow | |
| 5,124,471 A | 6/1992 | Gansow | |
| 5,246,692 A | 9/1993 | Gansow | |
| 5,286,850 A | 2/1994 | Gansow | |
| 5,439,665 A | 8/1995 | Hansen | |
| 5,460,785 A | 10/1995 | Rhodes | |
| 5,500,362 A | 3/1996 | Robinson et al. | 435/7.23 |
| 5,595,721 A | 1/1997 | Kaminski | |
| 5,648,267 A | 7/1997 | Reff | 435/320.1 |
| 5,677,180 A | 10/1997 | Robinson et al. | |
| 5,686,072 A | 11/1997 | Uhr et al. | |
| 5,693,780 A | 12/1997 | Newman et al. | |
| 5,721,108 A | 2/1998 | Robinson et al. | |
| 5,736,137 A | 4/1998 | Anderson | |
| 5,776,456 A | 7/1998 | Anderson | |
| 5,843,398 A | 12/1998 | Kaminski et al. | |
| 5,843,439 A | 12/1998 | Anderson | |
| 6,015,542 A | 1/2000 | Kaminski et al. | |
| 6,090,365 A | 7/2000 | Kaminski et al. | |
| 6,120,767 A | 9/2000 | Robinson et al. | |
| 6,183,744 B1 | 2/2001 | Goldenberg | |
| 6,287,537 B1 | 9/2001 | Kaminski et al. | |
| 6,306,393 B1 | 10/2001 | Goldenberg | |
| 6,399,061 B1 | 6/2002 | Anderson | |
| RE38,008 E | 2/2003 | Abrams | |
| 6,565,827 B1 | 5/2003 | Kaminski et al. | |
| 6,652,852 B1 | 11/2003 | Robinson et al. | |
| 6,682,734 B1 | 1/2004 | Anderson | |
| 6,893,625 B1 | 5/2005 | Robinson et al. | |
| 2002/0009444 A1 | 1/2002 | Grillo-Lopez | |
| 2002/0197255 A1 | 12/2002 | Anderson et al. | |
| 2003/0021781 A1 | 1/2003 | Anderson et al. | |
| 2003/0026804 A1 | 2/2003 | Grillo-Lopez | |
| 2003/0082172 A1 | 5/2003 | Anderson et al. | |
| 2003/0095963 A1 | 5/2003 | Anderson | |
| 2003/0147885 A1 | 8/2003 | Anderson et al. | |
| 2003/0206903 A1 | 11/2003 | Grillo-Lopez | |
| 2004/0167319 A1 | 8/2004 | Teeling | |
| 2004/0213784 A1 | 10/2004 | Grilo-Lopez et al. | |
| 2005/0163708 A1 | 7/2005 | Robinson et al. | |

(Continued)

FOREIGN PATENT DOCUMENTS

EP 0 125 023 A1 11/1984

(Continued)

OTHER PUBLICATIONS

Lowman, H.B. Slides presented at IBC Antibody Engineering Conference, Dec. 2, 2003. Differential Activities in a Series of Humanized Anti-CD20 Antibodies.

Polyak, M.J., et al. (2002) *Blood* 99: 3256-62. Alanine-170 and proline-172 are critical determinants for extracellular CD20 epitopes; heterogeneity in the fine specificity of CD20 monoclonal antibodies is defined by additional requirements imposed by both amino acid sequence and quaternary structure.

Chinn, et al. "Production and characterization of radiolabeled anti-CD20 monoclonal antibody: potential application to treatment of B-cell lymphoma." Proceedings of the American Medical Association for Cancer Research, vol. 33, Abstract 2012, p. 337, 1992.

Classon, et al. "The Primary Structure of the Human Leukocyte Antigen CD37, A Species Homologue of the Rat MRC OC-44 Antigen." The Journal of Experimental Medicine, vol. 169, No. 4, pp. 1497-1502, 1989.

(Continued)

*Primary Examiner*—Ronald Schwadron
(74) *Attorney, Agent, or Firm*—Sidley Austin LLP

(57) ABSTRACT

Disclosed are immunologically active antibodies directed against the CD20 antigen, as well as host cells comprising nucleic acid sequences encoding the light chains and heavy chains of immunologically active antibodies wherein the cell is capable of expressing and secreting an immunologically active chimeric anti-CD20 antibody and methods of using such host cells to make purified antibodies. The antibodies are useful for treating and diagnosing B cell disorders.

10 Claims, 21 Drawing Sheets

U.S. PATENT DOCUMENTS

| | | |
|---|---|---|
| 2005/0186205 A1 | 8/2005 | Anderson et al. |
| 2006/0034835 A1 | 2/2006 | Adams |

FOREIGN PATENT DOCUMENTS

| | | |
|---|---|---|
| EP | 0 125 023 B1 | 11/1984 |
| EP | 0 173 494 A2 | 3/1986 |
| EP | 0 274 394 A2 | 7/1988 |
| EP | 0 274 394 A3 | 7/1988 |
| EP | 0 682 040 A1 | 11/1995 |
| EP | 0 682 040 B1 | 11/1995 |
| EP | 0 451 216 B1 | 1/1996 |
| EP | 0 669 836 B1 | 3/1996 |
| EP | 0 752 248 A1 | 1/1997 |
| EP | 0 125 023 B2 | 3/2002 |
| WO | 87/02671 A1 | 5/1987 |
| WO | WO 88/04936 | 7/1988 |
| WO | 89/00999 A1 | 2/1989 |
| WO | WO 91/04320 | 4/1991 |
| WO | WO 92/07466 | 5/1992 |
| WO | 93/02108 A1 | 2/1993 |
| WO | WO 93/02180 | 2/1993 |
| WO | WO 94/11026 | 5/1994 |
| WO | 00/27428 A1 | 5/2000 |
| WO | 00/27433 A1 | 5/2000 |
| WO | 01/10460 A1 | 2/2001 |
| WO | 2004/056312 | 7/2004 |

OTHER PUBLICATIONS

DeNardo, et al. "Requirements for a Treatment Plan in System for Radioimmunotherapy." International Journal of Radiation Oncology Biology Physics, vol. 11, No. 2, pp. 335-348, 1985.

Kaminski, et al. "Radioimmunotherapy (RIT) of Refractory B-Cell Lymphoma with 131-I-Anti-B1 (Anti-CD20) Antibody: Promising Early Results Using Non-Marrow Ablative Radiation Doses." Blood, Abstract 161, p. 162.

Langmuir, "Radiommunotherapy: Clinical Results and Dosimetric Considerations." Nuclear Medicine and Biology, Vol. 19, No. 2, pp. 213-225. 1992.

Larson, et al. "Comparison of Bone Marrow Dosimetry and Toxic Effect of High Dose $^{131}$I-labeled Monoclonal Antibodies Administered to Man." Nuclear Medicine and Biology, vol. 16, No. 2, pp. 153-158, 1989.

Leichner, et al. "Tumor dosimetry in radioimmunotherapy: Methods of calculation for beta particles." Medical Physics, vol. 20, No. 2, Pt.2, pp. 529-534, 1993.

Leichner, et al. "Dosimetry and Treatment Planning in Radioimmunotherapy." Frontiers of Radiation Therapy and Oncology, vol. 24, pp. 109-120, 1990.

Link, et al. "A Unique Antigen on Mature B-Cells Defined by a Monoclonal Antibody." The Journal of Immunology, vol. 137, No. 9, pp. 3013-3018, 1986.

Macey, et al. "A Treatment Planning Program for Radioimmunotherapy" Frontiers of Radiation Therapy and Oncology, vol. 24, pp. 123-131, 1990.

Meredith, et al. "Dose Fractionation of Radiolabeled Antibodies in Patients with Metastatic Colon Cancer." Journal of Nuclear Medicine, vol. 33, No. 9, pp. 1648-1653, 1992.

Parker, et al. "Radioimmunotherapy of Human B-Cell Lymphoma with $^{90}$Y-conjugated Antiidiotype Monoclonal Antibody." Cancer Research, vol. 50, No. 3, pp. 1022s-1028s, 1990.

Pearson, et al. "Enchanced Therapeutic Efficacy of an Immunotoxin in combination with Chemotherapy against an Intraperitoneal Human Tumor Xenograft in Athymic Mice." Cancer Research vol. 49, No. 18, pp. 4990-4995, 1989.

Press, et al. "Endocytosis and Degradation of Monoclonal of Antibodies Targeting Human B-Cell Malignancies" Cancer Research, vol. 49, No. 17, pp. 4906-4912, 1989.

Press, et al. "Radiolabeled Antibody Therapy of Human B Cell Lymphomas." Immunobiology of Proteins and Peptides VI, vol. 303, pp. 91-96, 1991.

Securities and Exchange Commission, Form S-1 Registration Statement, Filed 1991, IDEC Pharmaceuticals.

Senter, Peter D. "Activation of prodrugs by antibody-enzyme conjugates: a new approach to cancer therapy." The FASEB Journal, vol. 4. pp. 188-193, 1990.

Senter, et al. "Activation of Prodrugs by Antibody-Enzyme Conjugates" Immunobiology of Proteins and Peptides VI, vol. 303, pp. 97-105, 1991.

Schwartz-Albiez, et al. "The B Cell-Associated CD37 Antigen (gp40-52) Structure and Subcellular Expression of an Extensively Glycosylated Glycoprotein." The Journal of Immunology, vol. 140, No. 3, pp. 905-914, 1988.

Sharkey, et al. "Biological Considerations for Radioimmunotherapy." Cancer Research, vol. 50, No. 3, pp. 964s-969s, pp. 1990.

Stewart, et al. "Intraperitoneal $^{131}$I- And $^{90}$Y-Labelled Monoclonal Antibodies for Ovarian Cancer: Pharmacokinetics and Normal Tissue Dosimetry." International Journal of Cancer, Supplement 3, pp. 71-76, 1988.

Uckun, et al. "Combined Ex Vivo Treatment with Immunotoxins and Mafosfamid: A Novel Immunochemotherapeutic Approach for Elimination of Neoplastic T Cells from Autologous Marrow Grafts." The Journal of Immunology, vol. 134, No. 5, pp. 3504-3515, 1985.

Uckun, et al. "Increased Efficiency in Selective Elimination of Leukemia Cells by a Combination of a Stable Derivative of Cyclophosphamide and a Human B-Cell-specific Immunotoxin Containing Pokeweed Antiviral Protein." Cancer Research , vol. 45, No. 1, pp. 69-75, 1985.

Yokota, et al. "Synergistic Potentiation of in Vivo Antitumor Activity of Anti-Human T-Leukemia Immunotoxins by Recombinant α-Interferon and Daunorubicin." Cancer Research, vol. 50, No. 1, pp. 32-37, 1990.

Badger, et al. "Experimental Radioimmunotherapy of Murine Lymphoma with 131 I-labeled Anti-T-Cell Antibodies." Cancer Research, 46, pp. 6223-6228, 1986.

Buchsbaum, et al. "Improved Delivery of Radiolabeled Anti-B1 Monoclonal Antibody to Raji Lymphoma Xenografts by Predosing with Unlabeled Anti-B1 Monoclonal Antibody." Cancer Research; 52, pp. 637-642, 1992.

Chen, et al. "Tumor Idiotype Vaccines. VI. Synergistic Anti-Tumor Effects with Combined "Internal Image" Anti-Idiotypes and Chemotherapy." Journal of Immunology, 143, pp. 1053-1057, No. 3, 1989.

Clark et al. "Role of the Bp35 cell surface polypeptide in human B-cell activation" vol. 82; pp. 1776-1770, 1985.

Clark, et al. "Phase I Evaluation of the Anti-Bp35 Antibody Induces Human B Cell Proliferation: Implications for In Vivo Immunotherapy." Journal Cellular Biochemistry Supp. 9A, p. 63, 1985.

DeNardo, et al. "Fractionated Radioimmunotherapy of B-Cell Malignancies with 131I-Lym-$^1$." Cancer Research (Suppl.) 50, pp. 1014s-1016s, 1990.

Kaminski, et al. "Initial Clinical Radioimmunotherapy Result with $^{131}$-I-Anti-B1 (Anti-CD20) in Refractory B-Cell Lymphoma." Antibody Immunoconjugates, and Radiopharmaceuticals vol. 5, No. 3 p. 345, 1992.

Kaminski, et al. "131-I Anti-B1: Initial Clinical Evaluation in B-Cell Lymphoma." Third Conference on Rid and Rit of Cancer, Abstract. No. 144, 1990.

Langmuir, "Radioimmunotherapy: Clinical Results and Dosimetric Considerations." Nuclear Medicine Biology vol. 19, No. 2, pp. 213-225, 1992.

Levy, et al. "Tumor Therapy with Monoclonal Antibodies." Federation Proceedings 42:9 pp. 2650-2656, 1983.

Macklis, et al. "Radiobiologic Sutdies of Low-Dose-Rate $^{90}$Y-Lymphoma Therapy." Cancer Supplement, vol. 73, No. 3, pp. 966-973, 1994.

Maloney, et al. "The Anti-Tumor effect of Monoclonal Anti-CD20 Antibody mAB) Therapy Includes Direct Anti-Proliferative Activity and Production of Apoptosis in CD20 Positive Non-Hodgkin's Lymphoma (NHL) Cell Lines." Interferon and Chronic Myleogenous Leukemia. Fred Hutchinson Cancer Research & University of Washington, 637a, p. 2535.

Maloney, et al. "Monoclonal Anti-Idiotype Antibody Therapy of B-Cell Lymphoma: The Addition of a Short Course of Chemotherapy Does Not Interfere with the Antitumor Effect Nor Prevent the Emergence of Idiotype-Negative Variant Cells." Blood, vol. 80, No. 6, pp. 1502-1510, 1992.

Masucci, et al. "Chemotherapy and Immunotherapy of Colorectal Cancer." Medical Oncology Tumor Pharmacother vol. 8, No. 3, pp. 207-220, 1991.

Nadler, et al. "A Unique Cell Surface Antigen Identifying Lymphoid Malignancies of B Cell Origin." Journal of Clinical Investigative, vol. 67, pp. 134-140, 1981.

Reilly, "Radioimmunotherapy of malignancies." Clinical Pharmacy, vol. 10, pp. 359-375, 1991.

Press, et al. Scientific Proceedings, ASCO, Abstract No. 864, 1986.

See-Lasley, et al. "Hodgkin's Disease and Non-Hodgkin's Lymphoma Nitrogen mustard, vincristine (Oncovin), procarbazine, and prednisone (MOPP)." Manual of Oncology Therapeutics, C.V. Mosby Company, pp. 44-71, 1981.

Senter, et al. "Enhancement of the in vitro and in vivo Antitumor Activities of Phosphorylated Mitomycin C and Etoposide Derivatives by Monoclonal Antibody-Alkaline Phosphatase Conjugates." Cancer Research 49, pp. 5789-5792, 1989.

Stashenko, et al. "Characterization of Human B Lymphocyte-Specific Antigen." The Journal of Immunology vol. 125, No. 4, pp. 1678-1685, 1960.

*Idec Pharmaceuticals v. Corixa Corp.*, Case No. 01-1637-IEG (S.D. Cal. Oct. 14, 2003).

*Biogen Idec v. Corixa Corp.*, Case No. 01-1637-IEG (S.D. Cal. Jan. 22, 2004).

Grossbard M.L., et al., "Monoclonal antibody-based therapies of leukemia and lymphoma," *Blood*, 1992, 80:863-878.

Tedder T.F., et al., "Antibodies reactive with the B1 molecule inhibit cell cycle progression but not activation of human B lymphocytes," *Eur J Immunol*, 1986, 16(8):881-87.

Tedder T.F., et al., "Cloning of a complementary DNA encoding a new mouse B lymphocyte differentiation antigen, homologous to the human B1 (CD20) antigen, and localization of the gene to chromosome 19," *J Immunol*, 1988, 141(12):4388-94.

Kaminski, et al., "Radioimmunotherapy of Advanced B-Cell Lymphoma with Non Bone Marrow Ablative Doses of 131-I MB-1 Antibody," 1990, *Antibody Immunoconjugates, and Radiopharmaceuticals*, vol. 3, No. 1, Abstract No. 83.

Kaminski, et al., "Radioimmunodetection (RID) and Non Marrow Ablative Radioimmunotherapy (RIT) of B-Cell Lymphoma With 131-I MB-1 Antibody," 1990, *Proceedings of ASCO*, vol. 9, Abstract No. 1051.

Wahl, et al., "Radioimmunotherapy of B-Cell Lymphoma with I131 MB-1 Monoclonal Antibody," *The Journal of Nuclear Medicine: Proceedings of the 37th Annual Meeting*, p. 852, Abstract No. 622.

Kaminski, et al., "Phase I Trial Results of 131-I MB-1 Antibody Radioimmunotherapy (RAIT) of B-Cell Lymphoma," 1990, *Antibody Immunoconjugates, and Radiopharmaceuticals*, vol. 4, No. 1, p. 36, Abstract No. 66.

Kaminski, et al., "Phase I Evaluation of 131-I MB-1 Antibody Radioimmunotherapy (RIT) of B-Cell Lymphoma," 1990, *Blood*, vol. 76, No. 10, p. 355a, Abstract No. 1409.

Kaminski, et al., "Imaging, Dosimetry, and Radioimmunotherapy With Iodine 131-Labeled Anti-CD37 Antibody in B-Cell Lymphoma," 1992, *Journal of Clinical Oncology*, vol. 10, No. 11, pp. 1696-1711.

Adams, R.A. et al., Direct implantation and serial transplantation of human acute lymphoblastic leukemia in hamsters, SB-2, Can Res 28:1121-1125 (1968).

Adams, Richard, Formal Discussion: The role of transplantation in the experimental investigation of human leukemia and lymphoma, *Can. Res. 27*:2479-2482 (1967).

Anderson, K.C., et al., Hematologic engraftment and immune reconstitution posttransplantation with anti-B1 purged autologous bone marrow, Blood 69(2):597-604 (1987).

Anderson, D.R., et al., Immunoreactivity and effector function associated with a chimeric anti-CD20 antibody, The Second Annual IBC International Conference on Antibody Engineering, Dec. 16-18, 1991.

Anderson, K.C., et al., Expression of human B cell-associated antigens on leukemias and lymphomas: A model of human B cell differentiation, Blood 63(6):1424-1433 (1984).

Appelbaum, F.R., Radiolabeled Monoclonal Antibodies in the Treatment of Non-Hodgkin's Lymphoma. *Hem. Onc. Clinics of N.A.* 5(5):1013-1025 (1991).

Armitage, J.O. et al., Pr dicting therapeutic outcome in patients with diffus histiocytic lymphoma treated with cyclophosphamide, adriamycin, vincristin and prednisone (CHOP), *Cancer 50*:1695 (1982).

Bhan, A.K., et al., Stages of B cell differentiation in human lymphoid tissue, J. Exp. Med., 154:737-749 (1981).

Boulianne, G.L. et al., Production of functional chimaeric mouse/human antibody, *Nature* 312:643 (Dec. 1984).

Brunner, K.T. et al., Quantitative assay of the lytic action of immune lymphoid cells on $^{51}$Cr-labeled allogeneic target cells in vitro; inhibition by isoantibody and drugs, *Immunology 14*:181-189 (1968).

Buchsbaum, D.J., et al., A comparison of $^{131}$I-labeled monoclonal antibody 17-1A treatment to external beam irradiation on th growth of LS174T human colon cardinoma xenografts, Int. J. Radiation Oncology Biol. Phys., 18:1033-1041 (1990).

Buchsbaum, D.J., et al., Comparative binding and preclinical localization and therapy studies with radiolabeled human chimeric and murine 17-1A monoclonal antibodies, Cancer Research (Suppl.) 50:993s-999s (1990).

Buchsbaum, D.J., et al., Comparison of $^{131}$I- and $^{90}$Y-labeled monoclonal antibody 17-1A for treatment of human colon cancer xenografts, Int. J. Radiation Oncology Biol. Phys. 25:629-638 (1993).

Calvert, J.E., et al., Cellular events in the differentiation of antibody-secreting cells, Seminars in Hematology, 21(4):226-243 (1984).

Chomczynski, P. et al., Single step method of RNA isolation by acid guanidinium thiocyanate-phenol-chloroform extraction, *Anal. Biochem. 162*:156-159 (1987).

Clark, E.A., et al., Role of the Bp35 cell surface polypeptide in human B-cell activation, Proc. Natl. Acad. Sci. USA, 82:1766-1770 (1985).

Cope, Antibody shows promise in treating B-cell lymphoma, Oncology, 8(4):100 (1994).

DeNardo, S.J., et al., Pilot studies of radioimmunotherapy of B cell lymphoma and leukemia using I-131 Lym-1 monoclonal antibody, Antibody, Immunoconjugates, and Radiopharmaceuticals, 1(1):17-33 (1988).

DeNardo, S.J., et al., The biologic window for chimeric L6 radioimmunotherapy, Cancer 73(3):1023-32 (1994).

Dickson, Scientists produce chimeric monoclonal abs, *Genetic Engineering News 5/3* (Mar. 1985).

Eary, J.F. et al, Imaging and Treatment of B-Cell Lymphoma, *J. Nuc. Med. 31/8*:1257-1268 (1990).

Einfeld, D.A. et al., Molecular cloning of the human B cell CD20 receptor predicts a hydrophobic protein with multiple transmembrane domains, *EMBO 7*:711 (1988).

Golay, J.T., et al., The CD20 (Bp35) antigen is involved in activation of B cells from the $G_0$ to the $G_1$ phase of the cell cycle, J. Immunology 135(6):3795-3801 (1985).

Goldenberg, D.M. et al., Targeting, dosimetry and radioimmunotherapy of B-Cell lymphomas with iodine-131-labeled LL2 monoclonal antibody, *J. Clin. Onc. 9/4*:548-564 (1991).

Greenberger, J.S., et al., Effects of monoclonal antibody and complement treatment of human marrow on hematopoiesis in continuous bone marrow culture, Cancer Research 45:758-767 (1985).

Hekman, A., et al., Immunotherapy, The Netherlands Cancer Institute Amsterdam Annual Report, pp. 47-48 (1993).

Lipton, J.M., et al., Distribution of B1, calla, β2 microglobulin and 1a on hematopoietic progenitors and hematopoiesis supporting cells (HSC) in short and long-term cultures, Blood, 60(5) (Suppl. 1):170a (Abstract 609) (1982).

Kaminski, M.G. et al., Radioimmunotherapy of B-cell lymphoma with [$^{131}$I] anti-B1 (anti-CD20) antibody, *NEJM 329/7* (1993).

Liu, A.Y. et al., Production of a Mouse-Human Chimeric Monoclonal Antibody to CD20 with Potent Fc-Dependent Biologic Activity. *J. Immun. 139/10*:3521-3526 (1987).

Marx, Antibodies made to order, *Science 229* 455 (Aug. 1985).

Morrison, S.L. et al., Chimeric human antibody molecules: Mouse antigen-binding domains with human constant region domains, *PNAS 81*:6851-6854 (Nov. 1984).

Morrison, Transfectomas provide novel chimeric antibodies, *Science 229*:1202-1207 (Sep. 1985).

Munro, Uses of chimaeric antibodies, *Nature 312*:597 (Dec. 1984).

Nadler, L.M., et al., B cell origin of non-T cell acute lymphoblastic leukemia a model for discrete stages of neoplastic and normal pre-B cel differentiation, J. Clin. Invest. 74:332-340 (1984).

Nadler, L.M., et al., Anti-B1 monoclonal antibody and complement treatment in autologous bone-marrow transplantation for relapsed B-cell non-Hodgkin's lymphoma, The Lancet, vol. II, pp. 427-431 (1984).

Nadler, L.M., et al., Serotherapy of a patient with a monoclonal antibody directed against a human lymphoma-associated antigen, Cancer Research, 40:3147-3154 (1980).

Neuberger, M.S. et al., A hapten-specific chimaeric IgE antibody with human physiological effector function, *Nature 314*:268 (Mar. 1985).

Oettgen, H.C., et al., Further bioch mical studies of the human B-cell differentiation antigens B1 and B2, Hybridoma, 2(1):17-28 (1983).

Ozato, K., et al., Monoclonal antibodies to mouse MHC antigens III. Hybridoma antibodies reacting to antigens to the H-2$^b$ haplotype reveal genetic control of isotype expression, J. Immunology, 126(1):317-321 (1981).

Press et al., Monoclonal antibody 1F5 (Anti-CD20) serotherapy of human B cell lymphomas, *Blood 69*(2):584-591 (1987).

Press, O.W. et al., "Radiolabeled-antibody therapy of B-cell lymphoma with autologous bone marrow support." *New England Journal of Medicine 329/17*: 1219-12223 (1993).

Press, O.W. et al., Treatment of refractory non-Hodgkin's lymphoma with radiolabeled MB-1 (anti-CD37) antibody, *J. Clin. Onc. 7/8*:1027-1038 (1989).

Reff, M., et al., Depletion of a B cells in vivo by a chimeric mouse human comoclonal antibody to CD20, J. Cellular Biochem., Suppl. 17E:260 (Abstract T103) (1993).

Reff, M., et al., Depletion of B cells in vivo by a chimeric mouse human monoclonal antibody to CD20, Blood, 83(2):435-445 (1994).

Robertson, M.J., et al., Human bone marrow depleted of CD33-positive cells mediates delayed but durable reconstitution of hematopoiesis: Clinical trial of MY9 monoclonal antibody-purged autografts for the treatment of acute myeloid leukemia, Blood, 79(9):2229-2236 (1992).

Robinson, R.D. et al., "Chimeric mouse-human anti-carcinoma antibodies that mediate different anti-tumor cell biological activities," *Hum. Antibod. Hybridomas 2*:84-93 (1991).

Sahagan et al., A genetically engineered murine/human chimeric antibody retains specificity for human tumor-associated antigen, *J. Immunol. 137*:1066-1074 (1986).

Scharff, M., The synthesis, assembly, and secretion of immunoglobulin: A biochemical and genetic approach, *Harvey Lectures 69*:125-143 (1974).

Schlom J., et al., Advantage of dose fractionation in monoclonal antibody-targeted radioimmunotherapy, J. Natl. Cancer Inst., 82(9):763-771 (1990).

Shulman, M. et al., A better cell line for making hybridomas secreting specific antibodies, *Nature 276*:269 (1978).

Smeland, E.B., et al., Activation of human B cells: Alternate options for initial triggering and effects of nonmitogenic concentrations of anti-IgM antibodies on resting and activated cells, J. Immunology, 138(10):3179-3184 (1987).

Srivastava, S.C., et al., Progress in research on ligands, nuclides and techniques for labeling monoclonal antibodies, *Nucl. Med. Bio. 18*(6): 589-603 (1991).

Sun, L.K. et al., Chimeric antibodies with 17-1A-derived variable and human constant regions, *Hybridoma 5/1*:517 (1986).

Tan et al., A human-mouse chimeric immunoglobulin gene with a human variable region is expressed in mouse myeloma cells, *J. Immunol. 135*:8564 (Nov. 1985).

Tedder, T.F., et al., The B cell surface molecule B1 is functionally linked with B cell activation and differentiation, J. Immunology, 135(2):973-979 (1985).

Urlaub, G. et al., Effect of gamma rays at the dihydrofolate reductase locus: deletions and inversions. *Som. Cell & Mol. Gen. 12/6*:555-566 (1986).

Valentine, M.A. et al., Phosphorylation of the CD20 phosphoprotein in resting B lymphocytes, *J. Biol. Chem.* 264(19):11282-11287 (1989).

Wessels, B.W., et al., Radionuclide selection and model absorbed dose calculations for radiolabeled tumor associated antibodies, Med. Phys., 11(5):638-645 (1984).

Anderson D.R. et al. *Biochem. Soc. Trans.* 25(2): 705-08, 1997. Targeted anti-cancer therapy using rituximab, a chimaeric anti-CD20 antibody (IDEC-C2B8) in the treatment of non-Hodgkin's B-cell lymphoma.

Armitage J.O. et al. *J. Clin. Oncol.* 16(8): 2780-95, 1998. New approach to classifying non-Hodgkin's lymphomas: clinical features of the major histologic subtypes. Non-Hodgkin's Lymphoma Classification Project.

Berinstein N.L. et al. *Ann. Oncol.* 9:995-1001, 1998. Association of serum rituximab (IDEC-C2B8) concentration and anti-tumor response in the treatment of recurrent low-grade or follicular non-Hodgkin's lymphoma.

Beychok S. (in) *Cells of Immunoglobulin Synthesis*, B. Pernis et al., eds. New York: Academic Press, 1979, 69-88. Comparative aspects of in vitro and cellular assembly of immunoglobulins.

Buchsbaum D.J. et al. *Cancer Res.* 52: 637-642, 1992. Improved delivery of radiolabeled anti-B1 monoclonal antibody to Raji lymphoma xenografts by predosing with unlabeled anti-B1 monoclonal antibody.

Carrasquillo J.A. et al. *J. Nucl. Med.* 26: 67, abst. No. 276, 1985. Improved imaging of metastatic melanoma with high dose 9.2.27 In-111 monoclonal antibody.

Chinn P.C. et al. *Int. J. Oncol.* 15(5): 1017-25, Nov. 1999. Preclinical evaluation of 90Y-labeled anti-CD20 monoclonal antibody for treatment of non-Hodgkin's lymphoma.

Chinn P.C. et al. *Proc. Ann. Mtg. Am Assn. Cancer Res.* 40: 574, abst. No. 3786, 1999. A $^{90}$Y-labeled anti-CD20 monoclonal antibody conjugated to MX-DTPA, a high-affinity chelator for yttrium.

Cogliatti S.B. et al. *Sw. Med. Weekly* 192: 607-17, 2002. Who is *WHO* and what was *Real*?

Davis T.A. et al. *Clin. Cancer Res.* 5(3): 611-15, 1999. Therapy of B-cell lymphoma with anti-CD20 antibodies can result in the loss of CD20 antigen expression.

Davis T.A. et al. *Proc. Ann. Mtg. Amer. Assn. Cancer Res.* 39: 435, abst. No. 2964, 1998. Therapy of B cell lymphoma with anti-CD20 can result in relapse with loss of CD20 expression.

Dillman R.O. *J. Clin. Oncol.* 12(7): 1497-1515, 1994. Antibodies as cytotoxic therapy.

Grillo-López A.J. IBC Int'l. Conference on Antibody Engineering, La Jolla, Dec. 1994. IDEC-C2B8 chimeric antibody and IDEC-Y2B8 radiolabeled antibody phase I and II studies in patients with non-Hodgkin's lymphoma (abstract of presentation).

Grillo-López A.J. et al. *Ann. Oncol.* 7(3 Suppl.): 57, abst. No. 195, 1996. Treatment (rx) of relapsed non-Hodgkin's lymphoma (NHL) using the 90-yttrium (90-Y) labeled anti-CD20 monoclonal antibody (MAB) IDEC-Y2B8: a phase I clinical trial (PI CT).

Grillo-López A.J. et al. *Antibody Immunoconj. Radiopharm.* 8: 60, abst. No. 10, 1995. Treatment options for patients with relapsed low-grade or follicular lymphoma: the role of IDEC-C2B8.

Grillo-López A.J. et al. *Blood* (86(10 Suppl. 1): 55a, abst. No. 207, 1995. Phase I study of IDEC-Y2B8: 90-yttrium labeled anti-CD20 monoclonal antibody therapy of relapsed non-Hodgkin's lymphoma.

Grillo-López A.J. et al. *Br. J. Haematol.* 93(Suppl. 2): 283, abst. No. 1072, 1996. IDEC-C2B8 chimeric anti-CD20 antibody (MAB):

safety and clinical activity in the treatment of patients (PTS) with relapsed low-grade or follicular (IWF:A-D) non-Hodgkin's lymphoma (NHL).

Horning S.J. et al. *Blood* 100(11 part 1): 357a, abst. No. 1385, 2002. Rituximab treatment failures: tositumomab and Iodine I 131 tositumomab (Bexxar®) can produce meaningful durable responses.

IDEC Pharmaceuticals Corp. and Genentech, Inc., Product insert for Rituxan® approved by U.S. Food and Drug Administration on Nov. 26, 1997.

Janakirman N. et al. *Blood* 92(10 Suppl. 1): 337a, abst. No. 1384, Nov. 1998. Rituximab: correlation between effector cells and clinical activity in NHL.

Kinoshita T. et al. *J. Clin. Oncol.* 16(12): 3916, Dec. 1998. CD20-negative relapse in B-cell lymphoma after treatment with Rituximab.

Maloney D.C. et al. *Blood* 90(6): 2188-2195, 1997. IDEC-C2B8 (Rituximab) anti-CD20 monoclonal antibody therapy in patients with relapsed low-grade non-Hodgkin's lymphoma.

Maloney D.G. et al. *Blood* 88(10: Suppl. 1): 637a, abst. No. 2635, 1996. The anti-tumor effect of monoclonal anti-CD20 antibody (mAb) therapy includes direct anti-proliferative activity and induction of apoptosis in CD20 positive non-Hodgkin's lymphoma (NHL) cell lines.

Maloney D.G. et al. *J. Clin. Oncol.* 15(10): 3266-3274, Oct. 1997. IDEC-C2B8: results of a phase 1 multiple-dose trial in patients with relapsed non-Hodgkin's Lymphoma.

Maloney D.M. et al. *Blood* 84(8): 2457-66, 1994. Phase I clinical trial using escalating single-dose infusion of chimeric anti-CD20 monoclonal antibody (IDEC-C2B8) in patients with recurrent B-cell lymphoma.

McLaughlin P. et al. *Blood* 92(10 Suppl. 1): 414a-415a, abst. No. 1712, Nov. 1998. Efficacy controls and long-term follow-up for relapsed or refractory, low-grade or follicular (R-LG/F) NHL.

McLaughlin P. et al. *J. Clin. Oncol.* 16(8): 2825-2833, Aug. 1998. Rituximab chimeric-anti-CD20 monoclonal antibody therapy for relapsed indolent lymphoma: half of patients respond to a four-dose treatment program.

McLaughlin P. et al. *Oncology* 12(12): 1763-81, 1998. Clinical status and optimal use of rituximab for B-cell lymphomas.

Non-Hodgkin's Lymphoma Pathologic Classification Project. *Cancer* 49(10): 2112-35, 1982. National Cancer Institute sponsored study of classifications of non-Hodgkin's lymphomas.

Pietersz G.A. et al. *Immunol. Cell. Biol.* 65(2): 111-25, 1987. The use of monoclonal antibody conjugates for the diagnosis and treatment of cancer.

Piro L.D. et al. *Ann. Oncol.* 10: 655-61, 1999. Extended Rituximab (anti-CD20 monoclonal antibody) therapy for relapsed or refractory low-grade or follicular non-Hodgkin's lymphoma.

Press O.W. *Cancer J. Sci. Amer.* 4(Suppl 2): S19-S26, Jul. 1998. Prospects for the management of non-Hodgkin's lymphomas with monoclonal antibodies and immunoconjugates.

Teeling J.L. et al. *Blood* 104:1793-1800, 2004. Characterization of new human CD20 monoclonal antibodies with potent cytolytic activity against non-Hodgkin lymphomas.

Teeling J.L. et al. *J. Immunol.* 277: 362-71, 2006. The biological activity of human CD20 monoclonal antibodies is linked to unique epitopes on CD20.

White C.A. et al. *Ann. Oncol.* 10(3 Suppl): 64, abst. No. 215, 1999. Radioimmunotherapy of relapsed or refractory non-Hodgkin's lymphoma (NHL): IDEC-Y2B8 phase I/II $^{90}$yttrium trial.

White C.A. et al. *Ann. Rev. Med.* 52: 125-45, 2001. Antibody-targeted immunotherapy for treatment of malignancy.

White C.A. et al. *Blood* 87(9): 3640-49, 1996. Radioimmunotherapy of relapsed B-cell lymphoma with Yttrium 90 anti-idiotype monoclonal antibodies.

White C.A. et al. *Eur. J. Cancer* 35: S57, abst. No. 107, 1999. Zevalin™ radioimmunotherapy of relapsed or refractory non-Hodgkin's lymphoma.

Witzig T. et al. *Blood* 90(10 Suppl. 1): 586a, abst. No. 2606, 1997. IDEC-Y2B8 $^{90}$yttrium anti-CD20 radioimmunotherapy of relapsed non-Hodgkin's lymphoma (NHL): interim results of a phase I/II trial.

Witzig T.E. et al. *J. Clin. Oncol.* 17(12): 3793-3803, 1999. Phase I/II trial of IDEC-Y2B8 radioimmunotherapy for treatment of relapsed or refractory CD20(+) B-cell non-Hodgkin's lymphoma.

Witzig T.E. et al. *J. Clin. Oncol.* 20: 2453-63, 2002. Randomized controlled trial of yttrium-90-labeled ibritumomab tiuxetan radioimmunotherapy versus rituximab immunotherapy for patients with relapsed or refractory low-grade, follicular, or transformed B-cell non-Hodgkin's lymphoma.

Witzig T.E. et al. *Blood* 94(10 Suppl. 1): 631a, abst. No. 2805, 1999. Prospective randomized controlled study of Zevalin™ (IDEC-Y2B8) radioimmunotherapy compared to rituximab immunotherapy for B-cell NHL: report of interim results.

```
                LINKER #1 15bp|               SV40 ORIGIN=332bp
GACGTCGCGG CCGCT|CTAGG CCTCCAAAAA AGCCTCCTCA CTACTTCTGG AATAGCTCAG    60

AGGCCGAGGC GGCCTCGGCC TCTGCATAAA TAAAAAAAAT TAGTCAGCCA TGCATGGGGC    120

GGAGAATGGG CGGAACTGGG CGGAGTTAGG GGCGGGATGG GCGGAGTTAG GGGCGGGACT   180

ATGGTTGCTG ACTAATTGAG ATGCATGCTT TGCATACTTC TGCCTGCTGG GGAGCCTGGG   240

GACTTTCCAC ACCTGGTTGC TGACTAATTG AGATGCATGC TTTGCATACT TCTGCCTGCT   300
                                                 |LINKER #2=13bp|
GGGGAGCCTG GGGACTTTCC ACACCCTAAC TGACACACAT TCCACAGAAT TAATTCCCCT   360
                                            347'8            360'1
AGTTATTAAT AGTAATCAAT TACGGGGTCA TTAGTTCATA GCCCATATAT GGAGTTCCGC   420

GTTACATAAC TTACGGTAAA TGGCCCGCCT GGCTGACCGC CCAACGACCC CCGCCCATTG   480
                   CMV PROMOTER-ENHANCER=567bp
ACGTCAATAA TGACGTATGT TCCCATAGTA ACGCCAATAG GGACTTTCCA TTGACGTCAA   540

TGGGTGGACT ATTTACGGTA AACTGCCCAC TTGGCAGTAC ATCAAGTGTA TCATATGCCA   600

AGTACGCCCC CTATTGACGT CAATGACGGT AAATGGCCCG CCTGGCATTA TGCCCAGTAC   660

ATGACCTTAT GGGACTTTCC TACTTGGCAG TACATCTACG TATTAGTCAT CGCTATTACC   720

ATGGTGATGC GGTTTTGGCA GTACATCAAT GGGCGTGGAT AGCGGTTTGA CTCACGGGGA   780

TTTCCAAGTC TCCACCCCAT TGACGTCAAT GGGAGTTTGT TTTGGCACCA AAATCAACGG   840

GACTTTCCAA AATGTCGTAA CAACTCCGCC CCATTGACGC AAATGGGCGG TAGGCGTGTA   900
                      |LINKER #3=76bp|
CGGTGGGAGG TCTATATAAG CAGAGCTGGG TACGTGAACC GTCAGATCGC CTGGAGACGC   960
        Bgl II              727'8                 LEADER=60bp
CATCACAGAT CTCTCACCAT GAGGGTCCCC GCTCAGCTCC TGGGGCTCCT GCTGCTCTGG  1020
         978'9
          |+1 |101 102               107|108
CTCCCAGGTG CACGATGTGA TGGTACCAAG GTGGAAATCA AACGTACGGT GGCTGCACCA  1080
          1038'9                          1062'3 Bsi WI

TCTGTCTTCA TCTTCCCGCC ATCTGATGAG CAGTTGAAAT CTGGAACTGC CTCTGTTGTG  1140

TGCCTGCTGA ATAACTTCTA TCCCAGAGAG GCCAAAGTAC AGTGGAAGGT GGATAACGCC  1200
       HUMAN KAPPA CONSTANT 324bp 107 AMINO ACID & STOP CODON
CTCCAATCGG GTAACTCCCA GGAGAGTGTC ACAGAGCAGG ACAGCAAGGA CAGCACCTAC  1260

AGCCTCAGCA GCACCCTGAC GCTGAGCAAA GCAGACTACG AGAAACACAA AGTCTACGCC  1320

TGCGAAGTCA CCCATCAGGG CCTGAGCTCG CCCGTCACAA AGAGCTTCAA CAGGGGAGAG  1380
STOP
LIGHT
CHAIN  | Eco RI               LINKER #4=85bp
TGT|TGA|ATTC AGATCCGTTA ACGGTTACCA ACTACCTAGA CTGGATTCGT GACAACATGC  1440
1386'7
GGCCGTGATA TCTACGTATG ATCAGCCTCG A|CTGTGCCTT CTAGTTGCCA GCCATCTGTT   1500
                                1471'2
```

FIG. 2A

```
GTTTGCCCCT CCCCCGTGCC TTCCTTGACC CTGGAAGGTG CCACTCCCAC TGTCCTTTCC 1560
                         BGH poly A=231bp
TAATAAAATG AGGAAATTGC ATCGCATTGT CTGAGTAGGT GTCATTCTAT TCTGGGGGGT 1620

GGGGTGGGGC AGGACAGCAA GGGGGAGGAT TGGGAAGACA ATAGCAGGCA TGCTGGGGAT 1680
                        | LINKER #5=15bp |
GCGGTGGGCT CTATGGAACC AGCTGGGGCT CGACAGCTAT GCCAAGTACG CCCCCTATTG 1740
                    1702 3          1717 8

ACGTCAATGA CGGTAAATGG CCCGCCTGGC ATTATGCCCA GTACATGACC TTATGGGACT 1800

TTCCTACTTG GCAGTACATC TACGTATTAG TCATCGCTAT TACCATGGTG ATGCGGTTTT 1860
                        CMV PROMOTER-ENHANCER=334bp
GGCAGTACAT CAATGGGCGT GGATAGCGGT TTGACTCACG GGGATTTCCA AGTCTCCACC 1920

CCATTGACGT CAATGGGAGT TTGTTTTGGC ACCAAAATCA ACGGGACTTT CCAAAATGTC 1980

GTAACAACTC CGCCCCATTG ACGCAAATGG GCGGTAGGCG TGTACGGTGG GAGGTCTATA 2040
      | LINKER #6=7bp |                                    Sal I
TAAGCAGAGC TGGGTACGTC CTCACATTCA GTGATCAGCA CTGAACACAG ACCCGTCGAC 2100
      2051 2 2058 9         LEADER=51bp           Mlu I 2151 2 Nhe I
ATGGGTTGGA GCCTCATCTT GCTCTTCCTT GTCGCTGTTG CTACGCGTGT CGCTAGCACC 2160
 START HEAVY CHAIN                               -5 -4 -3 114 115

AAGGGCCCAT CGGTCTTCCC CCTGGCACCC TCCTCCAAGA GCACCTCTGG GGGCACAGCG 2220

GCCCTGGGCT GCCTGGTCAA GGACTACTTC CCCGAACCGG TGACGGTGTC GTGGAACTCA 2280

GGCGCCCTGA CCAGCGGCGT GCACACCTTC CCGGCTGTCC TACAGTCCTC AGGACTCTAC 2340
                        HUMAN GAMMA 1 CONSTANT
TCCCTCAGCA GCGTGGTGAC CGTGCCCTCC AGCAGCTTGG GCACCCAGAC CTACATCTGC 2400
                        993bp=330 AMINO ACID & STOP CODON
AACGTGAATC ACAAGCCCAG CAACACCAAG GTGGACAAGA AAGCAGAGCC CAAATCTTGT 2460

GACAAAACTC ACACATGCCC ACCGTGCCCA GCACCTGAAC TCCTGGGGGG ACCGTCAGTC 2520

TTCCTCTTCC CCCCAAAACC CAAGGACACC CTCATGATCT CCCGGACCCC TGAGGTCACA 2580

TGCGTGGTGG TGGACGTGAG CCACGAAGAC CCTGAGGTCA AGTTCAACTG GTACGTGGAC 2640

GGCGTGGAGG TGCATAATGC CAAGACAAAG CCGCGGGAGG AGCAGTACAA CAGCACGTAC 2700

CGTGTGGTCA GCGTCCTCAC CGTCCTGCAC CAGGACTGGC TGAATGGCAA GGACTACAAG 2760

TGCAAGGTCT CCAACAAAGC CCTCCCAGCC CCCATCGAGA AAACCATCTC CAAAGCCAAA 2820

GGGCAGCCCC GAGAACCACA GGTGTACACC CTGCCCCCAT CCCGGGATGA GCTGACCAGG 2880

AACCAGGTCA GCCTGACCTG CCTGGTCAAA GGCTTCTATC CAGCGACAT CGCCGTGGAG 2940

TGGGAGAGCA ATGGGCAGCC GGAGAACAAC TACAAGACCA CGCCTCCCGT GCTGGACTCC 3000
```

*FIG. 2B*

```
                                                              STOP HEAVY CHAIN  Bam HI              LINKER #7=81bp
GACGGCTCCT TCTTCCTCTA CAGCAAGCTC ACCGTGGACA AGAGCAGGTG GCAGCAGGGG 3060
AACGTCTTCT CATGCTCCGT GATGCATGAG GCTCTGCACA ACCACTACAC GCAGAAGAGC 3120
       STOP HEAVY CHAIN  Bam HI              LINKER #7=81bp
CTCTCCCTGT CTCCGGGTAA ATGAGGATCC GTTAACGGTT ACCAACTACC TAGACTGGAT 3180
                      3144  5
TCGTGACAAC ATGCGGCCGT GATATCTACG TATGATCAGC CTCGACTGTG CCTTCTAGTT 3240
                                            3225  6
GCCAGCCATC TGTTGTTTGC CCCTCCCCCG TGCCTTCCTT GACCCTGGAA GGTGCCACTC 3300
              BOVINE GROWTH HORMONE POLYADENYLATION REGION=231bp
CCACTGTCCT TTCCTAATAA AATGAGGAAA TTGCATCGCA TTGTCTGAGT AGGTGTCATT 3360
CTATTCTGGG GGGTGGGGTG GGGCAGGACA GCAAGGGGGA GGATTGGGAA GACAATAGCA 3420
                                                    LINKER #8=34bp
GGCATGCTGG GGATGCGGTG GGCTCTATGG AACCAGCTGG GGCTCGACAG CGCTGGATCT 3480
                                       3456  7
CCCGATCCCC AGCTTTGCTT CTCAATTTCT TATTTGCATA ATGAGAAAAA AAGGAAAATT 3540
   3490   1
AATTTTAACA CCAATTCAGT AGTTGATTGA GCAAATGCGT TGCCAAAAAG GATGCTTTAG 3600
              MOUSE BETA GLOBIN MAJOR PROMOTER=366bp
AGACAGTGTT CTCTGCACAG ATAAGGACAA ACATTATTCA GAGGGAGTAC CCAGAGCTGA 3660
GACTCCTAAG CCAGTGAGTG GCACAGCATT CTAGGGAGAA ATATGCTTGT CATCACCGAA 3720
GCCTGATTCC GTAGAGCCAC ACCTTGGTAA GGGCCAATCT GCTCACACAG GATAGAGAGG 3780
GCAGGAGCCA GGGCAGAGCA TATAAGGTGA GGTAGGATCA GTTGCTCCTC ACATTTGCTT 3840
              LINKER #9=19bp            5' UNTRANSLATED DHFR=82bp
CTGACATAGT TGTGTTGGGA GCTTGGATAG CTTGGACAGC TCAGGGCTGC GATTTCGCGC 3900
              3856  7                  3875  6
                                                     START DHFR
CAAACTTGAC GGCAATCCTA GCGTGAAGGC TGGTAGGATT TTATCCCCGC TGCCATCATG 3960
                                                           3957  8
GTTCGACCAT TGAACTGCAT CGTCGCCGTG TCCCAAAATA TGGGGATTGG CAAGAACGGA 4020
GACCTACCCT GGCCTCCGCT CAGGAACGAG TTCAAGTACT TCCAAAGAAT GACCACAACC 4080
TCTTCAGTGG AAGGTAAACA GAATCTGGTG ATTATGGGTA GGAAAACCTG GTTCTCCATT 4140
              MOUSE DHFR=564bp=187 AMINO ACID & STOP CODON
CCTGAGAAGA ATCGACCTTT AAAGGACAGA ATTAATATAG TTCTCAGTAG AGAACTCAAA 4200
GAACCACCAC GAGGAGCTCA TTTTCTTGCC AAAAGTTTGG ATGATGCCTT AAGACTTATT 4260
GAACAACCGG AATTGGCAAG TAAAGTAGAC ATGGTTTGGA TAGTCGGAGG CAGTTCTGTT 4320
TACCAGGAAG CCATGAATCA ACCAGGCCAC CTTAGACTCT TTGTGACAAG GATCATGCAG 4380
GAATTTGAAA GTGACACGTT TTTCCCAGAA ATTGATTTGG GGAAATATAA ACTTCTCCCA 4440
GAATACCCAG GCGTCCTCTC TGAGGTCCAG GAGGAAAAAG GCATCAAGTA TAAGTTTGAA 4500
```

*FIG. 2C*

```
                    STOP DHFR
GTCTACGAGA AGAAAGAC TA A CAGGAAGAT GCTTTCAAGT TCTCTGCTCC CCTCCTAAAG 4560
                  4521  2
    3' UNTRANSLATED DHFR=82bp                    LINKER #10=10bp
TCATGCATTT TTATAAGACC ATGGGACTTT TGCTGGCTTT AGA TCAGCCT CGA CTGTGCC 4620
                                           4603  4     4613  4
TTCTAGTTGC CAGCCATCTG TTGTTTGCCC CTCCCCCGTG CCTTCCTTGA CCCTGGAAGG 4680
       BOVINE GROWTH HORMONE POLYADENYLATION REGION=231bp
TGCCACTCCC ACTGTCCTTT CCTAATAAAA TGAGGAAATT GCATCGCATT GTCTGAGTAG 4740

GTGTCATTCT ATTCTGGGGG GTGGGGTGGG GCAGGACAGC AAGGGGGAGG ATTGGGAAGA 4800
                                            LINKER #11=17bp
CAATAGCAGG CATGCTGGGG ATGCGGTGGG CTCTATGGAA CCAG CTGGGG CTCGAGCTAC 4860
                                            4844  5
T AGCTTTGCT TCTCAATTTC TTATTTGCAT AATGAGAAAA AAAGGAAAAT TAATTTTAAC 4920

ACCAATTCAG TAGTTGATTG AGCAAATGCG TTGCCAAAAA GGATGCTTTA GAGACAGTGT 4980
              MOUSE BETA GLOBIN MAJOR PROMOTER=366bp
TCTCTGCACA GATAAGGACA AACATTATTC AGAGGGAGTA CCCAGAGCTG AGACTCCTAA 5040

GCCAGTGAGT GGCACAGCAT TCTAGGGAGA AATATGCTTG TCATCACCGA AGCCTGATTC 5100

CGTAGAGCCA CACCTTGGTA AGGGCCAATC TGCTCACACA GGATAGAGAG GGCAGGAGCC 5160

AGGGCAGAGC ATATAAGGTG AGGTAGGATC AGTTGCTCCT CACATTTGCT TCTGACATAG 5220
          LINKER #12=21bp    START NEO
TTGTGTT GGG AGCTTGGATC GATCCTCT AT G GTTGAACAA GATGGATTGC ACGCAGGTTC 5280
      5227  8            5248  9
TCCGGCCGCT TGGGTGGAGA GGCTATTCGG CTATGACTGG GCACAACAGA CAATCGGCTG 5340

CTCTGATGCC GCCGTGTTCC GGCTGTCAGC GCAGGGGCGC CCGGTTCTTT TTGTCAAGAC 5400
               NEOMYCIN PHOSPHOTRANSFERASE
CGACCTGTCC GGTGCCCTGA ATGAACTGCA GGACGAGGCA GCGGGCTAT CGTGGCTGGC 5460
       795bp=264 AMINO ACIDS & STOP CODON
CACGACGGGC GTTCCTTGCG CAGCTGTGCT CGACGTTGTC ACTGAAGCGG GAAGGGACTG 5520

GCTGCTATTG GGCGAAGTGC CGGGGCAGGA TCTCCTGTCA TCTCACCTTG CTCCTGCCGA 5580

GAAAGTATCC ATCATGGCTG ATGCAATGCG GCGGCTGCAT ACGCTTGATC CGGCTACCTG 5640

CCCATTCGAC CACCAAGCGA AACATCGCAT CGAGCGAGCA CGTACTCGGA TGGAAGCCGG 5700

TCTTGTCGAT CAGGATGATC TGGACGAAGA GCATCAGGGG CTCGCGCCAG CCGAACTGTT 5760

CGCCAGGCTC AAGGCGCGCA TGCCCGACGG CGAGGATCTC GTCGTGACCC ATGGCGATGC 5820

CTGCTTGCCG AATATCATGG TGGAAAATGG CCGCTTTTCT GGATTCATCG ACTGTGGCCG 5880

GCTGGGTGTG GCGGACCGCT ATCAGGACAT AGCGTTGGCT ACCCGTGATA TTGCTGAAGA 5940

GCTTGGCGGC GAATGGGCTG ACCGCTTCCT CGTGCTTTAC GGTATCGCCG CT CCCGATTC 6000
```

*FIG. 2D*

```
                                                      STOP NEO
GCAGCGCATC GCCTTCTATC GCCTTCTTGA CGAGTTCTTC TGAGCGGGAC TCTGGGGTTC 6060
                                           6043 4
GAAATGACCG ACCAAGCGAC GCCCAACCTG CCATCACGAG ATTTCGATTC CACCGCCGCC 6120
                   3' UNTRANSLATED NEO=173bp
TTCTATGAAA GGTTGGGCTT CGGAATCGTT TTCCGGGACG CCGGCTGGAT GATCCTCCAG 6180

CGCGGGGATC TCATGCTGGA GTTCTTCGCC CACCCCAACT TGTTTATTGC AGCTTATAAT 6240
                                   6216 7
GGTTACAAAT AAAGCAATAG CATCACAAAT TTCACAAATA AAGCATTTTT TTCACTGCAT 6300
             SV40 POLY A EARLY=133bp        LINKER #13=19bp
TCTAGTTGTG GTTTGTCCAA ACTCATCAAT CTATCTTATC ATGTCTGGAT CGCGGCCGCG 6360
                                            6349 50
ATCCCGTCGA GAGCTTGGCG TAATCATGGT CATAGCTGTT TCCTGTGTGA AATTGTTATC 6420
6368 9
CGCTCACAAT TCCACACAAC ATACGAGCCG GAAGCATAAA GTGTAAAGCC TGGGGTGCCT 6480

AATGAGTGAG CTAACTCACA TTAATTGCGT TGCGCTCACT GCCCGCTTTC CAGTCGGGAA 6540

ACCTGTCGTG CCAGCTGCAT TAATGAATCG GCCAACGCGC GGGGAGAGGC GGTTTGCGTA 6600
                           PVC 19
TTGGGCGCTC TTCCGCTTCC TCGCTCACTG ACTCGCTGCG CTCGGTCGTT CGGCTGCGGC 6660

GAGCGGTATC AGCTCACTCA AAGGCGGTAA TACGGTTATC CACAGAATCA GGGGATAACG 6720

CAGGAAAGAA CATGTGAGCA AAAGGCCAGC AAAAGGCCAG GAACCGTAAA AAGGCCGCGT 6780
          6792=BACTERIAL ORIGIN OF REPLICATION
TGCTGGCGTT TTTCCATAGG CTCCGCCCCC CTGACGAGCA TCACAAAAAT CGACGCTCAA 6840

GTCAGAGGTG GCGAAACCCG ACAGGACTAT AAAGATACCA GGCGTTTCCC CCTGGAAGCT 6900

CCCTCGTGCG CTCTCCTGTT CCGACCCTGC CGCTTACCGG ATACCTGTCC GCCTTTCTCC 6960

CTTCGGGAAG CGTGGCGCTT TCTCAATGCT CACGCTGTAG GTATCTCAGT TCGGTGTAGG 7020

TCGTTCGCTC CAAGCTGGGC TGTGTGCACG AACCCCCCGT TCAGCCCGAC CGCTGCGCCT 7080

TATCCGGTAA CTATCGTCTT GAGTCCAACC CGGTAAGACA CGACTTATCG CCACTGGCAG 7140

CAGCCACTGG TAACAGGATT AGCAGAGCGA GGTATGTAGG CGGTGCTACA GAGTTCTTGA 7200

AGTGGTGGCC TAACTACGGC TACACTAGAA GGACAGTATT TGGTATCTGC GCTCTGCTGA 7260

AGCCAGTTAC CTTCGGAAAA AGAGTTGGTA GCTCTTGATC CGGCAAACAA ACCACCGCTG 7320

GTAGCGGTGG TTTTTTTGTT TGCAAGCAGC AGATTACGCG CAGAAAAAAA GGATCTCAAG 7380

AAGATCCTTT GATCTTTTCT ACGGGGTCTG ACGCTCAGTG GAACGAAAAC TCACGTTAAG 7440

GGATTTTGGT CATGAGATTA TCAAAAAGGA TCTTCACCTA GATCCTTTTA AATTAAAAAT 7500
```

*FIG. 2E*

```
                                    STOP BETA LACTAMASE
GAAGTTTTAA ATCAATCTAA AGTATATATG AGTAAACTTG GTCTGACAG T TA CCAATGCT 7560
                                                   7550
TAATCAGTGA GGCACCTATC TCAGCGATCT GTCTATTTCG TTCATCCATA GTTGCCTGAC 7620
TCCCCGTCGT GTAGATAACT ACGATACGGG AGGGCTTACC ATCTGGCCCC AGTGCTGCAA 7680
TGATACCGCG AGACCCACGC TCACCGGCTC CAGATTTATC AGCAATAAAC CAGCCAGCCG 7740
                     BETA LACTAMASE=861bp
GAAGGGCCGA GCGCAGAAGT GGTCCTGCAA CTTTATCCGC CTCCATCCAG TCTATTAATT 7800
          286 AMINO ACID & STOP CODON
GTTGCCGGGA AGCTAGAGTA AGTAGTTCGC CAGTTAATAG TTTGCGCAAC GTTGTTGCCA 7860
TTGCTACAGG CATCGTGGTG TCACGCTCGT CGTTTGGTAT GGCTTCATTC AGCTCCGGTT 7920
CCCAACGATC AAGGCGAGTT ACATGATCCC CCATGTTGTG CAAAAAAGCG GTTAGCTCCT 7980
TCGGTCCTCC GATCGTTGTC AGAAGTAAGT TGGCCGCAGT GTTATCACTC ATGGTTATGG 8040
CAGCACTGCA TAATTCTCTT ACTGTCATGC CATCCGTAAG ATGCTTTTCT GTGACTGGTG 8100
AGTACTCAAC CAAGTCATTC TGAGAATAGT GTATGCGGCG ACCGAGTTGC TCTTGCCCGG 8160
CGTCAATACG GGATAATACC GCGCCACATA GCAGAACTTT AAAAGTGCTC ATCATTGGAA 8220
AACGTTCTTC GGGGCGAAAA CTCTCAAGGA TCTTACCGCT GTTGAGATCC AGTTCGATGT 8280
AACCCACTCG TGCACCCAAC TGATCTTCAG CATCTTTTAC TTTCACCAGC GTTTCTGGGT 8340
GAGCAAAAAC AGGAAGGCAA AATGCCGCAA AAAGGGAAT AAGGGCGACA CGGAAATGTT 8400
           START BETA LACTAMASE
GAATACT CAT ACTCTTCCTT TTTCAATATT ATTGAAGCAT TTATCAGGGT TATTGTCTCA 8460
        8410
TGAGCGGATA CATATTTGAA TGTATTTAGA AAAATAAACA AATAGGGGTT CCGCGCACAT 8520
TTCCCCGAAA AGTGCCACCT
```

*FIG. 2F*

```
                    LINKER #1=15bp
        GACGTCGCGG  CCGCTCTAGG  CCTCCAAAAA  AGCCTCCTCA  CTACTTCTGG  AATAGCTCAG   60
                       15  6
        AGGCCGAGGC  GGCCTCGGCC  TCTGCATAAA  TAAAAAAAAT  TAGTCAGCCA  TGCATGGGGC  120
                                SV40 ORIGIN=332bp
        GGAGAATGGG  CGGAACTGGG  CGGAGTTAGG  GGCGGGATGG  GCGGAGTTAG  GGGCGGGACT  180

ATGGTTGCTG  ACTAATTGAG  ATGCATGCTT  TGCATACTTC  TGCCTGCTGG  GGAGCCTGGG  240

GACTTTCCAC  ACCTGGTTGC  TGACTAATTG  AGATGCATGC  TTTGCATACT  TCTGCCTGCT  300
                                                        LINKER #2=13bp
        GGGGAGCCTG  GGGACTTTCC  ACACCCTAAC  TGACACACAT  TCCACAGAAT  TAATTCCCCT  360
                                                        347  8
        AGTTATTAAT  AGTAATCAAT  TACGGGGTCA  TTAGTTCATA  GCCCATATAT  GGAGTTCCGC  420

GTTACATAAC  TTACGGTAAA  TGGCCCGCCT  GGCTGACCGC  CCAACGACCC  CCGCCCATTG  480

ACGTCAATAA  TGACGTATGT  TCCCATAGTA  ACGCCAATAG  GGACTTTCCA  TTGACGTCAA  540
                    CVM PROMOTER-ENHANCER=567bp
        TGGGTGGACT  ATTTACGGTA  AACTGCCCAC  TTGGCAGTAC  ATCAAGTGTA  TCATATGCCA  600

AGTACGCCCC  CTATTGACGT  CAATGACGGT  AAATGGCCCG  CCTGGCATTA  TGCCCAGTAC  660

ATGACCTTAT  GGGACTTTCC  TACTTGGCAG  TACATCTACG  TATTAGTCAT  CGCTATTACC  720

ATGGTGATGC  GGTTTTGGCA  GTACATCAAT  GGGCGTGGAT  AGCGGTTTGA  CTCACGGGGA  780

TTTCCAAGTC  TCCACCCCAT  TGACGTCAAT  GGGAGTTTGT  TTTGGCACCA  AAATCAACGG  840

GACTTTCCAA  AATGTCGTAA  CAACTCCGCC  CCATTGACGC  AAATGGGCGG  TAGGCGTGTA  900
                       LINKER #3=7bp
        CGGTGGGAGG  TCTATATAAG  CAGAGCTGGG  TACGTGAACC  GTCAGATCGC  CTGGAGACGC  960
                                927  8    934  5
          Bgl 2              START LIGHT CHAIN      NATURAL LEADER=66bp
        CATCACAGAT  CTCTCACTAT  GGATTTTCAG  GTGCAGATTA  TCAGCTTCCT  GCTAATCAGT  1020
                       978  9
        GCTTCAGTCA  TAATGTCCAG  AGGACAAATT  GTTCTCTCCC  AGTCTCCAGC  AATCCTGTCT  1080
                                1044  5  +1
        GCATCTCCAG  GGAGAAGGT   CACAATGACT  TGCAGGGCCA  GCTGAAGTGT  AAGTTACATC  1140

CACTGGTTCC  AGCAGAAGCC  AGGATCCTCC  CCCAAACCCT  GGATTTATGC  CACATCCAAC  1200
                       LIGHT CHAIN VARIABLE REGION 318bp 106 AMINO ACID
        CTGGCTTCTG  GAGTCCCTGT  TCGCTTCAGT  GGCAGTGGGT  CTGGGACTTC  TTACTCTCTC  1260

ACCATCAGCA  GAGTGGAGGC  TGAAGATGCT  GCCACTTATT  ACTGCAGCA   GTGGACTAGT  1320
                                                        BsiWI
        AACCCACCCA  CGTTCGGAGG  GGGGACCAAG  CTGGAAATCA  AACGTACGGT  GGCTGCACCA  1380
                                                        1362  3
        TCTGTCTTCA  TCTTCCCGCC  ATCTGATGAG  CAGTTGAAAT  CTGGAACTGC  CTCTGTTGTG  1440

TGCCTGCTGA  ATAACTTCTA  TCCCAGAGAG  GCCAAAGTAC  AGTGGAAGGT  GGATAACGCC  1500
```

*FIG. 3A*

```
                HUMAN KAPPA CONSTANT=324bp=107 AMINO ACID & STOP CODON
CTCCAATCGG GTAACTCCCA GGAGAGTGTC ACAGAGCAGG ACAGCAAGGA CAGCACCTAC 1560

AGCCTCAGCA GCACCCTGAC GCTGAGCAAA GCAGACTACG AGAAACACAA AGTCTACGCC 1620

TGCGAAGTCA CCCATCAGGG CCTGAGCTCG CCCGTCACAA AGAGCTTCAA CAGGGGAGAG 1680
   STOP
   LIGHT
   CHAIN Eco RI              LINKER #4=81bp
TGT TGA ATTC AGATCCGTTA ACGGTTACCA ACTACCTAGA CTGGATTCGT GACAACATGC 1740
    1646 7                                |
GGCCGTGATA TCTACGTATG ATCAGCCTCG ACTGTGCCTT CTAGTTGCCA GCCATCTGTT 1800
                                1771 2

GTTTGCCCCT CCCCCGTGCC TTCCTTGACC CTGGAAGGTG CCACTCCCAC TGTCCTTTCC 1860

TAATAAAATG AGGAAATTGC ATCGCATTGT CTGAGTAGGT GTCATTCTAT TCTGGGGGGT 1920
           BOVINE GROWTH HORMONE POLYADENYLATION REGION=231bp
GGGGTGGGGC AGGACAGCAA GGGGGAGGAT TGGGAAGACA ATAGCAGGCA TGCTGGGGAT 1980
                      | LINKER #5=15bp |
GCGGTGGGCT CTATGGAACC AGCTGGGGCT CGACAGCTAT GCCAAGTACG CCCCCTATTG 2040
                      2002 3         2017 8

ACGTCAATGA CGGTAAATGG CCCGCCTGGC ATTATGCCCA GTACATGACC TTATGGGACT 2100

TTCCTACTTG GCAGTACATC TACGTATTAG TCATCGCTAT TACCATGGTG ATGCGGTTTT 2160
                    CMV PROMOTER-ENHANCER=334bp
GGCAGTACAT CAATGGGCGT GGATAGCGGT TTGACTCACG GGGATTTCCA AGTCTCCACC 2220

CCATTGACGT CAATGGGAGT TTGTTTTGGC ACCAAAATCA ACGGGACTTT CCAAAATGTC 2280

GTAACAACTC CGCCCCATTG ACGCAAATGG GCGGTAGGCG TGTACGGTGG GAGGTCTATA 2340
            LINKER #6=7bp                                   Sal I
TAAGCAGAGC TGGGTACGTC CTCACATTCA GTGATCAGCA CTGAACACAG ACCCGTCGAC 2400
START       2351 2 2358 9
HEAVY CHAIN          SYNTHETIC & NATURAL LEADER     Mlu I      2457 8
ATGGGTTGGA GCCTCATCTT GCTCTTCCTT GTCGCTGTTG CTACGCGTGT CCTGTCCCAG 2460
2401                                                -5 -4 -3 -2 -1 +1

GTACAACTGC AGCAGCCTGG GGCTGAGCTG GTGAAGCCTG GGGCCTCAGT GAAGATGTCC 2520

TGCAAGGCTT CTGGCTACAC ATTTACCAGT TACAATATGC ACTGGGTAAA ACAGACACCT 2580
               HEAVY CHAIN VARIABLE=363bp=121 AMINO ACID
GGTCGGGGCC TGGAATGGAT TGGAGCTATT TATCCCGGAA ATGGTGATAC TTCCTACAAT 2640

CAGAAGTTCA AAGGCAAGGC CACATTGACT GCAGACAAAT CCTCCAGCAC AGCCTACATG 2700

CAGCTCAGCA GCCTGACATC TGAGGACTCT GCGGTCTATT ACTGTGCAAG ATCGACTTAC 2760

TACGGCGGTG ACTGGTACTT CAATGTCTGG GGCGCAGGGA CCACGGTCAC CGTCTCTGCA 2820
  Nhe I
GCTAGCACCA AGGGCCCATC GGTCTTCCCC CTGGCACCCT CCTCCAAGAG CACCTCTGGG 2880

GGCACAGCGG CCCTGGGCTG CCTGGTCAAG GACTACTTCC CCGAACCGGT GACGGTGTCG 2940
              HUMAN GAMMA 1 CONSTANT=993bp
TGGAACTCAG GCGCCCTGAC CAGCGGCGTG CACACCTTCC CGGCTGTCCT ACAGTCCTCA 3000
```

*FIG. 3B*

```
                    330 AMINO ACID & STOP CODON
GGACTCTACT CCCTCAGCAG CGTGGTGACC GTGCCCTCCA GCAGCTTGGG CACCCAGACC 3060
TACATCTGCA ACGTGAATCA CAAGCCCAGC AACACCAAGG TGGACAAGAA AGCAGAGCCC 3120
AAATCTTGTG ACAAAACTCA CACATGCCCA CCGTGCCCAG CACCTGAACT CCTGGGGGGA 3180
CCGTCAGTCT TCCTCTTCCC CCCAAAACCC AAGGACACCC TCATGATCTC CCGGACCCCT 3240
GAGGTCACAT GCGTGGTGGT GGACGTGAGC CACGAAGACC CTGAGGTCAA GTTCAACTGG 3300
TACGTGGACG GCGTGGAGGT GCATAATGCC AAGACAAAGC CGCGGGAGGA GCAGTACAAC 3360
AGCACGTACC GTGTGGTCAG CGTCCTCACC GTCCTGCACC AGGACTGGCT GAATGGCAAG 3420
GAGTACAAGT GCAAGGTCTC CAACAAAGCC CTCCCAGCCC CCATCGAGAA AACCATCTCC 3480
AAAGCCAAAG GGCAGCCCCG AGAACCACAG GTGTACACCC TGCCCCCATC CCGGGATGAG 3540
CTGACCAAGA ACCAGGTCAG CCTGACCTGC CTGGTCAAAG GCTTCTATCC CAGCGACATC 3600
GCCGTGGAGT GGGAGAGCAA TGGGCAGCCG GAGAACAACT ACAAGACCAC GCCTCCCGTG 3660
CTGGACTCCG ACGGCTCCTT CTTCCTCTAC AGCAAGCTCA CCGTGGACAA GAGCAGGTGG 3720
CAGCAGGGGA ACGTCTTCTC ATGCTCCGTG ATGCATGAGG CTCTGCACAA CCACTACACG 3780
              STOP HEAVY CHAIN  Bam HI         LINKER #7=81bp
CAGAAGAGCC TCTCCCTGTC TCCGGGTAAA TGAGGATCCG TTAACGGTTA CCAACTACCT 3840
                                3813 4
AGACTGGATT CGTGACAACA TGCGGCCGTG ATATCTACGT ATGATCAGCC TCGACTGTGC 3900
                                                      3894 5
CTTCTAGTTG CCAGCCATCT GTTGTTTGCC CCTCCCCCGT GCCTTCCTTG ACCCTGGAAG 3960
GTGCCACTCC CACTGTCCTT TCCTAATAAA ATGAGGAAAT TGCATCGCAT TGTCTGAGTA 4020
       BOVINE GROWTH HORMONE POLYADENYLATION REGION=231bp
GGTGTCATTC TATTCTGGGG GGTGGGGTGG GGCAGGACAG CAAGGGGGAG GATTGGGAAG 4080
                                          | LINKER #8=34bp
ACAATAGCAG GCATGCTGGG GATGCGGTGG GCTCTATGGA ACCAGCTGGG GCTCGACAGC 4140
                                            4125 6
GCTGGATCTC CCGATCCCCA GCTTTGCTTC TCAATTTCTT ATTTGCATAA TGAGAAAAAA 4200
AGGAAAATTA ATTTTAACAC CAATTCAGTA GTTGATTGAG CAAATGCGTT GCCAAAAAGG 4260
              MOUSE BETA GLOBIN MAJOR PROMOTER=366bp
ATGCTTTAGA GACAGTGGTC TCTGCACAGA TAAGGACAAA CATTATTCAG AGGGAGTACC 4320
CAGAGCTGAG ACTCCTAAGC CAGTGAGTGG CACAGCATTC TAGGGAGAAA TATGCTTGTC 4380
ATCACCGAAG CCTGATTCCG TAGAGCCACA CCTTGGTAAG GCCAATCTG CTCACACAGG 4440
ATAGAGAGGG CAGGAGCCAG GGCAGAGCAT ATAAGGTGAG GTAGGATCAG TTGCTCCTCA 4500
```

*FIG. 3C*

```
                           LINKER #9=19bP    5' UNTRANSLATED DHFR=82bp
CATTTGCTTC TGACATAGTT GTGTTGGGAG CTTGGATAGC TTGGACAGCT CAGGGCTGCG  4560
                      4525 6              4544 5

ATTTCGCGCC AAACTTGACG GCAATCCTAG CGTGAAGGCT GGTAGGATTT TATCCCCGCT  4620

START DHFR
GCCATCATGG TTCGACCATT GAACTGCATC GTCGCCGTGT CCCAAAATAT GGGGATTGGC  4680
4626 7

AAGAACGGAG ACCTACCCTG GCCTCCGCTC AGGAACGAGT TCAAGTACTT CCAAAGAATG  4740

ACCACAACCT CTTCAGTGGA AGGTAAACAG AATCTGGTGA TTATGGGTAG GAAAACCTGG  4800
            DHFR=564bp=187 AMINO ACID & STOP CODON
TTCTCCATTC CTGAGAAGAA TCGACCTTTA AAGGACAGAA TTAATATAGT TCTCAGTAGA  4860

GAACTCAAAG AACCACCACG AGGAGCTCAT TTTCTTGCCA AAAGTTTGGA TGATGCCTTA  4920

AGACTTATTG AACAACCGGA ATTGGCAAGT AAAGTAGACA TGGTTTGGAT AGTCGGAGGC  4980

AGTTCTGTTT ACCAGGAAGC CATGAATCAA CCAGGCCACC TTAGACTCTT TGTGACAAGG  5040

ATCATGCAGG AATTTGAAAG TGACACGTTT TTCCCAGAAA TTGATTTGGG GAAATATAAA  5100

CTTCTCCCAG AATACCCAGG CGTCCTCTCT GAGGTCCAGG AGGAAAAAGG CATCAAGTAT  5160
                STOP DHFR     3' UNTRANSLATED DHFR=82bp
AAGTTTGAAG TCTACGAGAA GAAAGACTAA CAGGAAGATG CTTTCAAGTT CTCTGCTCCC  5220
                      5140 1                              LINKER #10
CTCCTAAAGC TATGCATTTT TATAAGACCA TGGGACTTTT GCTGGCTTTA GATCAGCCTC  5280
=10bp                                                   5272 3
GACTGTGCCT TCTAGTTGCC AGCCATCTGT TGTTTGCCCC TCCCCCGTGC CTTCCTTGAC  5340
          BOVINE GROWTH HORMONE POLYADENYLATION=231bp
CCTGGAAGGT GCCACTCCCA CTGTCCTTTC CTAATAAAAT GAGGAAATTG CATCGCATTG  5400

TCTGAGTAGG TGTCATTCTA TTCTGGGGGG TGGGGTGGGG CAGGACAGCA AGGGGGAGGA  5460
                                                        LINKER #11
TTGGGAAGAC AATAGCAGGC ATGCTGGGGA TGCGGTGGGC TCTATGGAAC CAGCTGGGGC  5520
                                                      5513 4
=17bp
TCGAGCTACT AGCTTTGCTT CTCAATTTCT TATTTGCATA ATGAGAAAAA AAGGAAAATT  5580
5530 1
AATTTTAACA CCAATTCAGT AGTTGATTGA GCAAATGCGT TGCCAAAAAG GATGCTTTAG  5640
            MOUSE BETA GLOBIN MAJOR PROMOTER=366bp
AGACAGTGTT CTCTGCACAG ATAAGGACAA CTAGGGAGAA ATATGCTTGT CATCACCGAA  5700

GACTCCTAAG CCAGTGAGTG CACAGCATT CTAGGGAGAA ATATGCTTGT CATCACCGAA  5760

GCCTGATTCC GTAGAGCCAC ACCTTGGTAA GGGCCAATCT GCTCACACAG GATAGAGAGG  5820

GCAGGAGCCA GGGCAGAGCA TATAAGGTGA GGTAGGATCA GTTGCTCCTC ACATTTGCTT  5880
              LINKER #12=21bp     START NEO
CTGACATAGT TGTGTTGGGA GCTTGGATCG ATCCTCTATG GTTGAACAAG ATGGATTGCA  5940
             5896 7              5917 8
CGCAGGTTCT CCGGCCGCTT GGGTGGAGAG GCTATTCGGC TATGACTGGG CACAACAGAC  6000
```

*FIG. 3D*

AATCGGCTGC TCTGATGCCG CCGTGTTCCG GCTGTCAGCG CAGGGGCG:C CGGTTCT::T: 6060
NEOMYCIN PHOSPHOTRANSFERASE=795bP=264 AMINO ACID & STOP CODON
TGTCAAGACC GACCTGTCCG GTGCCCTGAA TGAACTGCAG GACGAGGCAG CGCGGCTATC 6120

GTGGCTGGCC ACGACGGGCG TTCCTTGCGC AGCTGTGCTC GACGTTGTCA CTGAAGCGGG 6180

AAGGGACTGG CTGCTATTGG GCGAAGTGCC GGGGCAGGAT CTCCTGTCAT CTCACCTTGC 6240

TCCTGCCGAG AAAGTATCCA TCATGGCTGA TGCAATGCGG CGGCTGCATA CGCTTGATCC F300

GGCTACCTGC CCATTCGACC ACCAAGCGAA ACATCGCATC GAGCGAGCAC GTACTCGGAT 63C0

GGAAGCCGGT CTTGTCGATC AGGATGATCT GGACGAAGAG CATCAGGGGC TCGCGCCAGC 6420

CGAACTGTTC GCCAGGCTCA AGGCGCGCAT GCCCGACGGC GAGGATCTCG TCGTGACCCA 6430

TGGCGATGCC TGCTTGCCGA ATATCATGGT GGAAAATGGC CGCTTTTCTG GATTCATCGA 6540

CTGTGGCCGG CTGGGTGTGG CGGACCGCTA TCAGGACATA GCGTTGGCTA CCCGTGA:A: 5600

TGCTGAAGAG CTTGGCGGCG AATGGGCTGA CCGCTTCCTC GTGCTTTACG GTATCGCCG: 6660
                                                STOP NEO
TCCCGATTCG CAGCGCATCG CCTTCTATCG CCTTCTTGAC GAGTTCTTCT GAGCGGGACT 6720
                                                6712 3
CTGGGGTTCG AAATGACCGA CCAAGCGACG CCCAACCTGC CATCACGAGA TTTCGATTCC 6780
                3' UNTRANSLATED NEO=173bp
ACCGCCGCCT TCTATGAAAG GTTGGGCTTC GGAATCGTTT TCCGGGACGC CGGCTGGATG 6840

ATCCTCCAGC GCGGGGATCT CATGCTGGAG TTCTTCGCCC ACCCCAACTT GTTTATTGCA 6900
                                        6885 6
GCTTATAATG GTTACAAATA AAGCAATAGC ATCACAAATT TCACAAATAA AGCATTTTTT 6360
                SV40 EARLY POLYADENYLATION REGION=133bp
TCACTGCATT CTAGTTGTGG TTTGTCCAAA CTCATCAATC TATCTTATCA TGTCTGGATC 7020
                                                        7018 9
LINKER #13=19bp
GCGGCCGCGA TCCCGTCGAG AGCTTGGCGT AATCATGGTC ATAGCTGTTT CCTGTGTGAA 7080
            7037 8
                    PUC 19
ATTGTTATCC GCTCACAATT CCACACAACA TACGAGCCGG AAGCATAAAG TGTAAAGCCT 7140

GGGGTGCCTA ATGAGTGAGC TAACTCACAT TAATTGCGTT GCGCTCACTG CCCGCTTTCC 7200

AGTCGGGAAA CCTGTCGTGC CAGCTGCATT AATGAATCGG CCAACGCGCG GGAGAGGCG 7260

GTTTGCGTAT TGGGCGCTCT TCCGCTTCCT CGCTCACTGA CTCGCTGCGC TCGGTCGTTC 7320

GGCTGCGGCG AGCGGTATCA GCTCACTCAA AGGCGGTAAT ACGGTTATCC ACAGAATCAG 7380

GGGATAACGC AGGAAAGAAC ATGTGAGCAA AAGGCCAGCA AAAGGCCAGG AACCGTAAAA 7440
                7461=BACTERIAL ORIGIN OF REPLICATION
AGGCCGCGTT GCTGGCGTTT TTCCATAGGC TCCGCCCCCC TGACGAGCAT CACAAAAATC 7500

*FIG. 3E*

```
GACGCTCAAG TCAGAGGTGG CGAAACCCGA CAGGACTATA AAGATACCAG GCGTTTCCCC 7560
CTGGAAGCTC CCTCGTGCGC TCTCCTGTTC CGACCCTGCC GCTTACCGGA TACCTGTCCG 7620
CCTTTCTCCC TTCGGGAAGC GTGGCGCTTT CTCAATGCTC ACGCTGTAGG TATCTCAGTT 7680
CGGTGTAGGT CGTTCGCTCC AAGCTGGGCT GTGTGCACGA ACCCCCCGTT CAGCCCGACC 7740
GCTGCGCCTT ATCCGGTAAC TATCGTCTTG AGTCCAACCC GGTAAGACAC GACTTATCGC 7800
CACTGGCAGC AGCCACTGGT AACAGGATTA GCAGAGCGAG GTATGTAGGC GGTGCTACAG 7860
AGTTCTTGAA GTGGTGGCCT AACTACGGCT ACACTAGAAG GACAGTATTT GGTATCTGCG 7920
CTCTGCTGAA GCCAGTTACC TTCGGAAAAA GAGTTGGTAG CTCTTGATCC GGCAAACAAA 7980
CCACCGCTGG TAGCGGTGGT TTTTTTGTTT GCAAGCAGCA GATTACGCGC AGAAAAAAAG 8040
GATCTCAAGA AGATCCTTTG ATCTTTTCTA CGGGGTCTGA CGCTCAGTGG AACGAAAACT 8100
CACGTTAAGG GATTTTGGTC ATGAGATTAT CAAAAAGGAT CTTCACCTAG ATCCTTTTAA 8160
                                                       STOP
ATTAAAAATG AAGTTTTAAA TCAATCTAAA GTATATATGA GTAAACTTGG TCTGACAGTT 8220
BETA LACTAMASE
ACCAATGCTT AATCAGTGAG GCACCTATCT CAGCGATCTG TCTATTTCGT TCATCCATAG 8280
TTGCCTGACT CCCCGTCGTG TAGATAACTA CGATACGGGA GGGCTTACCA TCTGGCCCCA 8340
GTGCTGCAAT GATACCGCGA GACCCACGCT CACCGGCTCC AGATTTATCA GCAATAAACC 8400
          BETA LACTAMASE=861bp=286 AMINO ACID & STOP CODON
AGCCAGCCGG AAGGGCCGAG CGCAGAAGTG GTCCTGCAAC TTTATCCGCC TCCATCCAGT 8460
CTATTAATTG TTGCCGGGAA GCTAGAGTAA GTAGTTCGCC AGTTAATAGT TTGCGCAACG 8520
TTGTTGCCAT TGCTACAGGC ATCGTGGTGT CACGCTCGTC GTTTGGTATG GCTTCATTCA 8580
GCTCCGGTTC CCAACGATCA AGGCGAGTTA CATGATCCCC CATGTTGTGC AAAAAAGCGG 8640
TTAGCTCCTT CGGTCCTCCG ATCGTTGTCA GAAGTAAGTT GGCCGCAGTG TTATCACTCA 8700
TGGTTATGGC AGCACTGCAT AATTCTCTTA CTGTCATGCC ATCCGTAAGA TGCTTTTCTG 8760
TGACTGGTGA GTACTCAACC AAGTCATTCT GAGAATAGTG TATGCGGCGA CCGAGTTGCT 8820
CTTGCCCGGC GTCAATACGG GATAATACCG CGCCACATAG CAGAACTTTA AAAGTGCTCA 8880
TCATTGGAAA ACGTTCTTCG GGGCGAAAAC TCTCAAGGAT CTTACCGCTG TTGAGATCCA 8940
GGTCGATGTA ACCCACTCGT GCACCCAACT GATCTTCAGC ATCTTTTACT TTCACCAGCG 9000
TTTCTGGGTG AGCAAAAACA GGAAGGCAAA ATGCCGCAAA AAAGGGAATA AGGGCGACAC 9060
                 ┌─── START BETA LACTAMASE
GGAAATGTTG AATACTCATA CTCTTCCTTT TTCAATATTA TTGAAGCATT TATCAGGGTT 9120
ATTGTCTCAT GAGCGGATAC ATATTTGAAT GTATTTAGAA AAATAAACAA ATAGGGGTTC 9180
CGCGCACATT TCCCCGAAAA GTGCCACCT
```

FIG. 3F

LEADER

```
              -20                    -15              -10
FRAME 1  Met Asp Phe Gln Val Gln Ile Ile Ser Phe Leu Leu Ile Ser Ala Ser Val
         ATG GAT TTT CAG GTG CAG ATT ATC AGC TTC CTG CTA ATC AGT GCT TCA GTC
             987         996         1005        1014        1023

-5                    +1    FR1                        10
     Ile Met Ser Arg Gly  Gln Ile Val Leu Ser Gln Ser Pro Ala Ile Leu Ser Ala Ser
     ATA ATG TCC AGA GGA  CAA ATT GTT CTC TCC CAG TCT CCA GCA ATC CTG TCT GCA TCT
             1038         1047        1056        1065        1074        1083

20              23  24   CDR1       27/ 29  30              34
     Pro Gly Glu Lys Val Thr Met Thr Cys Arg Ala Ser Ser Ser Val Ser Tyr Ile His
     CCA GGG GAG AAG GTC ACA ATG ACT TGC AGG GCC AGC TCA AGT GTA AGT TAC ATC CAC
             1095        1104        1113        1122        1131        1140

35   FR2              40                   45                  49  50    CDR2
     Trp Phe Gln Gln Lys Pro Gly Ser Ser Pro Lys Pro Trp Ile Tyr Ala Thr Ser Asn
     TGG TTC CAG CAG AAG CCA GGA TCC TCC CCC AAA CCC TGG ATT TAT GCC ACA TCC AAC
             1152        1161        1170        1179        1188        1197

55  56  57          60      FR3      65                      70
     Leu Ala Ser Gly Val Pro Val Arg Phe Ser Gly Ser Gly Ser Gly Thr Ser Tyr Ser
     CTG GCT TCT GGA GTC CCT GTT CGC TTC AGT GGC AGT GGG TCT GGG ACT TCT TAC TCT
             1209        1218        1227        1236        1245        1254

75                  80                  85          88  89  90
     Leu Thr Ile Ser Arg Val Glu Ala Glu Asp Ala Ala Thr Tyr Tyr Cys Gln Gln Trp
     CTC ACC ATC AGC AGA GTG GAG GCT GAA GAT GCT GCC ACT TAT TAC TGC CAG CAG TGG
             1266        1275        1284        1293        1302        1311

CDR3  95      97  98     100   FR4      105     107
     Thr Ser Asn Pro Pro Thr Phe Gly Gly Gly Thr Lys Leu Glu Ile Lys
     ACT AGT AAC CCA CCC ACG TTC GGA GGG GGG ACC AAG CTG GAA ATC AAA
             1323        1332        1341        1350        1359
```

*FIG. 4*

LEADER

```
          -19                    -15                      -10                         -5
FRAME 1   Met Gly Trp Ser Leu  Ile Leu  Leu Phe Leu   Val Ala Val   Ala Thr Arg  Val
          ATG GGT TGG AGC CTC  ATC TTG  CTC TTC CTT   GTC GCT GTT   GCT ACG CGT  CTC
                       2409        2418        2427        2436        2445

-1  +1    FR1                                     10                    15
          Leu Ser  Gln Val Gln Leu   Gln Gln Pro Gly    Ala Glu Leu Val Lys   Pro Gly Ala Ser
          CTG TCC  CAG GTA CAA CTG   CAG CAG CCT GGG    GCT GAG CTG GTG AAG   CCT GGG GCC TCA
                       2460        2469        2478         2487        2496       2505

20                        25                      30  31   CDR1        35   36
          Val Lys Met Ser Cys Lys   Ala Ser Gly Tyr Thr Phe Thr   Ser Tyr Asn Met His  Trp
          GTG AAG ATG TCC TGC AAG   GCT TCT GGC TAC ACA TTT ACC   AGT TAC AAT ATG CAC  TGG
                      2517        2526        2535        2544        2553        2562

40   FR2                      45               49  50    52 52A  53  54
          Val Lys Gln Thr Pro Gly  Arg Gly Leu Glu Trp Ile Gly    Ala Ile Tyr Pro Gly Asn
          GTA AAA CAG ACA CCT GGT  CGG GGC CTG GAA TGG ATT GGA    GCT ATT TAT CCC GGA AAT
                      2574        2583        2592        2601        2610        2619

55         CDR2     60                      65  66  FR3         70
          Gly Asp Thr Ser Tyr Asn  Gln Lys Phe Lys Gly  Lys Ala Thr Leu  Thr Ala Asp Lys
          GGT GAT ACT TCC TAC AAT  CAG AAG TTC AAA GGC  AAG GCC ACA TTG  ACT GCA GAC AAA
                      2631        2640        2649        2658        2667        2676

75               80    82   82A 82B 82C 83        85
          Ser Ser Ser Thr Ala Tyr  Met Gln Leu Ser Ser Leu Thr  Ser Glu Asp Ser Ala Val
          TCC TCC AGC ACA GCC TAC  ATG CAG CTC AGC AGC CTG ACA  TCT GAG GAC TCT GCG GTC
                      2688        2697        2706        2715        2724        2733

90              94  95    CDR3        100  100A 100B 100C 100D 101  102  103
          Tyr Tyr Cys Ala Arg  Ser Thr Tyr Tyr  Gly Gly Asp Trp Tyr Phe Asn Val  Trp Gly
          TAT TAC TGT GCA AGA  TCG ACT TAC TAC  GGC GGT GAC TGG TAC TTC AAT GTC  TGG GGC
                      2745        2754        2763        2772        2781         2790

105  FR4               110              113
          Ala Gly Thr Thr Val Thr Val Ser Ala
          GCA GGG ACC ACG GTC ACC GTC TCT GCA
                      2802        2811        2820
```

*FIG. 5* ically bind to such foreign microorganisms; and, eliminate/destroy such foreign microorganisms. Lymphocytes, amongst others, are critical to the immune system. Lymphocytes are produced in the thymus, spleen and bone marrow (adult) and represent about 30% of the total white blood cells present in the circulatory system of humans (adult). There are two major sub-populations of lymphocytes: T cells and B cells. T cells are responsible for cell mediated immunity, while B cells are responsible for antibody production (humoral immunity). However, T cells and B cells can be considered as interdependent—in a typical immune response, T cells are activated when the T cell receptor binds to fragments of an antigen that are bound to major histocompatability complex ("MHC") glycoproteins on the surface of an antigen presenting cell; such activation causes
EXPRESSION AND USE OF ANTI-CD20 ANTIBODIES

RELATED APPLICATIONS

This is a continuation of U.S. application Ser. No. 08/475,813, filed Jun. 7, 1995, now U.S. Pat. No. 6,682,734; which is a divisional of U.S. application Ser. No. 08/149,099, filed Nov. 3, 1993, now U.S. Pat. No. 5,736,137; which is a continuation-in-part of U.S. application Ser. No. 07/978,891, filed Nov. 13, 1992, now abandoned. This patent document is related to U.S. application Ser. No. 07/977,691, filed Nov. 13, 1992, now abandoned; and U.S. application Ser. No. 08/147,696, filed Nov. 3, 1993, now U.S. Pat. No. 5,648,267, both entitled "IMPAIRED DOMINANT SELECTABLE MARKER SEQUENCE AND INTRONIC INSERTION STRATEGIES FOR ENHANCEMENT OF EXPRESSION OF GENE PRODUCT AND EXPRESSION VECTOR SYSTEMS COMPRISING SAME." Related patent applications Ser. Nos. 07/978,891, 07/977,691, and 08/147,696 are incorporated herein by reference.

37 C.F.R. §1.74(d)/(e) COPYRIGHT NOTICE

A portion of the disclosure of this patent document contains material which is subject to copyright protection. The copyright owner does not object to the reproduction by anyone of the patent document or the patent disclosure, as it appears in the Patent and Trademark Office patent files or records, but otherwise reserves all copyright rights whatsoever.

A. FIELD OF THE INVENTION

The references to be discussed throughout this document are set forth merely for the information described therein prior to the filing dates of this document, and nothing herein is to be construed as an admission, either express or implied, that the references are "prior art" or that the inventors are not entitled to antedate such descriptions by virtue of prior inventions or priority based on earlier filed applications.

The present invention is directed to the treatment of B cell lymphoma using chimeric and radiolabeled antibodies to the B cell surface antigen Bp35 ("CD20").

B. BACKGROUND OF THE INVENTION

The immune system of vertebrates (for example, primates, which include humans, apes, monkeys, etc.) consists of a number of organs and cell types which have evolved to: accurately and specifically recognize foreign microorganisms ("antigen") which invade the vertebrate-host; specifirelease of biological mediators ("interleukins") which, in essence, stimulate B cells to differentiate and produce antibody ("immunoglobulins") against the antigen.

Each B cell within the host expresses a different antibody on its surface thus, one B cell will express antibody specific for one antigen, while another B cell will express antibody specific for a different antigen. Accordingly, B cells are quite diverse, and this diversity is critical to the immune system. In humans, each B cell can produce an enormous number of antibody molecules (ie about $10^7$ to $10^8$). Such antibody production most typically ceases (or substantially decreases) when the foreign antigen has been neutralized. Occasionally, however, proliferation of a particular B cell will continue unabated; such proliferation can result in a cancer referred to as "B cell lymphoma."

T cells and B cells both comprise cell surface proteins which can be utilized as "markers" for differentiation and identification. One such human B cell marker is the human B lymphocyte-restricted differentiation antigen Bp35, referred to as "CD20." CD20 is expressed during early pre-B cell development and remains until plasma cell differentiation. Specifically, the CD20 molecule may regulate a step in the activation process which is required for cell cycle initiation and differentiation and is usually expressed at very high levels on neoplastic ("tumor") B cells. CD20, by definition, is present on both "normal" B cells as well as "malignant" B cells, ie those B cells whose unabated proliferation can lead to B cell lymphoma. Thus, the CD20 surface antigen has the potential of serving as a candidate for "targeting" of B cell lymphomas.

In essence, such targeting can be generalized as follows: antibodies specific to the CD20 surface antigen of B cells are, eg injected into a patient. These anti-CD20 antibodies specifically bind to the CD20 cell surface antigen of (ostensibly) both normal and malignant B cells; the anti-CD20 antibody bound to the CD20 surface antigen may lead to the destruction and depletion of neoplastic B cells. Additionally, chemical agents or radioactive labels having the potential to destroy the tumor can be conjugated to the anti-CD20 antibody such that the agent is specifically "delivered" to, eg, the neoplastic B cells. Irrespective of the approach, a primary goal is to destroy the tumor: the specific approach can be determined by the particular anti-CD20 antibody which is utilized and, thus, the available approaches to targeting the CD20 antigen can vary considerably.

For example, attempts at such targeting of CD20 surface antigen have been reported. Murine (mouse) monoclonal antibody 1F5 (an anti-CD20 antibody) was reportedly administered by continuous intravenous infusion to B cell lymphoma patients. Extremely high levels (>2 grams) of 1F5 were reportedly required to deplete circulating tumor cells, and the results were described as being "transient." Press et al., "Monoclonal Antibody 1F5 (Anti-CD20) Serotherapy of Human B-Cell Lymphomas." *Blood* 69/2:584-591 (1987). A potential problem with this approach is that non-human monoclonal antibodies (eg, murine monoclonal antibodies) typically lack human effector functionality, ie they are unable to, inter alia, mediate complement dependent lysis or lyse human target cells through antibody dependent cellular toxicity or Fc-receptor mediated phagocytosis. Furthermore, non-human monoclonal antibodies can be recognized by the human host as a foreign protein; therefore, repeated injections of such foreign antibodies can lead to the induction of immune responses leading to harmful hypersensitivity reactions. For murine-based monoclonal antibodies, this is often referred to as a Human Anti-Mouse Antibody response, or "HAMA" response. Additionally, these "foreign" antibodies can be attacked by the immune system of the host such that they are, in effect, neutralized before they reach their target site.

Lymphocytes and lymphoma cells are inherently sensitive to radiotherapy for several reasons: the local emission of ionizing radiation of radiolabeled antibodies may kill cells with or without the target antigen (eg, CD20) in close proximity to antibody bound to the antigen; penetrating radiation may obviate the problem of limited access to the antibody in bulky or poorly vascularized tumors; and, the total amount of antibody required may be reduced. The radionuclide emits radioactive particles which can damage cellular DNA to the point where the cellular repair mechanisms are unable to allow the cell to continue living; therefore, if the target cells are tumors, the radioactive label beneficially kills the tumor cells. Radiolabeled antibodies, by definition, include the use of a radioactive substance which may require the need for precautions for both the patient (ie possible bone marrow transplantation) as well as the health care provider (ie the need to exercise a high degree of caution when working with the radioactivity).

Therefore, an approach at improving the ability of murine monoclonal antibodies to be effective in the treatment of B-cell disorders has been to conjugate a radioactive label or toxin to the antibody such that the label or toxin is localized at the tumor site. For example, the above-referenced IF5 antibody has been "labeled" with iodine-131 ("$^{131}$I") and was reportedly evaluated for biodistribution in two patients. See Eary, J. F. et al., "Imaging and Treatment of B-Cell Lymphoma" *J. Nuc. Med.* 31/8:1257-1268 (1990); see also, Press, O. W. et al., "Treatment of Refractory Non-Hodgkin's Lymphoma with Radiolabeled MB-1 (Anti-CD37) Antibody" *J. Clin. Onc.* 7/8:1027-1038 (1989) (indication that one patient treated with $^{131}$I-labeled IF-5 achieved a "partial response"); Goldenberg, D. M. et al., "Targeting, Dosimetry and Radioimmunotherapy of B-Cell Lymphomas with Iodine-131-Labeled LL2 Monoclonal Antibody" *J. Clin. Onc.* 9/4:548-564 (1991) (three of eight patients receiving multiple injections reported to have developed a HAMA response); Appelbaum, F. R. "Radiolabeled Monoclonal Antibodies in the Treatment of Non-Hodgkin's Lymphoma" *Hem./Onc. Clinics of N.A.* 5/5:1013-1025 (1991) (review article); Press, O. W. et al "Radiolabeled-Antibody Therapy of B-Cell Lymphoma with Autologous Bone Marrow Support." *New England Journal of Medicine* 329/17: 1219-12223 (1993) (iodine-131 labeled anti-CD20 antibody IF5 and B1); and Kaminski, M. G. et al "Radioimmunotherapy of B-Cell Lymphoma with [$^{131}$I] Anti-B1 (Anti-CD20) Antibody". *NEJM* 329/7(1993) (iodine-131 labeled anti-CD20 antibody B1; hereinafter "Kaminski").

Toxins (ie chemotherapeutic agents such as doxorubicin or mitomycin C) have also been conjugated to antibodies. See, for example, PCT published application WO 92/07466 (published May 14, 1992).

"Chimeric" antibodies, ie antibodies which comprise portions from two or more different species (eg, mouse and human) have been developed as an alternative to "conjugated" antibodies. For example, Liu, A. Y. et al., "Production of a Mouse-Human Chimeric Monoclonal Antibody to CD20 with Potent Fc-Dependent Biologic Activity" *J. Immun.* 139/10:3521-3526 (1987), describes a mouse/human chimeric antibody directed against the CD20 antigen. See also, PCT Publication No. WO 88/04936. However, no information is provided as to the ability, efficacy or practicality of using such chimeric antibodies for the treatment of B cell disorders in the reference. It is noted that in vitro functional assays (eg complement dependent lysis ("CDC"); antibody dependent cellular cytotoxicity ("ADCC"), etc.) cannot inherently predict the in vivo capability of a chimeric antibody to destroy or deplete target cells expressing the specific antigen. See, for example, Robinson, R. D. et al., "Chimeric mouse-human anti-carcinoma antibodies that mediate different anti-tumor cell biological activities," *Hum. Antibod. Hybridomas* 2:84-93 (1991) (chimeric mouse-human antibody having undetectable ADCC activity). Therefore, the potential therapeutic efficacy of chimeric antibody can only truly be assessed by in vivo experimentation.

What is needed, and what would be a great advance in the art, are therapeutic approaches targeting the CD20 antigen for the treatment of B cell lymphomas in primates, including, but not limited to, humans.

C. SUMMARY OF THE INVENTION

Disclosed herein are therapeutic methods designed for the treatment of B cell disorders, and in particular, B cell lymphomas. These protocols are based upon the administration of immunologically active chimeric anti-CD20 antibodies for the depletion of peripheral blood B cells, including B cells associated with lymphoma; administration of radiolabeled anti-CD20 antibodies for targeting localized and peripheral B cell associated tumors; and administration of chimeric anti-CD20 antibodies and radiolabeled anti-CD20 antibodies in a cooperative therapeutic strategy.

D. BRIEF DESCRIPTION OF THE DRAWINGS

FIGS. 2A through 2F are the nucleic acid sequence of the vector of FIG. 1 (also set forth as SEQ ID NO:1);

FIGS. 3A through 3F are the nucleic acid sequence of the vector of FIG. 1 further comprising murine light and heavy chain variable regions ("anti-CD20 in TCAE8") (also set forth as SEQ ID NO:2);

FIG. 4 shows the nucleic acid (SEQ ID NO:3) and amino acid (SEQ ID NO:4) sequences (including CDR and framework regions) of murine variable region light chain derived from murine anti-CD20 monoclonal antibody 2B8;

FIG. 5 shows the nucleic acid (SEQ ID NO:5) and amino acid (SEQ ID NO:6) sequences (including CDR and framework regions) of murine variable region heavy chain derived from murine anti-CD20 monoclonal antibody 2B8;

Figure 9A:
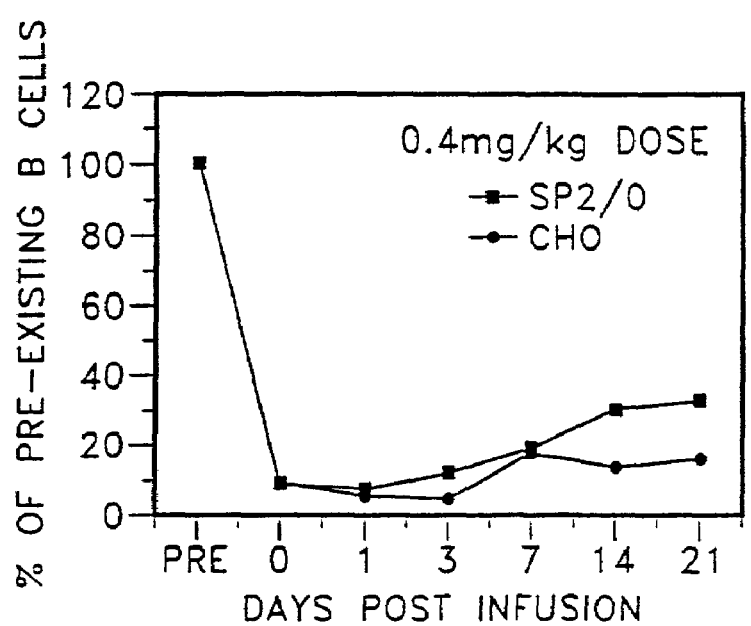
Figure 9B:
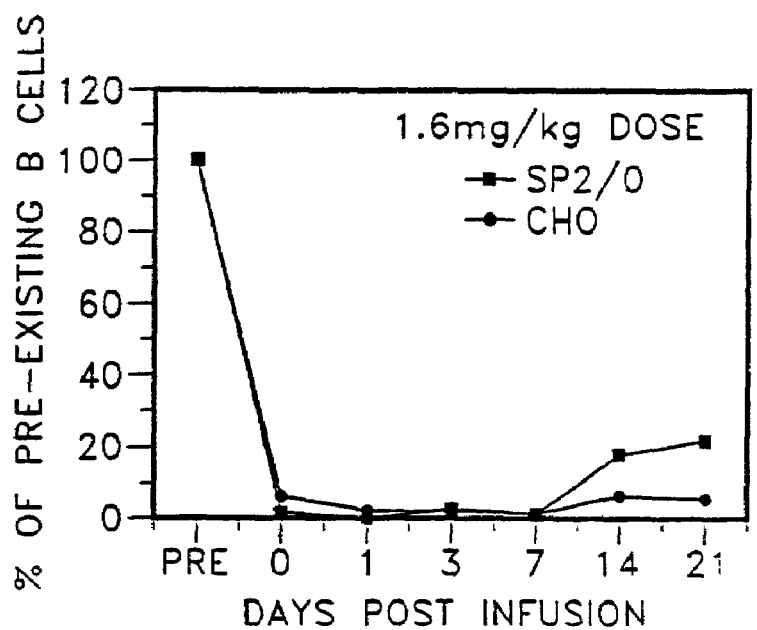
Figure 9C:
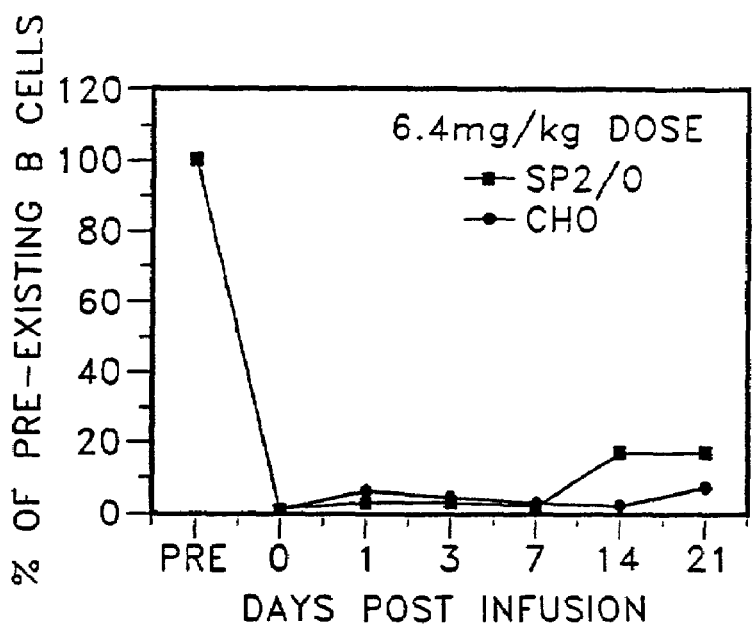
Figure 10:
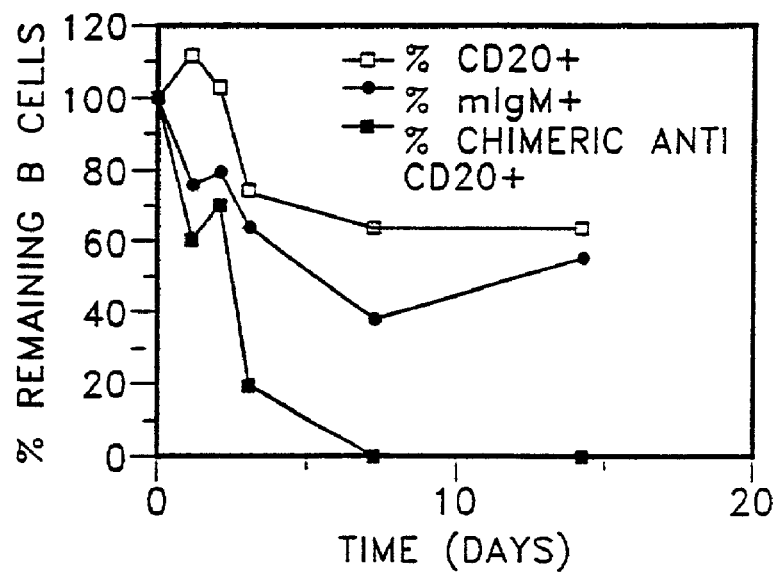
Figure 11:
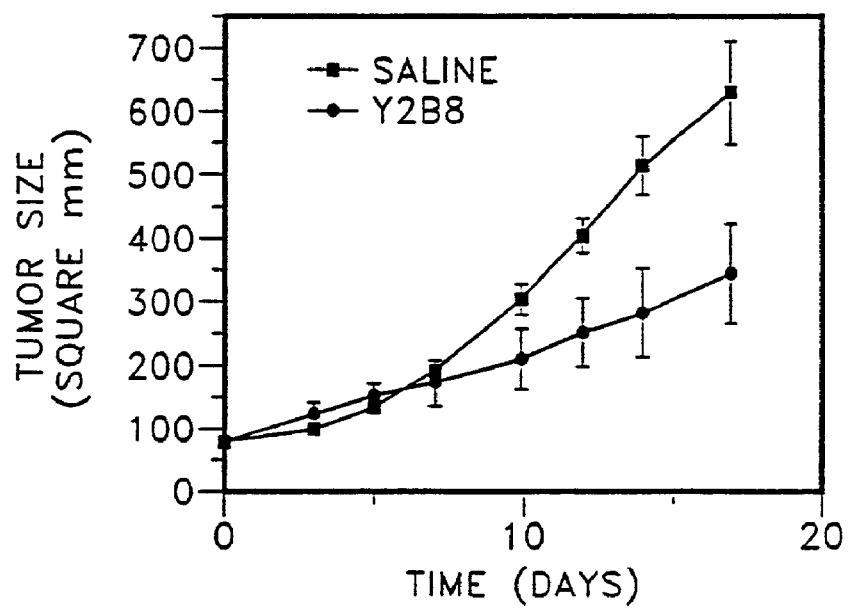
Figure 12:
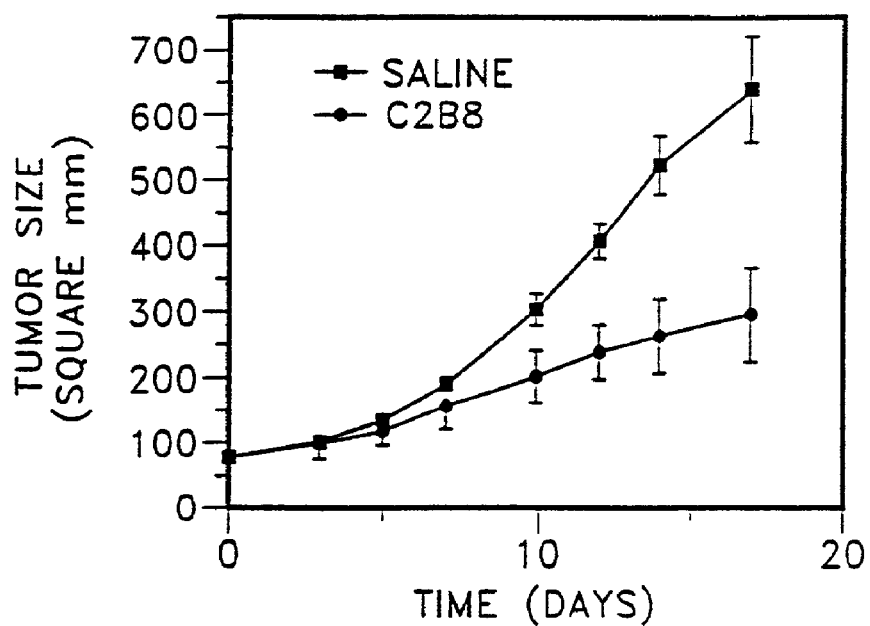
Figure 13:
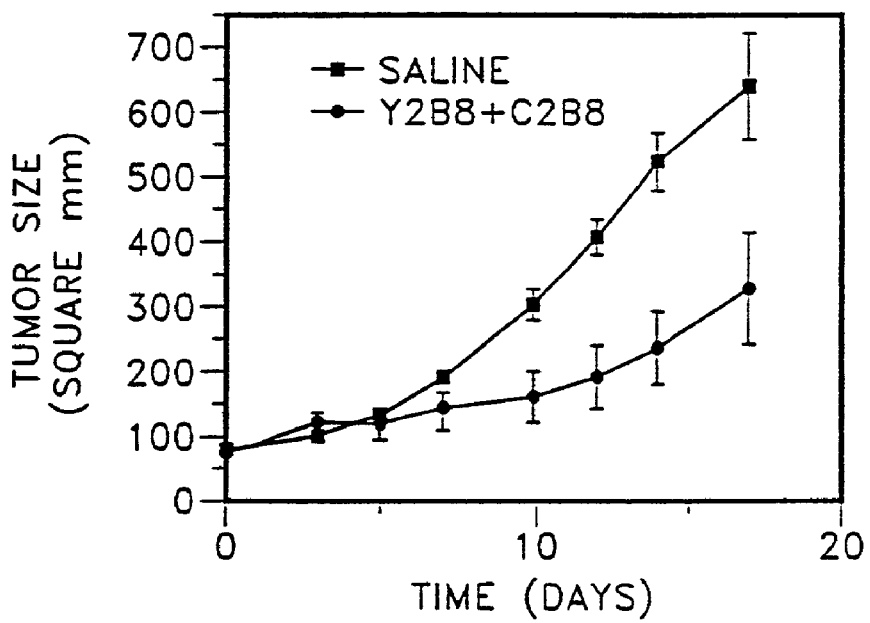
Figure 14A:
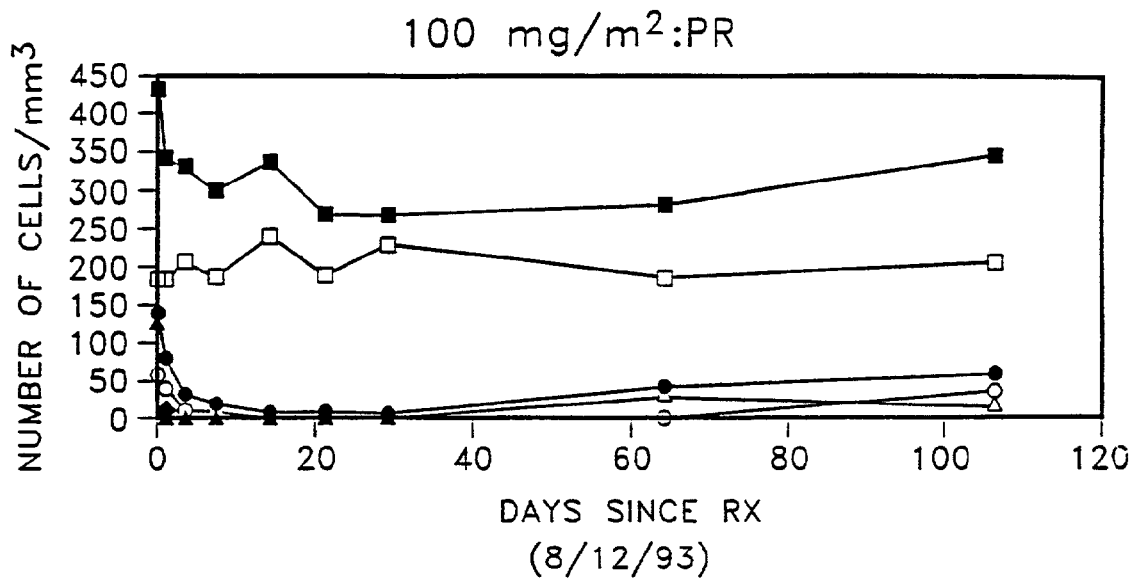
Figure 14B:
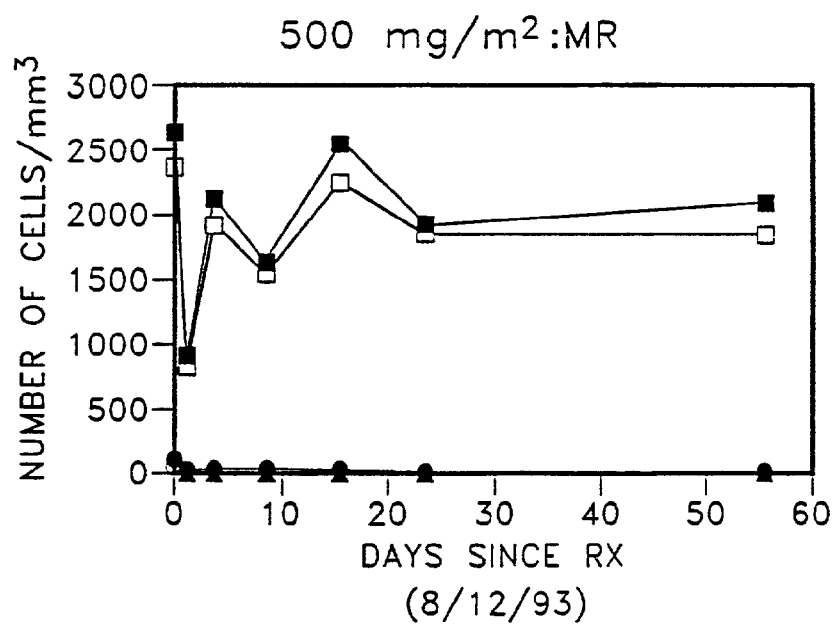

FIG. 9A, 9B and 9C provide the results of non-human primate peripheral blood B lymphocyte depletion after infusion of 0.4 mg/kg (A); 1.6 mg/kg (B); and 6.4 mg/kg (C) of immunologically active chimeric anti-CD20 antibody;

FIG. 10 provides the results of, inter alia, non-human primate peripheral blood B lymphocyte depletion after infusion of 0.01 mg/kg of immunologically active chimeric anti-CD20 antibody;

FIG. 11 provides results of the tumoricidal impact of Y2B8 in a mouse xenographic model utilizing a B cell lymphoblastic tumor;

FIG. 12 provides results of the tumoricidal impact of C2B8 in a mouse xenographic model utilizing a B cell lymphoblastic tumor;

FIG. 13 provides results of the tumoricidal impact of a combination of Y2B8 and C2B8 in a mouse xenographic model utilizing a B cell lymphoblastic tumor; and FIGS. 14A and 14B provide results from a Phase I/II clinical analysis of C2B8 evidencing B-cell population depletion over time for patients evidencing a partial remission of the disease (14A) and a minor remission of the disease (14B).

E. DETAILED DESCRIPTION OF PREFERRED EMBODIMENTS

Generally, antibodies are composed of two light chains and two heavy chain molecules; these chains form a general "Y" shape, with both light and heavy chains forming the arms of the Y and the heavy chains forming the base of the Y. Light and heavy chains are divided into domains of structural and functional homology. The variable domains of both the light ("$V_L$") and the heavy ("$V_H$") chains determine recognition and specificity. The constant region domains of light ("$C_L$") and heavy ("$C_H$") chains confer important biological properties, eg antibody chain association, secretion, transplacental mobility, Fc receptor binding complement binding, etc. The series of events leading to immunoglobulin gene expression in the antibody producing cells are complex. The variable domain region gene sequences are located in separate germ line gene segments referred to as "$V_H$," "D," and "$J_H$," or "$V_L$" and "$J_L$." These gene segments are joined by DNA rearrangements to form the complete V regions expressed in heavy and light chains, respectively. The rearranged, joined V segments ($V_L$-$J_L$ and $V_H$-D-$J_H$) then encode the complete variable regions or antigen binding domains of light and heavy chains, respectively.

Serotherapy of human B cell lymphomas using an anti-CD20 murine monoclonal antibody (1F5) has been described by Press et al., (69 Blood 584, 1987, supra); the reported therapeutic responses, unfortunately, were transient. Additionally, 25% of the tested patients reportedly developed a human anti-mouse antibody (HAMA) response to the serotherapy. Press et al., suggest that these antibodies, conjugated to toxins or radioisotopes, might afford a more lasting clinical benefit than the unconjugated antibody.

Owing to the debilitating effects of B cell lymphoma and the very real need to provide viable treatment approaches to this disease, we have embarked upon different approaches having a particular antibody, 2B8, as the common link between the approaches. One such approach advantageously exploits the ability of mammalian systems to readily and efficiently recover peripheral blood B cells; using this approach, we seek to, in essence, purge or deplete B cells in peripheral blood and lymphatic tissue as a means of also removing B cell lymphomas. We accomplish this by utilization of, inter alia, immunologically active, chimeric anti-CD20 antibodies. In another approach, we seek to target tumor cells for destruction with radioactive labels.

As used herein, the term "anti-CD20 antibody" is an antibody which specifically recognizes a cell surface non-glycosylated phosphoprotein of 35,000 Daltons, typically designated as the human B lymphocyte restricted differentiation antigen Bp35, commonly referred to as CD20. As used herein, the term "chimeric" when used in reference to anti-CD20 antibodies, encompasses antibodies which are most preferably derived using recombinant deoxyribonucleic acid techniques and which comprise both human (including immunologically "related" species, eg, chimpanzee) and non-human components: the constant region of the chimeric antibody is most preferably substantially identical to the constant region of a natural human antibody; the variable region of the chimeric antibody is most preferably derived from a non-human source and has the desired antigenic and specificity to the CD20 cell surface antigen. The non-human source can be any vertebrate source which can be used to generate antibodies to a human CD20 cell surface antigen or material comprising a human CD20 cell surface antigen. Such non-human source includes, but is not limited to, rodents (eg, rabbit, rat, mouse, etc.) and non-human primates (eg, Old World Monkey, Ape, etc.). Most preferably, the non-human component (variable region) is derived from a murine source. As used herein, the phrase "immunologically active" when used in reference to chimeric anti-CD20 antibodies, means a chimeric antibody which binds human C1q, mediates complement dependent lysis ("CDC") of human B lymphoid cell lines, and lyses human target cells through antibody dependent cellular cytotoxicity ("ADCC"). As used herein, the phrases "indirect labeling" and "indirect labeling approach" both mean that a chelating agent is covalently attached to an antibody and at least one radionuclide is inserted into the chelating agent. Preferred chelating agents and radionuclides are set forth in Srivagtava, S. C. and Mease, R. C.,"Progress in Research on Ligands, Nuclides and Techniques for Labeling Monoclonal Antibodies," Nucl. Med. Bio. 18/6: 589-603 (1991) ("Srivagtava") which is incorporated herein by reference. A particularly preferred chelating agent is 1-isothiocycmatobenzyl-3-methyldiothelene triaminepent acetic acid ("MX-DTPA"); particularly preferred radionuclides for indirect labeling include indium [111] and yttrium [90]. As used herein, the phrases "direct labeling" and "direct labeling approach" both mean that a radionuclide is covalently attached directly to an antibody (typically via an amino acid residue). Preferred radionuclides are provided in Srivagtava; a particularly preferred radionuclide for direct labeling is iodine [131] covalently attached via tyrosine residues. The indirect labeling approach is particularly preferred.

The therapeutic approaches disclosed herein are based upon the ability of the immune system of primates to rapidly recover, or rejuvenate, peripheral blood B cells. Additionally, because the principal immune response of primates is occasioned by T cells, when the immune system has a peripheral blood B cell deficiency, the need for "extraordinary" precautions (ie patient isolation, etc.) is not necessary. As a result of these and other nuances of the immune systems of primates, our therapeutic approach to B cell disorders allows for the purging of peripheral blood B cells using immunologically active chimeric anti-CD20 antibodies.

Because peripheral blood B cell disorders, by definition, can indicate a necessity for access to the blood for treatment, the route of administration of the immunologically active chimeric anti-CD20 antibodies and radioalabeled anti-CD20 antibodies is preferably parenteral; as used herein, the term "parenteral" includes intravenous, intramuscular, subcutaneous, rectal, vaginal or intraperitoneal administration. Of these, intravenous administration is most preferred.

The immunologically active chimeric anti-CD20 antibodies and radiolabeled anti-CD20 antibodies will typically be provided by standard technique within a pharmaceutically acceptable buffer, for example, sterile saline, sterile buffered water, propylene glycol, combinations of the foregoing, etc. Methods for preparing parenteraly administerable agents are described in *Pharmaceutical Carriers & Formulations*, Martin, Remington's Pharmaceutical Sciences, 15th Ed. (Mack Pub. Co., Easton, Pa. 1975), which is incorporated herein by reference.

The specific, therapeutically effective amount of immunologically active chimeric anti-CD20 antibodies useful to produce a unique therapeutic effect in any given patient can be determined by standard techniques well known to those of ordinary skill in the art.

Effective dosages (ie therapeutically effective amounts) of the immunologically active chimeric anti-CD20 antibodies range from about 0.001 to about 30 mg/kg body weight, more preferably from about 0.01 to about 25 mg/kg body weight, and most preferably from about 0.4 to about 20.0 mg/kg body weight. Other dosages are viable; factors influencing dosage include, but are not limited to, the severity of the disease; previous treatment approaches; overall health of the patient; other diseases present, etc. The skilled artisan is readily credited with assessing a particular patient and determining a suitable dosage that falls within the ranges, or if necessary, outside of the ranges.

Introduction of the immunologically active chimeric anti-CD20 antibodies in these dose ranges can be carried out as a single treatment or over a series of treatments. With respect to chimeric antibodies, it is preferred that such introduction be carried out over a series of treatments; this preferred approach is predicated upon the treatment methodology associated with this disease. While not wishing to be bound by any particular theory, because the immunologically active chimeric anti-CD20 antibodies are both immunologically active and bind to CD20, upon initial introduction of the immunologically active chimeric anti-CD20 antibodies to the individual, peripheral blood B cell depletion will begin; we have observed a nearly complete depletion within about 24 hours post treatment infusion. Because of this, subsequent introduction(s) of the immunologically active chimeric anti-CD20 antibodies (or radiolabeled anti-CD20 antibodies) to the patient is presumed to: a) clear remaining peripheral blood B cells; b) begin B cell depletion from lymph nodes; c) begin B cell depletion from other tissue sources, eg, bone marrow, tumor, etc. Stated again, by using repeated introductions of the immunologically active chimeric anti-CD20 antibodies, a series of events take place, each event being viewed by us as important to effective treatment of the disease, The first "event" then, can be viewed as principally directed to substantially depleting the patient's peripheral blood B cells; the subsequent "events" can be viewed as either principally directed to simultaneously or serially clearing remaining B cells from the system clearing lymph node B cells, or clearing other tissue B cells.

In effect, while a single dosage provides benefits and can be effectively utilized for disease treatment/management, a preferred treatment course can occur over several stages; most preferably, between about 0.4 and about 20 mg/kg body weight of the immunologically active chimeric anti-CD20 antibodies is introduced to the patient once a week for between about 2 to 10 weeks, most preferably for about 4 weeks.

With reference to the use of radiolabeled anti-CD20 antibodies, a preference is that the antibody is non-chimeric; this preference is predicated upon the significantly longer circulating half-life of chimeric antibodies vis-a-vis murine antibodies (ie, with a longer circulating half-life, the radionuclide is present in the patient for extended periods). However, radiolabeled chimeric antibodies can be beneficially utilized with lower millicurie ("mCi") dosages used in conjunction with the chimeric antibody relative to the murine antibody. This scenario allows for a decrease in bone marrow toxicity to an acceptable level, while maintaining therapeutic utility.

A variety of radionuclides are applicable to the present invention and those skilled in the art are credited with the ability to readily determine which radionuclide is most appropriate under a variety of circumstances. For example, iodine [131] is a well known radionuclide used for targeted immunotherapy. However, the clinical usefulness of iodine [131] can be limited by several factors including: eight-day physical half-life; dehalogenation of iodinated antibody both in the blood and at tumor sites; and emission characteristics (eg large gamma component) which can be suboptimal for localized dose deposition in tumor. With the advent of superior chelating agents, the opportunity for attaching metal chelating groups to proteins has increased the opportunities to utilize other radionuclides such as indium [131] and yttrium [90]. Yttrium [90] provides several benefits for utilization in radioimmunotherapeutic applications: the 64 hour half-life of yttrium [90] is long enough to allow antibody accumulation by tumor and, unlike eg iodine [131], yttrium [90] is a pure beta emitter of high energy with no accompanying gamma irradiation in its decay, with a range in tissue of 100 to 1000 cell diameters. Furthermore, the minimal amount of penetrating radiation allows for outpatient administration of yttrium [90]-labeled antibodies. Furthermore, interalization of labeled antibody is not required for cell killing, and the local emission of ionizing radiation should be lethal for adjacent tumor cells lacking the target antigen.

One non-therapeutic limitation to yttrium [90] is based upon the absence of significant gamma radiation making imaging therewith difficult. To avoid this problem, a diagnostic "imaging" radionuclide, such as indium [111], can be utilized for determining the location and relative size of a tumor prior to the administration of therapeutic does of yttrium [90]-labeled anti-CD20. Indium [111] is particularly preferred as the diagnostic radionuclide because: between about 1 to about 10 mCi can be safely administered without detectable toxicity; and the imaging data is generally predictive of subsequent yttrium [90]-labeled antibody distribution. Most imaging studies utilize 5 mCi indium [111]-labeled antibody because this dose is both safe and has increased imaging efficiency compared with lower doses, with optimal imaging occurring at three to six days after antibody administration. See, for example, Murray J. L. , 26 *J. Nuc. Med.* 3328 (1985) and Carraguillo, J. A. et al, 26 *J. Nuc. Med.* 67 (1985).

Effective single treatment dosages (ie therapeutically effective amounts) of yttrium [90] labeled anti-CD20 antibodies range from between about 5 and about 75 mCi, more preferably between about 10 and about 40 mCi. Effective single treatment non-marrow ablative dosages of iodine [131] labeled anti-CD20 antibodies range from between about 5 and about 70 mCi, more preferably between about 5 and about 40 mCi. Effective single treatment ablative dosages (ie may require autologous bone marrow transplantation) of iodine [131] labeled anti-CD20 antibodies range from between about 30 and about 600 mCi, more preferably between about 50 and less than about 500 mCi. In conjunction with a chimeric anti-CD20 antibody, owing to the longer circulating half life vis-a-vis murine antibodies, an effective single treatment non-marrow ablative dosages of iodine [131] labeled chimeric anti-CD20 antibodies range from between about 5 and about 40 mCi, more preferably less than about 30 mCi. Imaging criteria for, eg the indium [111] label, are typically less than about 5 mCi.

With respect to radiolabeled anti-CD20 antibodies, therapy therewith can also occur using a single therapy treatment or using multiple treatments. Because of the radionuclide component, it is preferred that prior to treatment, peripheral stem cells ("PSC") or bone marrow ("BM") be "harvested" for patients experiencing potentially fatal bone marrow toxicity resulting from radiation. BM and/or PSC are harvested using standard techniques, and then purged and frozen for possible reinfusion. Additionally, it is most preferred that prior to treatment a diagnostic dosimetry study using a diagnostic labeled antibody (eg using indium [111]) be conducted on the patient, a purpose of which is to ensure that the therapeutically labeled antibody (eg using yttrium [90]) will not become unnecessarily "concentrated" in any normal organ or tissue.

Chimeric mouse/human antibodies have been described. See, for example, Morrison, S. L. et al., *PNAS* I1:6851-6854 (November 1984); European Patent Publication No. 173494; Boulianne, G. L, et al., *Nature* 312:643 (December 1984); Neubeiger, M. S. et al., *Nature* 314:268 (March 1985); European Patent Publication No. 125023; Tan et al., *J. Immunol.* 135:8564 (November 1985); Sun, L. K et al., *Hybridoma* 5/1:517 (1986); Sahagan et al., *J. Immunol.* 137:1066-1074 (1986). See generally, Muron, *Nature* 312: 597 (December 1984); Dickson, *Genetic Engineering News* 5/3 (March 1985); Marx, *Science* 229 455 (August 1985); and Morrison *Science* 229:1202-1207 (September 1985). Robinson et al., in PCT Publication Number WO 88/04936 describe a chimeric antibody with human constant region and murine variable region, having specificity to an epitope of CD20; the murine portion of the chimeric antibody of the Robinson references is derived from the 2H7 mouse monoclonal antibody (gamma 2b, kappa). While the reference notes that the described chimeric antibody is a "prime candidate" for the treatment of B cell disorders, this statement can be viewed as no more than a suggestion to those in the art to determine whether or not this suggestion is accurate for this particular antibody, particularly because the reference lacks any data to support an assertion of therapeutic effectiveness, and importantly, data using higher order mammals such as primates or humans.

Methodologies for generating chimeric antibodies are available to those in the art. For example, the light and heavy chains can be expressed separately, using, for example, immunoglobulin light chain and immunoglobulin heavy chains in separate plasmids. These can then be purified and assembled in vitro into complete antibodies; methodologies for accomplishing such assembly have been described. See, for example, Scharff, M., *Harvey Lectures* 69:125 (1974). In vitro reaction parameters for the formation of IgG antibodies from reduced isolated light and heavy chains have also been described. See, for example, Beychok, S., *Cells of Immunoglobulin Synthesis*, Academic Press, New York, p. 69, 1979. Co-expression of light and heavy chains in the same cells to achieve intracellular association and linkage of heavy and light chains into complete $H_2L_2$ IgG antibodies is also possible. Such co-expression can be accomplished using either the same or different plasmids in the same host cell.

Another approach, and one which is our most preferred approach for developing a chimeric non-human/human anti-CD20 antibody, is based upon utilization of an expression vector which includes, ab initio, DNA encoding heavy and light chain constant regions from a human source. Such a vector allows for inserting DNA encoding non-human variable regions such that a variety of non-human anti-CD20 antibodies can be generated, screened and analyzed for various characteristics (eg type of binding specificity, epitope binding regions, etc.); thereafter, cDNA encoding the light and heavy chain variable regions from a preferred or desired anti-CD20 antibody can be incorporated into the vector. We refer to these types of vectors as Tandem Chimeric Antibody Expression ("TCAE") vectors. A most preferred TCAE vector which was used to generate immunologically active chimeric anti-CD20 antibodies for therapeutic treatment of lymphomas is TCAE 8. TCAE 8 is a derivative of a vector owned by the assignee of this patent document, referred to as TCAE 5.2, the difference being that in TCAE 5.2, the translation initiation start site of the dominant selectable marker (neomycin phosphostransferase, "NEO") is a consensus Kozak sequence, while for TCAE 8, this region is a partially impaired consensus Kozak sequence. Details regarding the impact of the initiation start site of the dominant selectable marker of the TCAE vectors (also referred to as "ANEX vector") vis-a-vis protein expression are disclosed in detail in application Ser. No. 08/147,696, now U.S. Pat. No. 5,648,267, filed herewith.

TCAE 8 comprises four (4) transcriptional cassettes, and these are in tandem order, ie a human immunoglobulin light chain absent a variable region; a human immunoglobulin heavy chain absent a variable region; DHFR; and NEO. Each transcriptional cassette contains its own eukaryotic promoter and polyadenylation region (reference is made to FIG. 1 which is a diagrammatic representation of the TCAE 8 vector). Specifically:

1) the CMV promoter/enhancer in front of the immunoglobulin heavy chain is a truncated version of the promoter/enhancer in front of the light chain, from the Nhe I site at −350 to the Sst I site at −16 (see, 41 *Cell* 521, 1985).

2) a human immunoglobulin light chain constant region was derived via amplification of cDNA by a PCR reaction. In TCAE 8, this was the human immunoglobulin light chain kappa constant region (Kabat numbering, amino acids 108-214, allotype Km 3, (see, Kabat, E. A. "Sequences of proteins of immunological interest," NIH Publication, Fifth Ed. No. 91-3242, 1991)), and the human immunoglobulin heavy chain gamma 1 constant region (Kabat numbering amino acids 114-478, allotype Gmla, Gmlz). The light chain was isolated from normal human blood (IDEC Pharmaceuticals Corporation, La Jolla, Calif.); RNA therefrom was used to synthesize cDNA which was then amplified using PCR techniques (primers were derived vis-a-vis the consensus from Kabat). The heavy chain was isolated (using PCR techniques) from cDNA prepared from RNA which was in turn derived from cells transfected with a human IgG1 vector (see, 3 *Prot. Eng.* 531, 1990; vector $pN_{\gamma 1}62$). Two amino acids were changed in the isolated human IgG1 to match the consensus amino acid sequence from Kabat, to wit: amino acid 225 was changed from valine to alanine (GTT to GCA), and amino acid 287 was changed from methionine to lysine (ATG to AAG);

3) The human immunoglobulin light and heavy chain cassettes contain synthetic signal sequences for secretion of the immunoglobulin chains;

4) The human immunoglobulin light and heavy chain cassettes contain specific DNA restriction sites which allow for insertion of light and heavy immunoglobulin variable regions which maintain the transitional reading frame and do not alter the amino acids normally found in immunoglobulin chains;

5) The DHFR cassette contained its own eukaryotic promoter (mouse beta globin major promoter, "BETA") and polyadenylation region (bovine growth hormone polyadenylation, "BGH"); and 6) The NEO cassette contained its own eukaryotic promoter (BETA) and polyadenylation region (SV40 early polyadenylation, "SV").

With respect to the TCAE 8 vector and the NEO cassette, the Kozak region was a partially impaired consensus Kozak sequence (which included an upstream Cla I site):

```
          (SEQ ID NO:7)
                ClaI     -3     +1
          GGGAGCTTGG ATCGAT ccTct ATG Gtt
```

(In the TCAE 5.2 vector, the change is between the ClaI and ATG regions, to wit: ccAcc.)

The complete sequence listing of TCAE 8 (including the specific components of the four transcriptional cassettes) is set forth in FIG. 2 (SEQ. ID. NO. 1).

As will be appreciated by those in the art, the TCAE vectors beneficially allow for substantially reducing the time in generating the immunologically active chimeric anti-CD20 antibodies. Generation and isolation of non-human light and heavy chain variable regions, followed by incorporation thereof within the human light chain constant transcriptional cassette and human heavy chain constant transcriptional cassette, allows for production of immunologically active chimeric anti-CD20 antibodies.

We have derived a most preferred non-human variable region with specificity to the CD20 antigen using a murine source and hybridoma technology. Using polymerase chain reaction ("PCR") techniques, the murine light and heavy variable regions were cloned directly into the TCAE 8 vector—this is the most preferred route for incorporation of the non-human variable region into the TCAE vector. This preference is principally predicated upon the efficiency of the PCR reaction and the accuracy of insertion. However, other equivalent procedures for accomplishing this task are available. For example, using TCAE 8 (or an equivalent vector), the sequence of the variable region of a non-human anti-CD20 antibody can be obtained, followed by oligonucleotide synthesis of portions of the sequence or, if appropriate, the entire sequence; thereafter, the portions or the entire synthetic sequence can be inserted into the appropriate locations within the vector. Those skilled in the art are credited with the ability to accomplish this task.

Our most preferred immunologically active chimeric anti-CD20 antibodies were derived from utilization of TCAE 8 vector which included murine variable regions derived from monoclonal antibody to CD20; this antibody (to be discussed in detail, infra), is referred to as "2B8." The complete sequence of the variable regions obtained from 2B8 in TCAE 8 ("anti-CD20 in TCAE 8") is set forth in FIG. 3 (SEQ. ID. NO. 2).

The host cell line utilized for protein expression is most preferably of mammalian origin; those skilled in the art are credited with ability to preferentially determine particular host cell lines which are best suited for the desired gene product to be expressed therein. Exemplary host cell lines include, but are not limited to, DG44 and DUXB11 (Chinese Hamster Ovary lines, DHFR minus), HELA (human cervical carcinoma), CVI (monkey kidney line), COS (a derivative of CVI with SV40 T antigen), R1610 (Chinese hamster fibroblast) BALBC/3T3 (mouse fibroblast), HAK (hamster kidney line), SP2/O (mouse myeloma), P3x63-Ag3.653 (mouse myeloma), BFA-lclBPT (bovine endothelial cells), RAJI (human lymphocyte) and 293 (human kidney). Host cell lines are typically available from commercial services, the American Tissue Culture Collection or from published literature.

Preferably the host cell line is either DG44 ("CHO") or SP2/O. See Urland, G. et al., "Effect of gamma rays and the dihydrofolate reductase locus: deletions and inversions." *Som. Cell & Mol. Gen.* 12/6:555-566 (1986), and Shulman, M. et al., "A better cell line for making hybridomas secreting specific antibodies." *Nature* 276:269 (1978), respectively. Most preferably, the host cell line is DG44. Transfection of the plasmid into the host cell can be accomplished by any technique available to those in the art. These include, but are not limited to, transfection (including electrophoresis and electroporation), cell fusion with enveloped DNA, microinjection, and infection with intact virus. See, Ridgway, A. A. G. "Mammalian Expression Vectors." Chapter 24.2, pp. 470-472 *Vectors*, Rodriguez and Denhardt, Eds. (Butterworths, Boston, Mass. 1988). Most preferably, plasmid introduction into the host is via electroporation.

F. EXAMPLES

The following examples are not intended, nor are they to be construed, as limiting the invention. The examples are intended to evidence: dose-imaging using a radiolabeled anti-CD20 antibody ("I2B8"); radiolabeled anti-CD20 antibody ("Y2B8"); and immunologically active, chimeric anti-CD20 antibody ("C2B8") derived utilizing a specific vector ("TCAE 8") and variable regions derived from murine anti-CD20 monoclonal antibody ("2B8").

I. Radiolabeled Anti-CD20 Antibody 2B8

A. Anti-CD20 Monoclonal Antibody (Murine) Production ("2B8")

BALB/C mice were repeatedly immunized with the human lymphoblastoid cell line SB (see, Adams, R. A. et al., "Direct implantation and serial transplantation of human acute lymphoblastic leukemia in hamsters, SB-2." *Can Res* 28:1121-1125 (1968); this cell line is available from the American Tissue Culture Collection, Rockville, Md., under ATCC accession number ATCC CCL 120), with weekly injections over a period of 3-4 months. Mice evidencing high serum titers of anti-CD20 antibodies, as determined by inhibition of known CD20-specific antibodies (anti-CD20 antibodies utilized were Leu 16, Beckton Dickinson, San Jose, Calif., Cat. No. 7670; and Bl, Coulter Corp., Hialeah, Fla., Cat. No. 6602201) were identified; the spleens of such mice were then removed. Spleen cells were fused with the mouse myeloma SP2/0 in accordance with the protocol described in Einfeld, D. A. et al., (1988) *EMBO* 7:711 (SP2/0 has ATCC accession no. ATCC CRL 8006).

Assays for CD20 specificity were accomplished by radioimmunoassay. Briefly, purified anti-CD20 B1 was radiolabeled with $I^{125}$ by the iodobead method as described in Valentine, M. A. et al., (1989) *J. Biol. Chem.* 264:11282. ($I^{125}$ Sodium Iodide, ICN, Irvine, Calif., Cat. No. 28665H). Hybridomas were screened by co-incubation of 0.05 ml of media from each of the fusion wells together with 0.05 ml of $I^{125}$ labeled anti-CD20 B1 (10 ng) in 1% BSA, PBS (pH 7.4), and 0.5 ml of the same buffer containing 100,000 SB cells. After incubation for 1 hr at room temperature, the cells were harvested by transferring to 96 well titer plates (V&P Scientific, San Diego, Calif.), and washed thoroughly. Duplicate wells containing unlabeled anti-CD20 B1 and wells containing no inhibiting antibody were used as positive and negative controls, respectively. Wells containing greater than 50% inhibition were expanded and cloned. The antibody demonstrating the highest inhibition was derived from the cloned cell line designated herein as "2B8."

B. Preparation of 2B8-MX-DTPA Conjugate i. MX-DTPA

Carbon-14-labeled 1-isothiocyanatobenzyl-3-methyldiethylene triamminepentaacetic acid ("carbon-14 labeled MX-DTPA") was used as a chelating agent for conjugation of radiolabel to 2B8. Manipulations of MX-DTPA were conducted to maintain metal-free conditions, ie metal-free reagents were utilized and, when possible, polypropylene plastic containers (flasks, beakers, graduated cylinders, pipette tips) washed with ALCONOX detergent (Alconox, Inc.) and rinsed with MILLI-Q purified water (Millipore, Inc.), were similarly utilized. MX-DTPA was obtained as a dry solid from Dr. Otto Gansow (National Institute of Health, Bethesda, Md.) and stored desiccated at 4° C. (protected from light), with stock solutions being prepared in MILLI-Q water at a concentration of 2-5 mM, with storage at −70° C. MX-DTPA was also obtained from Coulter Immunology (Hialeah, Fla.) as the disodium salt in water and stored at −70° C.

ii. Preparation of 2B8

Purified 2B8 was prepared for conjugation with MX-DTPA by transferring the antibody into metal-free 50 mM bicine-NaOff, pH 8.6, containing 150 mM NaCl, using repetitive buffer exchange with CENTRICON 30™ spin filters (30,000 D, MWCO; Amicon). Generally, 50-200 µL of protein (10 mg/nl) was added to the filter unit, followed by 2 mL of bicine buffer. The filter was centrifuged at 4° C. in a Sorval SS-34 rotor (6,000 rpm, 45 min.). Retentate volume was approximately 50-100 µL; this process was repeated twice using the same filter. Retentate was transferred to a polypropylene 1.5 mL screw cap tube, assayed for protein, diluted to 10.0 mg/mL and stored at 4° C. until utilized; protein was similarly transferred into 50 mM sodium citrate, pH 5.5, containing 150 mM NaCl and 0.05% sodium azide, using the foregoing protocol.

iii. Conjugation of 2B8 with MX-DTPA

Conjugation of 2B8 with MX-DTPA was performed in polypropylene tubes at ambient temperature. Frozen MX-DTPA stock solutions were thawed immediately prior to use. 50-200 mL of protein at 10 mg/mL were reacted with MX-DTPA at a molar ratio of MX-DTPA-to-2B8 of 4:1. Reactions were initiated by adding the MX-DTPA stock solution and gently mixing; the conjugation was allowed to proceed overnight (14 to 20 hr), at ambient temperature. Unreacted MX-DTPA was removed from the conjugate by dialysis or repetitive ultrafiltration, as described above in Example I.B.ii, into metal-free normal saline (0.9% w/v) containing 0.05% sodium azide. The protein concentration was adjusted to 10 mg/mL and stored at 4° C. in a polypropylene tube until radiolabeled.

iv. Determination of Mx-DTPA Incorporation

MX-DTPA incorporation was determined by scintillation counting and comparing the value obtained with the purified conjugate to the specific activity of the carbon-[14]-labeled MX-DTPA. For certain studies, in which non-radioactive MX-DTPA (Coulter Immunology) was utilized, MX-DTPA incorporation was assessed by incubating the conjugate with an excess of a radioactive carrier solution of yttrium-[90] of known concentration and specific activity.

A stock solution of yttrium chloride of known concentration was prepared in metal-free 0.05 N HCl to which carrier-free yttrium-[90] (chloride salt) was added. An aliquot of this solution was analyzed by liquid scintillation counting to determine an accurate specific activity for this reagent. A volume of the yttrium chloride reagent equal to 3-times the number of mols of chelate expected to be attached to the antibody, (typically 2 mol/mol antibody), was added to a polypropylene tube, and the pH adjusted to 4.0-4.5 with 2 M sodium acetate. Conjugated antibody was subsequently added and the mixture incubated 15-30 min. at ambient temperature. The reaction was quenched by adding 20 mM EDTA to a final concentration of 1 mM and the pH of the solution adjusted to approximately pH 6 with 2M sodium acetate.

After a 5 min. incubation, the entire volume was purified by high-performance, size-exclusion chromatography (described infra). The eluted protein-containing fractions were combined, the protein concentration determined, and an aliquot assayed for radioactivity. The chelate incorporation was calculated using the specific activity of the yttrium-[90] chloride preparation and the protein concentration.

v. Immunoreactivity of 2B8-MX-DTPA

The immunoreactivity of conjugated 2B8 was assessed using whole-cell ELISA. Mid-log phase SB cells were harvested from culture by centrifugation and washed two times with 1× HBSS. Cells were diluted to 1-2×10$^6$ cells/mL in HBSS and aliquoted into 96-well polystyrene microtiter plates at 50,000-100,000 cells/well. The plates were dried under vacuum for 2 h. at 40-45° C. to fix the cells to the plastic; plates were stored dry at −20° C. until utilized. For assay. the plates were warmed to ambient temperature immediately before use, then blocked with 1× PBS, pH 7.2-7.4 containing 1% BSA (2 h). Samples for assay were diluted in 1× PBS/1% BSA, applied to plates and serially diluted (1:2) into the same buffer. After incubating plates for 1 h. at ambient temperature, the plates were washed three times with 1× PBS. Secondary antibody (goat anti-mouse IgG1-specific HRP conjugate 50 µL) was added to wells (1:1500 dilution in 1× PBS/1% BSA) and incubated 1 h. at ambient temperature. Plates were washed four times with 1× PBS followed by the addition of ABTS substrate solution (50 mM sodium citrate, pH 4.5 containing 0.01% ATBS and 0.001% $H_2O_2$). Plates were read at 405 nm after 15-30 min. incubation. Antigen-negative HSB cells were included in assays to monitor non-specific binding. Immunoreactivity of the conjugate was calculated by plotting the absorbance values vs. the respective dilution factor and comparing these to values obtained using native antibody (representing 100% immunoreactivity) tested on the same plate; several values on the linear portion of the titration profile were compared and a mean value determined (data not shown).

vi. Preparation of Indium-[111]-Labeled 2B8-MX-DTPA ("I2B8")

Conjugates were radiolabeled with carrier-free indium-[111]. An aliquot of isotope (0.1-2 mCi/mg antibody) in 0.05 M HCL was transferred to a polypropylene tube and approximately one-tenth volume of metal-free 2 M HCl added. After incubation for 5 min., metal-free 2 M sodium acetate was added to adjust the solution to pH 4.0-4.4. Approximately 0.5 mg of 2B8-MX-DTPA was added from a stock solution of 10.0 mg/mL DTPA in normal saline, or 50 mM sodium citrate/150 mM NaCl containing 0.05% sodium azide, and the solution gently mixed immediately. The pH solution was checked with pH paper to verify a value of 4.0-4.5 and the mixture incubated at ambient temperature for 15-30 min. Subsequently, the reaction was quenched by adding 20 mM EDTA to a final concentration of 1 mM and the reaction mixture was adjusted to approximately pH 6.0 using 2 M sodium acetate.

After a 5-10 min. incubation, uncomplexed radioisotope was removed by size-exclusion chromatography. The HPLC unit consisted of Waters Model 6000 or TosoHaas Model TSK-6110 solvent delivery system fitted, respectively, with a Waters U6K or Rheodyne 700 injection valve. Chromatographic separations were performed using a gel permeation column (BioRad SEC-250; 7.5×300 mm or comparable TosoHaas column) and a SEC-250 guard column (7.5×100 mm). The system was equipped with a fraction collector (Pharmacia Frac200) and a UV monitor fitted with a 280 nm filter (Pharmacia model UV-1). Samples were applied and eluted isocratically using 1× PBS, pH 7.4, at 1.0 mL/min flow rate. One-half milliliter fractions were collected in glass tubes and aliquots of these counted in a gamma counter. The lower and upper windows were set to 100 and 500 KeV respectively.

The radioincorporation was calculated by summing the radioactivity associated with the eluted protein peak and dividing this number by the total radioactivity eluted from the column; this value was then expressed as a percentage (data not shown). In some cases, the radioincorporation was determined using instant thin-layer chromatography ("ITLC"). Radiolabeled conjugate was diluted 1:10 or 1:20 in 1× PBS containing or 1× PBS/1 mM DTPA, then 1 µL was spotted 1.5 cm from one end of a 1×5 cm strip of ITLC SG paper. The paper was developed by ascending chromatography using 10% ammonium acetate in methanol:water (1:1;v/v). The strip was dried, cut in half crosswise, and the radioactivity associated with each section determined by gamma counting. The radioactivity associated with the bottom half of the strip (protein-associated radioactivity) was expressed as a percentage of the total radioactivity, determined by summing the values for both top and bottom halves (data not shown).

Specific activities were determined by measuring the radioactivity of an appropriate aliquot of the radiolabeled conjugate. This value was corrected for the counter efficiency (typically 75%) and related to the protein concentration of the conjugate, previously determined by absorbance at 280 nm, and the resulting value expressed as mCi/mg protein.

For some experiments, 2B8-MX-DTPA was radiolabeled with indium [111] following a protocol similar to the one described above but without purification by HPLC; this was referred to as the "mix-and-shoot" protocol.

vii. Preparation of Yttrium-[90]-Labeled 2B8-MX-DTPA ("Y2B8")

The same protocol described for the preparation of I2B8 was followed for the preparation of the yttrium-[90]-labeled 2B8-MX-DTPA ("Y2B8") conjugate except that 2 ng HCl was not utilized; all preparations of yttrium-labeled conjugates were purified by size-exclusion chromatography as described above.

C. Non-Human Animal Studies.

i. Biodistribution of Radiolabeled 2B8-MX-DTPA

I2B8 was evaluated for tissue biodistribution in six-to-eight week old BALB/c mice. The radiolabeled conjugate was prepared using clinical-grade 2B8-MX-DTPA following the "mix and shoot" protocol described above. The specific activity of the conjugate was 2.3 mCi/mg and the conjugate was formulated in PBS, pH 7.4 containing 50 mg/mL HSA. Mice were injected intravenously with 100 µL of I2B8 (approximately 21 µCi) and groups of three mice were sacrificed by cervical dislocation at 0, 24, 48, and 72 hours. After sacrifice, the tail, heart, lungs, liver, kidney, spleen, muscle, and femur were removed, washed and weighed; a sample of blood was also removed for analysis. Radioactivity associated with each specimen was determined by gamma counting and the percent injected dose per gram tissue subsequently determined. No attempt was made to discount the activity contribution represented by the blood associated with individual organs.

In a separate protocol, aliquots of 2B8-MX-DTPA incubated at 4° C. and 30° C. for 10 weeks were radiolabeled with indium-[111] to a specific activity of 2.1 mCi/mg for both preparations. These conjugates were then used in biodistribution studies in mice as described above.

For dosimetry determinations, 2B8-MX-DTPA was radiolabeled with indium-[111] to a specific activity of 2.3 mCi/mg and approximately 1.1 µCi was injected into each of 20 BALB/c mice. Subsequently, groups of five mice each were sacrificed at 1, 24, 48 and 72 hours and their organs removed and prepared for analysis. In addition, portions of the skin, muscle and bone were removed and processed for analysis; the urine and feces were also collected and analyzed for the 24-72 hour time points.

Using a similar approach, 2B8-MX-DTPA was also radiolabeled with yttrium-[90] and its biological distribution evaluated in BALB/c mice over a 72-hour time period. Following purification by HPLC size exclusion chromatography, four groups of five mice each were injected intravenously with approximately 1 µCi of clinically-formulated conjugate (specific activity:12.2 mCi/mg); groups were subsequently sacrificed at 1, 24, 48 and 72 hours and their organs and tissues analyzed as described above. Radioactivity associated with each tissue specimen was determined by measuring bremstrahlung energy with a gamma scintillation counter. Activity values were subsequently expressed as percent injected dose per gram tissue or percent injected dose per organ. While organs and other tissues were rinsed repeatedly to remove superficial blood, the organs were not perfused. Thus, organ activity values were not discounted for the activity contribution represented by internally associated blood.

ii. Tumor Localization of I2B8

The localization of radiolabeled 2B8-MX-DTPA was determined in athymic mice bearing Ramos B cell tumors. Six-to-eight week old athymic mice were injected subcutaneously (left-rear flank) with 0.1 mL of RPMI-1640 containing $1.2 \times 10^7$ Ramos tumor cells which had been previously adapted for growth in athymic mice. Tumors arose within two weeks and ranged in weight from 0.07 to 1.1 grams. Mice were injected intravenously with 100 µL of indium-[111]-labeled 2B8-MX-DTPA (16.7 µCi) and groups of three mice were sacrificed by cervical dislocation at 0, 24, 48, and 72 hours. After sacrifice the tail, heart, lungs, liver, kidney, spleen, muscle, femur, and tumor were removed, washed, weighed; a sample of blood was also removed for analysis. Radioactivity associated with each specimen was determined by gamma counting and the percent injected dose per gram tissue determined.

iii. Biodistribution and Tumor Localization Studies with Radiolabeled 2B8-MX-DTPA Following the preliminary biodistribution experiment described above (Example I.B.viii.a.), conjugated 2B8 was radiolabeled with indium-[111] to a specific activity of 2.3 mCi/mg and roughly 1.1 µCi was injected into each of twenty BALB/c mice to determine biodistribution of the radiolabeled material. Subsequentially, groups of five mice each were sacrificed at 1, 24, 48 and 72 hours and their organs and a portion of the skin, muscle and bone were removed and processed for analysis. In addition, the urine and feces were collected and analyzed for the 24-72 hour time-points. The level of radioactivity in the blood dropped from 40.3% of the injected dose per gram at 1 hour to 18.9% at 72 hours (data not shown). Values for the heart, kidney, muscle and spleen remained in the range of 0.7-9.8% throughout the experiment. Levels of radioactivity found in the lungs decreased from 14.2% at 1 hour to 7.6% at 72 hours; similarly the respective liver injected-dose per gram values were 10.3% and 9.9%. These data were used in determining radiation absorbed dose estimates I2B8 described below.

The biodistribution of yttrium-[90]-labeled conjugate, having a specific activity of 12.2 mCi/mg antibody, was evaluated in BALB/c mice. Radioincorporations of >90% were obtained and the radiolabeled antibody was purified by HPLC. Tissue deposition of radioactivity was evaluated in the major organs, and the skin, muscle, bone, and urine and feces over 72 hours and expressed as percent injected dose/g tissue. Results (not shown) evidenced that while the levels of radioactivity associated with the blood dropped from approximately 39.2% injected dose per gram at 1 hour to roughly 15.4% after 72 hours the levels of radioactivity associated with tail, heart, kidney, muscle and spleen remained fairly constant at 10.2% or less throughout the course of the experiment. Importantly, the radioactivity associated with the bone ranged from 4.4% of the injected dose per gram bone at 1 hour to 3.2% at 72 hours. Taken together, these results suggest that little free yttrium was associated with the conjugate and that little free radiometal was released during the course of the study. These data were used in determining radiation absorbed dose estimates for Y2B8 described below.

For tumor localization studies, 2B8-MX-DTPA was prepared and radiolabeled with [111]Indium to a specific activity of 2.7 mCi/mg. One hundred microliters of labeled conjugate (approximately 24 μCi) were subsequently injected into each of 12 athymic mice bearing Ramos B cell tumors. Tumors ranged in weight from 0.1 to 1.0 grams. At time points of 0, 24, 48, and 72 hours following injection, 50 μL of blood was removed by retro-orbital puncture, the mice sacrificed by cervical dislocation, and the tail, heart, lungs, liver, kidney, spleen, muscle, femur, and tumor removed. After processing and weighing the tissues, the radioactivity associated with each tissue specimen was determined using a gamma counter and the values expressed as percent injected dose per gram.

The results (not shown) evidenced that the tumor concentrations of the [111]In-2B8-MX-DTPA increased steadily throughout the course of the experiment. Thirteen percent of the injected dose was accumulated in the tumor after 72 hours. The blood levels, by contrast, dropped during the experiment from over 30% at time zero to 13% at 72 hours. All other tissues (except muscle) contained between 1.3 and 6.0% of the injected dose per gram tissue by the end of the experiment; muscle tissue contained approximately 13% of the injected dose per gram.

D. Human Studies i. 2B8 and 2B8-MX-DTPA: Immunohistology Studies with Human Tissues The tissue reactivity of murine monoclonal antibody 2B8 was evaluated using a panel of 32 different human tissues fixed with acetone. Antibody 2B8 reacts with the anti-CD20 antigen which had a very restricted pattern of tissue distribution, being observed only in a subset of cells in lymphoid tissues including those of hematopoietic origin.

In the lymph node, immunoreactivity was observed in a population of mature cortical B-lymphocytes as well as proliferating cells in the germinal centers. Positive reactivity was also observed in the peripheral blood, B-cell areas of the tonsils, white pulp of the spleen, and with 40-70% of the medullary lymphocytes found in the thymus. Positive reactivity was also seen in the follicles of the lamina propria (Peyer's Patches) of the large intestines. Finally, aggregates or scattered lymphoid cells in the stroma of various organs, including the bladder, breast, cervix, esophagus, lung, parotid, prostate, small intestine, and stomach, were also positive with antibody 2B8 (data not shown).

All simple epithelial cells, as well as the stratified epithelia and epithelia of different organs, were found to be unreactive. Similarly, no reactivity was seen with neuroectodermal cells, including those in the brain, spinal cord and peripheral nerves. Mesenchymal elements, such as skeletal and smooth muscle cells, fibroblasts, endothelial cells, and polymorphonuclear inflammatory cells were also found to be negative (data not shown).

The tissue reactivity of the 2B8-MX-DTPA conjugate was evaluated using a panel of sixteen human tissues which had been fixed with acetone. As previously demonstrated with the native antibody (data not shown), the 2B8-MX-DTPA conjugate recognized the CD20 antigen which exhibited a highly restricted pattern of distribution, being found only on a subset of cells of lymphoid origin. In the lymph node, immunoreactivity was observed in the B cell population. Strong reactivity was seen in the white pulp of the spleen and in the medullary lymphocytes of the thymus. Immunoreactivity was also observed in scattered lymphocytes in the bladder, heart, large intestines, liver, lung, and uterus, and was attributed to the presence of inflammatory cells present in these tissues. As with the native antibody, no reactivity was observed with neuroectodermal cells or with mesenchymal elements (data not shown).

ii. Clinical Analysis of I2B8 (Imaging) and Y2B8 (Therapy)

a. Phase I/II Clinical Trial Single Dose Therapy Study

A Phase I/II clinical analysis of I2B8 (imaging) followed by treatment with a single therepeutic dose of Y2B8 is currently being conducted. For the single-dose study, the following schema is being followed:

1. Peripheral Stem Cell (PSC) or Bone Marrow (BM) Harvest with Purging;
2. I2B8 Imaging;
3. Y2B8 Therapy (three Dose Levels); and
4. PSC or Autologous BM Transplantation (if necessary based upon absolute neutrophil count below 500/mm³ for three consecutive days or platelets below 20,000/mm³ with no evidence of marrow recovery on bone marrow examination).

The Dose Levels of Y2B8 are as follows:

| Dose Level | Dose (mCi) |
| --- | --- |
| 1. | 20 |
| 2. | 30 |
| 3. | 40 |

Three patients are to be treated at each of the dose levels for determination of a Maximum Tolerated Dose ("MTD").

Imaging (Dosimetry) Studies are conducted as follows: each patient is involved in two in vivo biodistribution studies using I2B8. In the first study, 2 mg of I2B8 (5 mCi), is administered as an intravenous (i.v.) infusion over one hour; one week later 2B8 (ie unconjugated antibody) is administered by i.v. at a rate not to exceed 250 mg/hr followed immediately by 2 mg of I2B8 (5 mCi) administered by i.v. over one hour. In both studies, immediately following the I2B8 infusion, each patient is imaged and imaging is repeated at time t=14-18 hr (if indicated), t=24 hr; t=72 hr; and t=96 hr (if indicated). Whole body average retention times for the indium [111] label are determined; such determinations are also made for recognizable organs or tumor lesions ("regions of interest").

The regions of interest are compared to the whole body concentrations of the label; based upon this comparison, an estimate of the localization and concentration of Y2B8 can be determined using standard protocols. If the estimated cumulative dose of Y2B8 is greater than eight (8) times the estimated whole body dose, or if the estimated cumulative dose for the liver exceeds 1500 cGy, no treatment with Y2B8 should occur.

If the imaging studies are acceptable, either 0.0 or 1.0 mg/kg patient body weight of 2B8 is administered by i.v. infusion at a rate not to exceed 250 mg/h. This is followed by administration of Y2B8 (10,20 or 40 mCi) at an i.v. infusion rate of 20 mCi/hr.

b. Phase I/II Clinical Trial: Multiple Dose Therapy Study

A Phase I/II clinical analysis of of Y2B8 is currently being conducted. For the multiple-dose study, the following schema is being followed:
1. PSC or BM Harvest;
2. I2B8 Imaging;
3. Y2B8 Therapy (three Dose Levels) for four doses or a total cumulative dose of 80 mCi; and
4. PSC or Autologous BM Transplantation (based upon decision of medical practitioner).

The Dose Levels of Y2B8 are as follows:

| Dose Level | Dose (mCi) |
|---|---|
| 1. | 10 |
| 2. | 15 |
| 3. | 20 |

Three patients are to be treated at each of the dose levels for determination of an MTD.

Imaging (Dosimetry) Studies are conducted as follows: A preferred imaging dose for the unlabeled antibody (ie 2B8) will be determined with the first two patients. The first two patients will receive 100 mg of unlabeled 2B8 in 250 cc of normal saline over 4 hrs followed by 0.5 mCi of I2B8—blood will be sampled for biodistribution data at times t=0, t=10 min., t=120 min., t=24 hr, and t=48 hr. Patients will be scanned with multiple regional gamma camera images at times t=2 hr, t=24 hr and t=48 hr. After scanning at t=48 hr, the patients will receive 250 mg of 2B8 as described, followed by 4.5 mCi of I2B8—blood and scanning will then follow as described. If 100 mg of 2B8 produces superior imaging, then the next two patients will receive 50 mg of 2B8 as described, followed by 0.5 mCi of I2B8 followed 48 hrs later by 100 mg 2B8 and then with 4.5 mCi of I2B8. If 250 mg of 2B8 produces superior imaging, then the next two patients will receive 250 mg of 2B8 as described, followed by 0.5 mCi of I2B8 followed 48 hrs later with 500 mg 2B8 and then with 4.5 mCi of I2B8. Subsequent patients will be treated with the lowest amount of 2B8 that provides optimal imaging. Optimal imaging will be defined by: (1) best effective imaging with the slowest disappearance of antibody; (2) best distribution minimizing compartmentalization in a single organ; and (3) best subjective resolution of the lesion (tumor/background comparison).

For the first four patients, the first therapeutic dose of Y2B8 will begin 14 days after the last dose of I2B8; for subsequent patients, the first therapeutic dose of Y2B8 will begin between two to seven days after the I2B8.

Prior to treatment with Y2B8, for the patients other than the first four, 2B8 will be administered as described, followed by i.v. infusion of Y2B8 over 5-10 min. Blood will be sampled for biodistribution at times t=0, t=10 min., t=120 min., t=24 hr and t=48 hr. Patients will receive repetitive doses of Y2B8 (the same dose administered as with the first dose) approximately every six to eight weeks for a maximum of four doses, or total cumulative dose of 80 mCi. It is most preferred that patients not receive a subsequent dose of Y2B8 until the patients' WBC is greater than/equal to 3,000 and AGC is greater than/equal to 100,000.

Following completion of the three-dose level study, an MTD will be defined. Additional patients will then be enrolled in the study and these will receive the MTD.

II. Chimeric Anti-CD20 Antibody Production ("C2B8")

A. Construction of Chimeric Anti-CD20 Immunoglobulin DNA Expression Vector

RNA was isolated from the 2B8 mouse hybridoma cell (as described in Chomczynki, P. et al., "Single step method of RNA isolation by acid guanidinium thiocyanate-phenol-chloroform extraction." *Anal. Biochem.* 162:156-159 (1987)). and cDNA was prepared therefrom. The mouse immunoglobulin light chain variable region DNA was isolated from the cDNA by polymerase chain reaction using a set of DNA primers with homology to mouse light chain signal sequences at the 5' end and mouse light chain J region at the 3' end. Primer sequences were as follows:

1. $V_L$ Sense (SEQ ID NO:8)
5' ATC AC <u>AGATCT</u> CTC ACC ATG GAT TTT CAG GTG CAG ATT ATC AGC TTC 3'

(The underlined portion is a Bgl II site; the above-lined portion is the start codon.)

2. $V_L$ Antisense (SEQ ID NO:9)
5' TGC AGC ATC <u>CGTACG</u> TTT GAT TTC CAG CTT 3'

(The underlined portion is a Bsi WI site.)

Figure 1:
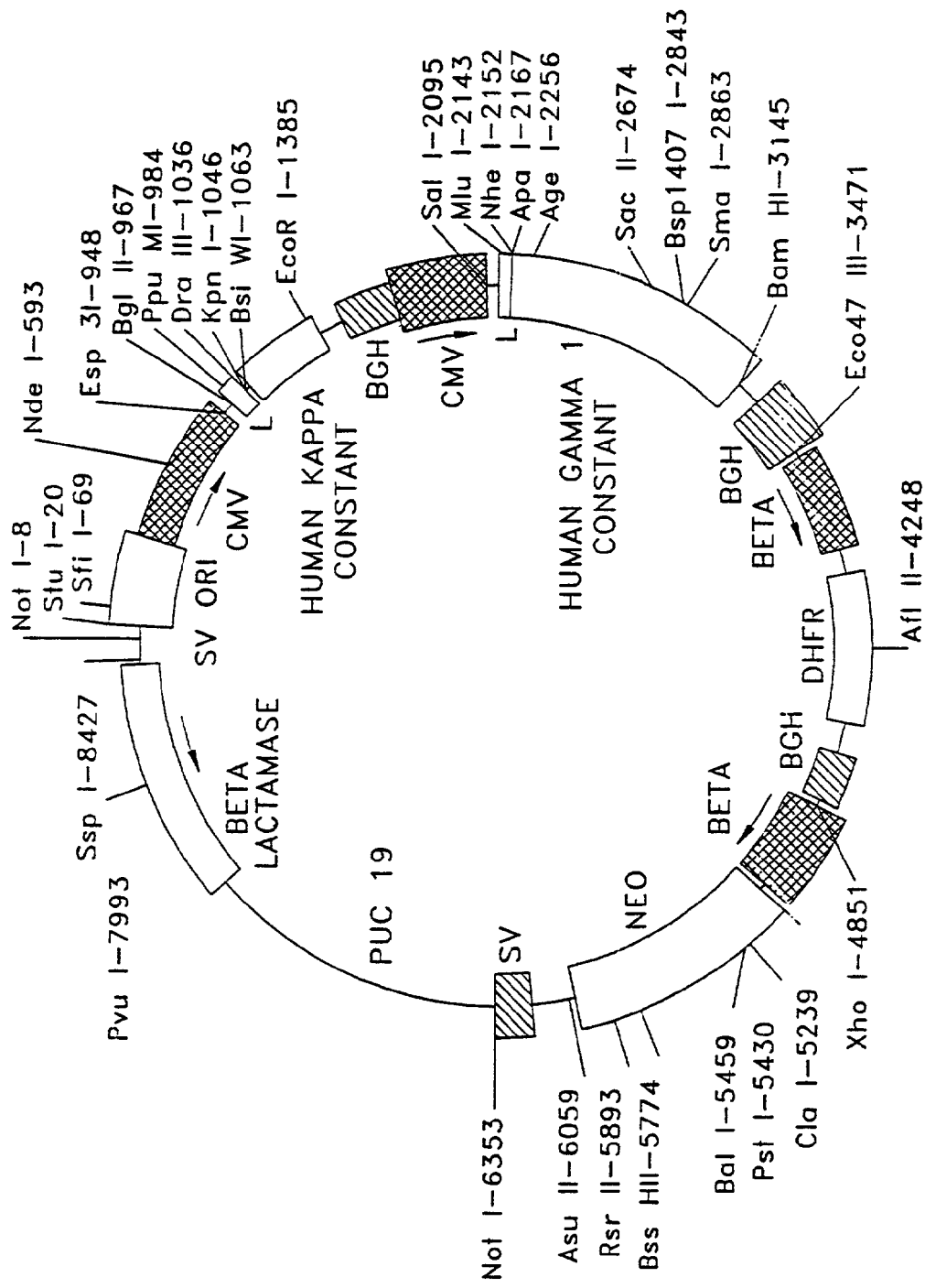
FIG. 1 is a diagrammatic representation of a tandem chimeric antibody expression vector useful in the production of immunologically active chimeric anti-CD20 antibodies ("TCAE 8")

See, FIGS. 1 and 2 for the corresponding Bgl II and Bsi WI sites in TCAE 8, and FIG. 3 for the corresponding sites in anti-CD20 in TCAE 8.

These resulting DNA fragments were cloned directly into the TCAE 8 vector in from of the human kappa light chain constant domain and sequenced. The determined DNA sequence for the murine variable region light chain is set forth in FIG. 4 (SEQ ID NO:3); see also FIG. 3, nucleotides 978 through 1362. FIG. 4 further provides the amino acid sequence from this murine variable region, and the CDR and framework regions (SEQ ID NO:4). The mouse light chain variable region from 2B is in the mouse kappa VI family. See Kabat, supra.

The mouse heavy chain variable region was similarly isolated and cloned in front of the human IgG1 constant domains. Primers were as follows:

```
1. V_H Sense (SEQ ID NO:10)
   5' GCG GCT CCC ACGCGT GTC CTG TCC CAG 3'
```

(The underlined portion is an Mlu I site.)

```
2. V_H Antisense (SEQ ID NO:11)
5' GG(G/C) TGT TGT GCTAGC TG(A/C) (A/G)GA GAC
(G/A)GT GA 3'
```

(The underlined portion is an Nhe I site.)

See, FIGS. 1 and 2 for corresponding Mlu I and Nhe I sites in TCAE 8, and FIG. 3 for corresponding sites in anti-CD20 in TCAE 8.

The sequence for this mouse heavy chain is set forth in FIG. 5 (SEQ ID NO:5); see also FIG. 3, nucleotide 2401 through 2820. FIG. 5 also provides the amino acid sequence from this murine variable region, and the CDR and framework regions (SEQ ID NO:6). The mouse heavy chain variable region from 2B8 is in the mouse VH 2B family. See Kabat, supra.

B. Creation of Chimeric Anti-CD20 Producing CHO and SP2/0 Transfectomas

Chinese hamster ovary ("CHO") cells DG44 were grown in SSFM II minus hypoxanthine and thymidine media (Gibco, Grand Island, N.Y., Form No. 91-0456PK); SP2/0 mouse myeloma cells were grown in Dulbecco's Modified Eagles Medium media ("DMEM") (Irvine Scientific, Santa Ana, Calif., Cat. No. 9024) with 5% fetal bovine serum and 20 ml/L glutamine added. Four million cells were electroporated with either 25 µg CHO or 50 µg SP2/0 plasmid DNA that had been restricted with Not I using a BTX 600 electroporation system (BTX, San Diego, Calif.) in 0.4 ml disposable cuvettes. Conditions were either 210 volts for CHO or 180 volts for SP2/0, 400 microfaradays, 13 ohms. Each electroporation was plated into six 96 well dishes (about 7,000 cells/well). Dishes were fed with media containing G418 (GENETICIN, Gibco, Cat. No. 860-1811) at 400 µg/ml active compound for CHO (media further included 50 µM hypoxanthine and 8 µM thymidine) or 800 µg/ml for SP2/0, two days following electroporation and thereafter 2 or 3 days until colonies arose. Supernatant from colonies was assayed for the presence of chimeric immunoglobulin via an ELISA specific for human antibody. Colonies producing the highest amount of immunoglobulin were expanded and plated into 96 well plates containing media plus methotrexate (25 nM for SP2/0 and 5nM for CHO) and fed every two or three days. Supernatants were assayed as above and colonies producing the highest amount of immunoglobulin were examined. Chimeric anti-CD20 antibody was purified from supernatant using protein A affinity chromatography.

Purified chimeric anti-CD20 was analyzed by electrophoresis in polyacrylamide gels and estimated to be greater than about 95% pure. Affinity and specificity of the chimeric antibody was determined based upon 2B8. Chimeric anti-CD20 antibody tested in direct and competitive binding assays, when compared to murine anti-CD20 monoclonal antibody 2B8, evidenced comparable affinity and specificity on a number of CD20 positive B cells lines (data not presented). The apparent affinity constant ("Kap") of the chimeric antibody was determined by direct binding of $I^{125}$ radiolabeled chimeric anti-CD20 and compared to radiolabeled 2B8 by Scatchard plot; estimated Kap for CHO produced chimeric anti-CD20 was $5.2 \times 10^{-9}$ M and for SP2/0 produced antibody, $7.4 \times 10^{-9}$ M. The estimated Kap for 2B8 was $3.5 \times 10^{-9}$ M. Direct competition by radioimmunoassay was utilized to confirm both the specificity and retention of immunoreactivity of the chimeric antibody by comparing its ability to effectively compete with 2B8. Substantially equivalent amounts of chimeric anti-CD20 and 2B8 antibodies were required to produce 50% inhibition of binding to CD20 antigens on B cells (data not presented), ie there was a minimal loss of inhibiting activity of the anti-CD20 antibodies, presumably due to chimerization.

The results of Example II.B indicate, inter alia, that chimeric anti-CD20 antibodies were generated from CHO and SP2/0 transfectomas using the TCAE 8 vectors, and these chimeric antibodies had substantially the same specificity and binding capability as murine anti-CD20 monoclonal antibody 2B8.

C. Determination of Immunological Activity of Chimeric Anti-CD20 Antibodies i. Human C1q Analysis Chimeric anti-CD20 antibodies produced by both CHO and SP2/0 cell lines were evaluated for human C1q binding in a flow cytometry assay using fluorescein labeled C1q (C1q was obtained from Quidel, Mira Mesa, Calif., Prod. No. A400 and FITC label from Sigma, St. Louis Mo., Prod. No. F-7250; FITC. Labeling of C1q was accomplished in accordance with the protocol described in *Selected Methods In Cellular Immunology*, Michell & Shiigi, Ed. (W. H. Freeman & Co., San Francisco, Calif., 1980, p. 292). Analytical results were derived using a Becton Dickinson FACScan™ flow cytometer (fluorescein measured over a range of 515-545 nm). Equivalent amounts of chimeric anti-CD20 antibody, human IgG1,K myeloma protein (Binding Site, San Diego, Calif., Prod. No. BP078), and 2B8 were incubated with an equivalent number of CD20-positive SB cells, followed by a wash step with FACS buffer (0.2% BSA in PBS, pH 7.4, .02% sodium azide) to remove unattached antibody, followed by incubation with FITC labeled C1q. Following a 30-60 min. incubation, cells were again washed. The three conditions, including FITC-labeled C1q as a control, were analyzed on the FACScan™ following manufacturing instructions. Results are presented in FIG. 6.

Figure 6:
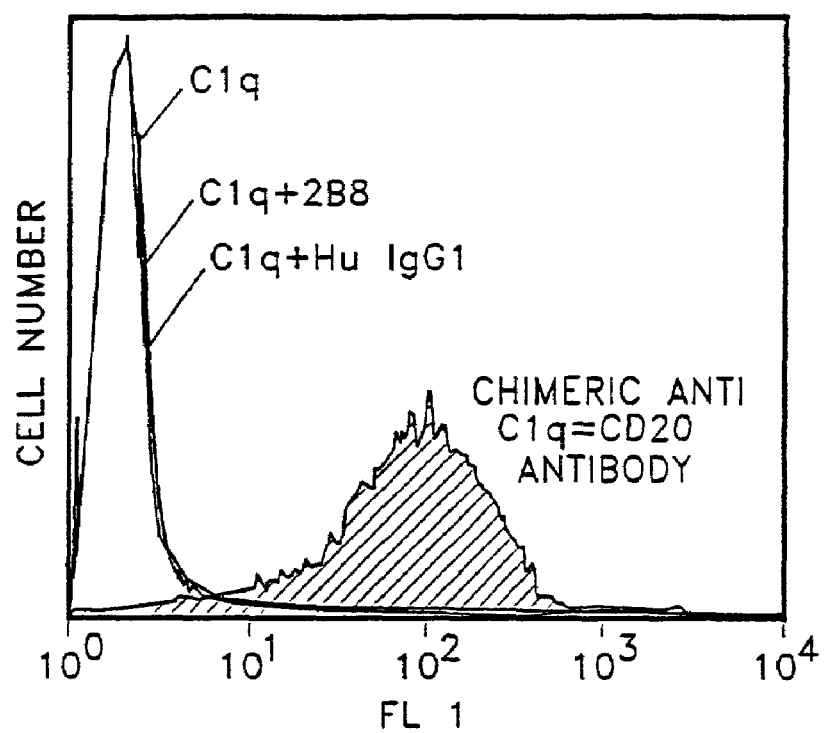
FIG. 6 are flow cytometry results evidencing binding of fluorescent-labeled human C1q to chimeric anti-CD20 antibody, including, as controls labeled C1q; labeled C1q and murine anti-CD20 monoclonal antibody 2B8; and labeled C1q and human IgG1,k.

As the results of FIG. 6 evidence, a significant increase in fluorescence was observed only for the chimeric anti-CD20 antibody condition; ie only SB cells with adherent chimeric anti-CD20 antibody were C1q positive, while the other conditions produced the same pattern as the control.

ii. Complement Dependent Cell Lyses

Chimeric anti-CD20 antibodies were analyzed for their ability to lyse lymphoma cell lines in the presence of human serum (complement source). CD20 positive SB cells were labeled with $^{51}Cr$ by admixing 100 µCi of $^{51}Cr$ with $1 \times 10^6$ SB cells for 1 hr at 37° C.; labeled SB cells were then incubated in the presence of equivalent amounts of human complement and equivalent amounts (0-50 µg/ml) of either chimeric anti-CD20 antibodies or 2B8 for 4 hrs at 37° C. (see, Brunner. K. T. at al., "Quantitative assay of the lytic action of immune lymphoid cells on $^{51}Cr$-labeled allogeneic target cells in vitro." *Immunology* 14:181-189 (1968). Results are presented in FIG. 7.

Figure 7:
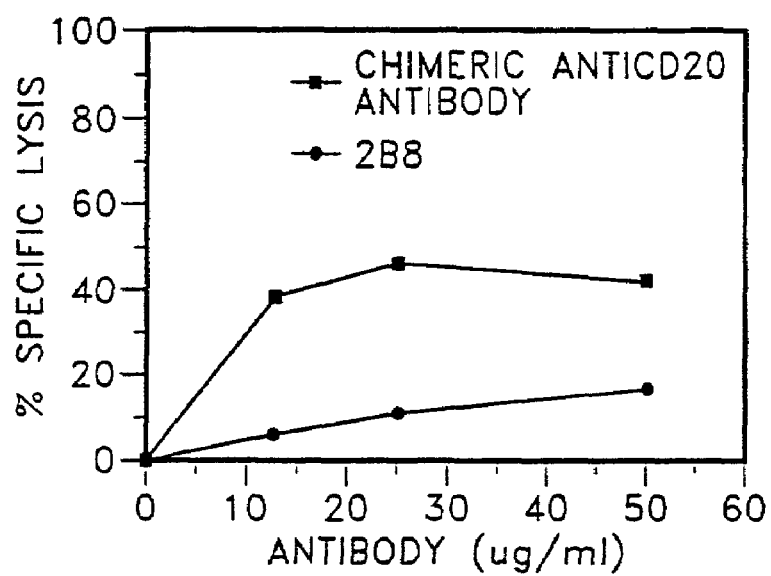
FIG. 7 represents the results of complement related lysis comparing chimeric anti-CD20 antibody and murine anti-CD20 monoclonal antibody 2B8.

The results of FIG. 7 indicate, inter alia, that chimeric anti-CD20 antibodies produced significant lysis (49%) under these conditions.

iii. Antibody Dependent Cellular Cytotoxicity Effector Assay

Figure 8:
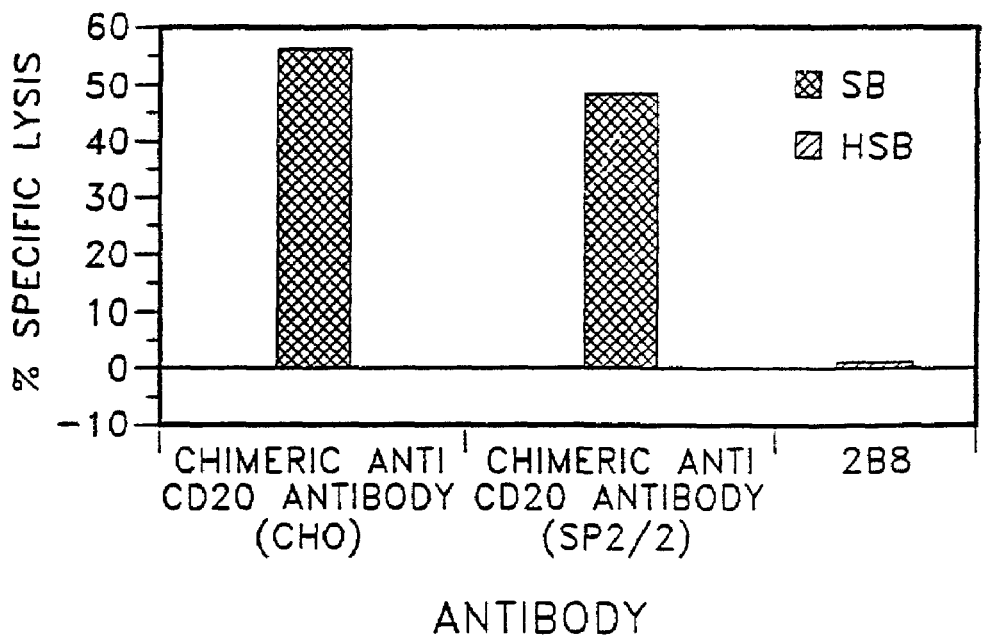
FIG. 8 represents the results of antibody mediated cellular cytotoxicity with in vivo human effector cells comparing chimeric anti-CD20 antibody and 2B8.

For this study, CD20 positive cells (SB) and CD20 negative cells (T cell leukemia line HSB; see, Adams, Richard, "Formal Discussion," *Can. Res.* 27:2479-2482 (1967); ATCC deposit no. ATCC CCL 120.1) were utilized; both were labeled with $^{51}$Cr. Analysis was conducted following the protocol described in Brunner, K. T. et al., "Quantitative assay of the lytic action of immune lymphoid cells on $^{51}$Cr-labeled allogeneic target cells in vitro; inhibition by isoantibody and drugs." *Immunology* 14:181-189 (1968); a substantial chimeric anti-CD20 antibody dependent cell mediated lysis of CD20 positive SB target cells ($^{51}$Cr-labeled) at the end of a 4 hr, 37° C. incubation, was observed and this effect was observed for both CHO and SP2/0 produced antibody (effector cells were human peripheral lymphocytes; ratio of effector cells:target was 100:1). Efficient lysis of target cells was obtained at 3.9 µg/ml. In contrast, under the same conditions, the murine anti-CD20 monoclonal antibody 2B8 had a statistically insignificant effect, and CD20 negative HSB cells were not lysed. Results are presented in FIG. 8.

The results of Example II indicate, inter alia, that the chimeric anti-CD20 antibodies of Example I were immunologically active.

III. Depletion of B Cells In Vivo using Chimeric Anti-CD20

A Non-Human Primate Study

Three separate non-human primate studies were conducted. For convenience, these are referred to herein as "Chimeric Anti-CD20: CHO & SP2/0;" "Chimeric Anti-CD20: CHO;" and "High Dosage Chimeric Anti-CD20." Conditions were as follows:

Chimeric Anti-CD20: CHO & SP2/0

Six cynomolgus monkeys ranging in weight from 4.5 to 7 kilograms (White Sands Research Center, Alamogordo, N. Mex.) were divided into three groups of two monkeys each. Both animals of each group received the same dose of immunologically active chimeric anti-CD20 antibody. One animal in each group received purified antibody produced by the CHO transfectoma; the other received antibody produced by the SP2/0 transfectoma. The three groups received antibody dosages corresponding to 0.1 mg/kg, 0.4 mg/kg, and 1.6 mg/kg each day for four (4) consecutive days. The chimeric immunologically active anti-CD20 antibody, which was admixed with sterile saline, was administered by intravenous infusion; blood samples were drawn prior to each infusion. Additional blood samples were drawn beginning 24 hrs after the last injection (T=O) and thereafter on days 1, 3, 7, 14 and 28; blood samples were also taken thereafter at biweekly intervals until completion of the study at day 90.

Approximately 5 ml of whole blood from each animal was centrifuged at 2000 RPM for 5 min. Plasma was removed for assay of soluble chimeric anti-CD20 antibody levels. The pellet (containing peripheral blood leukocytes and red blood cells) was resuspended in fetal calf serum for fluorescent-labeled antibody analysis (see, "Fluorescent Antibody Labeling of Lymphoid Cell Population," infra.).

Chimeric Anti-CD20: CHO

Six cynomolgus monkeys ranging in weight from 4 to 6 kilograms (White Sands) were divided into three groups of two monkeys each. All animals were injected with immunologically active chimeric anti-CD20 antibodies produced from the CHO transfectoma (in sterile saline). The three groups were separated as follows: subgroup 1 received daily intravenous injections of 0.01 mg/kg of the antibody over a four (4) day period; subgroup 2 received daily intravenous injections of 0.4 mg/kg of the antibody over a four (4) day period; subgroup 3 received a single intravenous injection of 6.4 mg/kg of the antibody. For all three subgroups, a blood sample was obtained prior to initiation of treatment; additionally, blood samples were also drawn at T=0, 1, 3, 7, 14 and 28 days following the last injection, as described above, and these samples were processed for fluorescent labeled antibody analysis (see, "Fluorescent Antibody Labeling," infra.). In addition to peripheral blood B cell quantitation, lymph node biopsies were taken at days 7, 14 and 28 following the last injection, and a single cell preparation stained for quantitation of lymphocyte populations by flow cytometry.

High Dosage Chimeric Anti-CD20

Two cynomolgus monkeys (White Sands) were infused with 16.8 mg/kg of the immunologically active chimeric anti-CD20 antibodies from the CHO transfectomas (in sterile saline) weekly over a period of four consecutive weeks. At the conclusion of the treatment, both animals were anesthetized for removal of bone marrow; lymph node biopsies were also taken. Both sets of tissue were stained for the presence of B lymphocytes using Leu 16 by flow cytometry following the protocol described in Ling, N. R. et al., "B-cell and plasma cell antigens." *Leucocyte Typing III White Cell Differentiations Antigens*, A. J. McMichael, Ed. (Oxford University Press, Oxford UK, 1987), p. 302.

Fluorescent Antibody Labeling of Lymphoid Cell Population

After removal of plasma, leukocytes were washed twice with Hanks Balanced Salt Solution ("HBSS") and resuspended in a plasma equivalent volume of fetal bovine serum (heat inactivated at 56° C. for 30 min.). A 0.1 ml volume of the cell preparation was distributed to each of six (6), 15 ml conical centrifuge tubes Fluorescein labeled monoclonal antibodies with specificity for the human lymphocyte surface markers CD2 (AMAC, Westbrook, Me.), CD20 (Becton Dickinson) and human IgM (Binding Site, San Diego, Calif.) were added to 3 of the tubes for identifying T and B lymphocyte populations. All reagents had previously tested positive to the corresponding monkey lymphocyte antigens. Chimeric anti-CD20 antibody bound to monkey B cell surface CD20 was measured in the fourth tube using polyclonal goat anti-human IgG coupled with phycoerythrin (AMAC). This reagent was pre-adsorbed on a monkey Ig-sepharose column to prevent cross-reactivity to monkey Ig, thus allowing specific detection and quantitation of chimeric anti-CD20 antibody bound to cells. A fifth tube included both anti-IgM and anti-human IgG reagents for double stained B cell population. A sixth sample was included with no reagents for determination of autofluorescence. Cells were incubated with fluorescent antibodies for 30 min., washed and fixed with 0.5 ml of fixation buffer (0.15 M NaCl, 1% paraformaldehyde, pH7.4) and analyzed on a Becton Dickinson FACScan™ instrument. Lymphocyte populations were initially identified by forward versus right angle light scatter in a dot-plot bitmap with unlabeled leucocytes. The total lymphocyte population was then isolated by gating out all other events. Subsequent fluorescence measurements reflected only gated lymphocyte specific events.

Depletion of Peripheral Blood B Lymphocytes

No observable difference could be ascertained between the efficacy of CHO and SP2/0 produced antibodies in depleting B cells in vivo, although a slight increase in B cell recovery beginning after day 7 for monkeys injected with chimeric anti-CD20 antibodies derived from CHO transfectomas at dosage levels 1.6 mg/kg and 6.4 mg/kg was observed and for the monkey injected with SP2/0 producing antibody at the 0.4 mg/kg dose level. FIGS. 9A, B and C provide the results derived from the chimeric anti-CD20: CHO & SP2/0 study, with FIG. 9A directed to the 0.4 mg/kg dose level; FIG. 9B directed to the 1.6 mg/kg dose level; and FIG. 9C directed to the 6.4 mg/kg dose level.

As is evident from FIG. 9, there was a dramatic decrease (>95%) in peripheral B cell levels after the therapeutic treatment across all tested dose ranges, and these levels were maintained up to seven (7) days post infusion; after this period, B cell recovery began, and, the time of recovery initiation was independent of dosage levels.

In the Chimeric Anti-CD20:CHO study, a 10-fold lower antibody dosage concentration (0.01 mg/kg) over a period of four daily injections (0.04 mg/kg total) was utilized. FIG. 10 provides the results of this study. This dosage depleted the peripheral blood B cell population to approximately 50% of normal levels estimated with either the anti-surface IgM or the Leu 16 antibody. The results also indicate that saturation of the CD20 antigen on the B lymphocyte population was not achieved with immunologically active chimeric anti-CD20 antibody at this dose concentration over this period of time for non-human primates; B lymphocytes coated with the antibody were detected in the blood samples during the initial three days following therapeutic treatment. However, by day 7, antibody coated cells were undetectable.

Table I summarizes the results of single and multiple doses of immunologically active chimeric anti-CD20 antibody on the peripheral blood populations; single dose condition was 6.4 mg/kg; multiple dose condition was 0.4 mg/kg over four (4) consecutive days (these results were derived from the monkeys described above).

TABLE I

PERIPHERAL BLOOD POPULATION FROM C2B8 PRIMATE STUDY

| Monkey | Dose | Day | CD2 | Anti-Hu IgG |
|---|---|---|---|---|
| A | 0.4 mg/kg | Prebleed | 81.5 | — |
|   | (4 doses) | 0 | 86.5 | 0.2 |
|   |   | 7 | 85.5 | 0.0 |
|   |   | 21 | 93.3 | — |
|   |   | 28 | 85.5 | — |
| B | 0.4 mg/kg | Prebleed | 81.7 | — |
|   | (4 doses) | 0 | 94.6 | 0.1 |
|   |   | 7 | 92.2 | 0.1 |
|   |   | 21 | 84.9 | — |
|   |   | 28 | 84.1 | — |
| C | 6.4 mg/kg | Prebleed | 77.7 | 0.0 |
|   | (1 dose) | 7 | 85.7 | 0.1 |
|   |   | 21 | 86.7 | — |
|   |   | 28 | 76.7 | — |
| D | 6.4 mg/kg | Prebleed | 85.7 | 0.1 |
|   | (1 dose) | 7 | 94.7 | 0.1 |
|   |   | 21 | 85.2 | — |
|   |   | 28 | 85.9 | — |

| Monkey | Anti-Hu IgG + Anti-Hu IgM* | Leu-16 | % B Cell Depletion |
|---|---|---|---|
| A | — | 9.4 | 0 |
|   | 0.3 | 0.0 | 97 |
|   | 0.1 | 1.2 | 99 |
|   | — | 2.1 | 78 |
|   | — | 4.1 | 66 |
| B | — | 14.8 | 0 |
|   | 0.2 | 0.1 | 99 |
|   | 0.1 | 0.1 | 99 |

TABLE I-continued

PERIPHERAL BLOOD POPULATION FROM C2B8 PRIMATE STUDY

|   |   |   |   |   |
|---|---|---|---|---|
|   | — | 6.9 | 53 |
|   | — | 8.7 | 41 |
| C | 0.2 | 17.0 | 0 |
|   | 0.1 | 0.0 | 99 |
|   | — | 14.7 | 15 |
|   | — | 8.1 | 62 |
| D | 0.1 | 14.4 | 0 |
|   | 0.2 | 0.0 | 99 |
|   | — | 9.2 | 46 |
|   | — | 6.7 | 53 |

*Double staining population which indicates extent of chimeric anti-CD20 coated B cells.

The data summarized in Table I indicates that depletion of B cells in peripheral blood under conditions of antibody excess occurred rapidly and effectively, regardless of single or multiple dosage levels. Additionally, reption was observed for at least seven (7) days following the last injection, with partial B cell recovery observed by day 21.

Table II summarizes the effect of immunologically active, chimeric anti-CD20 antibodies on cell populations of lymph nodes using the treatment regimen of Table I (4 daily doses of 0.4 mg/kg; 1 dose of 6.4 mg/kg); comparative values for normal lymph nodes (control monkey, axillary and inguinal) and normal bone marrow (two monkeys) are also provided.

TABLE II

CELL POPULATIONS OF LYMPH NODES

| Monkey | Dose | Day | CD2 | Anti-Hu IgM |
|---|---|---|---|---|
| A | 0.4 mg/kg | 7 | 66.9 | — |
|   | (4 doses) | 14 | 76.9 | 19.6 |
|   |   | 28 | 61.6 | 19.7 |
| B | 0.4 mg/kg | 7 | 59.4 | — |
|   | (4 doses) | 14 | 83.2 | 9.9 |
|   |   | 28 | 84.1 | 15.7 |
| C | 6.4 mg/kg | 7 | 75.5 | — |
|   | (1 dose) | 14 | 74.1 | 17.9 |
|   |   | 28 | 66.9 | 23.1 |
| D | 6.4 mg/kg | 7 | 83.8 | — |
|   | (1 dose) | 14 | 74.1 | 17.9 |
|   |   | 28 | 84.1 | 12.8 |

| Monkey | Anti-Hu IgG + Anti-Hu IgM | Leu-16 | % B Lymphocyte Depletion |
|---|---|---|---|
| A | 7.4 | 40.1 | 1 |
|   | 0.8 | 22.6 | 44 |
|   | — | 26.0 | 36 |
| B | 29.9 | 52.2 | 0 |
|   | 0.7 | 14.5 | 64 |
|   | — | 14.6 | 64 |
| C | 22.3 | 35.2 | 13 |
|   | 1.1 | 23.9 | 41 |
|   | — | 21.4 | 47 |
| D | 12.5 | 19.7 | 51 |
|   | 0.2 | 8.7 | 78 |
|   | — | 12.9 | 68 |

|   | CD2 | Anti-Hu IgG + Anti-Hu IgM | Anti-Hu IgM | Leu-16 | % B Lymphocyte Depletion |
|---|---|---|---|---|---|
| Normal Lymph Nodes |   |   |   |   |   |
| Control 1 |   |   |   |   |   |
| Axillary | 55.4 | 25.0 | — | 41.4 | NA |
| Inguinal | 52.1 | 31.2 | — | 39.5 | NA |

TABLE II-continued

CELL POPULATIONS OF LYMPH NODES

| Normal Bone Marrow | | | | | |
|---|---|---|---|---|---|
| Control 2 | 65.3 | 19.0 | — | 11.4 | NA |
| Control 3 | 29.8 | 28.0 | — | 16.6 | NA |

The results of Table II evidence effective depletion of B lymphocytes for both treatment regimens. Table II further indicates that for the non-human primates, complete saturation of the B cells in the lymphatic tissue with immunologically active, chimeric anti-CD20 antibody was not achieved; additionally, antibody coated cells were observed seven (7) days after treatment, followed by a marked depletion of lymph node B cells, observed on day 14.

Based upon this data, the single High Dosage Chimeric Anti-CD20 study referenced above was conducted, principally with an eye toward pharmacology/toxicology determination. Ie this study was conducted to evaluate any toxicity associated with the administration of the chimeric antibody, as well as the efficacy of B cell depletion from peripheral blood lymph nodes and bone marrow. Additionally, because the data of Table II indicates that for that study, the majority of lymph node B cells were depleted between 7 and 14 days following treatment, a weekly dosing regimen might evidence more efficacious results. Table III summarizes the results of the High Dosage Chimeric Anti-CD20 study.

TABLE III

CELL POPULATIONS OF LYMPH NODES AND BONE MARROW
Lymphocyte Populations (%)

| Monkey | CD2 | CD20[a] | mIgM + anti-C2B8[b] | C2B8[c] | Day[d] |
|---|---|---|---|---|---|
| Inguinal Lymph Node | | | | | |
| E | 90.0 | 5.3 | 4.8 | 6.5 | 22 |
| F | 91.0 | 6.3 | 5.6 | 6.3 | 22 |
| G | 89.9 | 5.0 | 3.7 | 5.8 | 36 |
| H | 85.4 | 12.3 | 1.7 | 1.8 | 36 |
| Bone Marrow | | | | | |
| E | 46.7 | 4.3 | 2.6 | 2.8 | 22 |
| F | 41.8 | 3.0 | 2.1 | 2.2 | 22 |
| G | 35.3 | 0.8 | 1.4 | 1.4 | 36 |
| H | 25.6 | 4.4 | 4.3 | 4.4 | 36 |

[a]Indicates population stained with Leu 16.
[b]Indicates double staining population, positive for surface IgM cells and chimeric antibody coated cells.
[c]Indicates total population staining for chimeric antibody including double staining surface IgM positive cells and single staining (surface IgM negative) cells.
[d]Days after injection of final 16.8 mg/kg dose.

Both animals evaluated at 22 days post treatment cessation contained less than 5% B cells, as compared to 40% in control lymph nodes (see, Table II, supra). Similarly, in the bone marrow of animals treated with chimeric anti-CD20 antibody, the levels of CD20 positive cells were less than 3% as compared to 11-15% in the normal animals (see, Table II, supra). In the animals evaluated at 36 days post treatment cessation, one of the animals (H) had approximately 12% B cells in the lymph node and 4.4% B cells in bone marrow, while the other (G) had approximately 5% B cells in the lymph node and 0.8% in the bone marrow—the data is indicative of significant B cell depletion.

The results of Example III.A indicate, intar alia, that low doses of immunologically active, chimeric anti-CD20 leads to long-term peripheral blood B cell depletion in primates. The data also indicates that significant depletion of B cell populations was achieved in peripheral lymph nodes and bone marrow when repetitive high doses of the antibody were administered. Continued follow-up on the test animals has indicated that even with such severe depletion of peripheral B lymphocytes during the first week of treatment, no adverse health effects have been observed. Furthermore, as recovery of B cell population was observed, a conclusion to be drawn is that the pluripotent stem cells of these primates were not adversely affected by the treatment.

B. Clinical Analysis of C2B8
  i. Phase I/II Clinical Trial of C2B8: Single Dose Therapy Study Fifteen patients having histologically documented relapsed B cell lymphoma have been treated with C2B8 in a Phase I/II Clinical Trial. Each patient received a single dose of C2B8 in a dose-escalating study; there were three patients per dose: 10 mg/m$^2$; 50 mg/m$^2$; 100 mg/m$^2$; 250 mg/m$^2$ and 500 mg/m$^2$. Treatment was by i.v. infusion through an 0.22 micron in-line filter with C2B8 being diluted in a final volume of 250 cc or a maximal concentration of 1 mg/ml of normal saline. Initial rate was 50 cc/hr for the first hour; if no toxicity was seen, dose rate was able to be escalated to a maximum of 200 cc/hr.

Toxicity (as indicated by the clinician) ranged from "none", to "fever" to "moderate" (two patients) to "severe" (one patient); all patients completed the therapy treatment. Peripheral Blood Lymphocytes were analyzed to determine, inter alia, the impact of C2B8 on T-cells and B-cells. Consistently for all patients, Peripheral Blood B Lymphocytes were depleted after infusion with C2B8 and such depletion was maintained for in excess of two weeks.

One patient (receiving 100 mg/$^2$ of C2B8) evidenced a Partial Response to the C2B8 treatment (reduction of greater than 50% in the sum of the products of the perpendicular diameters of all measurable indicator lesions lasting greater than four weeks, during which no new lesions may appear and no existing lesions may enlarge); at least one other patient (receiving 500 mg/m$^2$) evidenced a Minor Response to the C2B8 treatment (reduction of less than 50% but at least 25% in the sum of the products of the two longest perpendicular diameters of all measurable indicator lesions). For presentational efficiency, results of the PBLs are set forth in FIG. 14; data for the patient evidencing a PR is set forth in FIG. 14A; for the patient evidencing an MR, data is set forth in FIG. 14B. In FIG. 14, the following are applicable: ■=Lymphocytes; ☐=CD3+ cells (T cells); ▲=CD20$^+$cells; ●=CD19$^+$cells; ⊖=Kappa; △=lambda; and ◆=C2B8. As evidenced, the B cell markers CD20 and CD19, Kappa and Lambda, were depleted for a period in excess of two weeks; while there was a slight, initial reduction in T-cell counts, these returned to an approximate base-line level in a relatively rapid time-frame.

ii. Phase I/II Clinical Trial of C2B8: Multiple Dose Therapy Study

Patients having histologically confirmed B cell lymphoma with measurable progressive disease are eligible for this study which is separated into two parts: in Phase I, consisting of a dose escalation to characterize dose limiting toxicities and determination of biologically active tolerated dose level, groups of three patients will receive weekly i.v.

infusions of C2B8 for a total of four (4) separate infusions. Cumulative dose at each of the three levels will be as follows: 500 mg/m$^2$ (125 mg/m$^2$/infusion); 1000 mg/m$^2$ (250 mg/m$^2$/infusion); 1500 mg/m$^2$ (375 mg/m$^2$/infusion. A biologically active tolerated dose is defined, and will be determined, as the lowest dose with both tolerable toxicity and adequate activity); in Phase II, additional patients will receive the biologically active tolerated dose with an emphasis on determining the activity of the four doses of C2B8.

IV. Combination Therapy: C2B8 and Y2B8

A combination therapeutic approach using C2B8 and Y2B8 was investigated in a mouse xenographic model (nu/nu mice, female, approximately 10 weeks old) utilizing a B cell lymphoblastic tumor (Ramos tumor cells). For comparative purposes, additional mice were also treated with C2B8 and Y2B8.

Ramos tumor cells (ATCC, CRL 1596) were maintained in culture using RPMI-1640 supplemented with 10% fetal calf serum and glutamine at 37° C. and 5% $CO_2$. Tumors were initiated in nine female nude mice approximately 7-10 weeks old by subcutaneous injection of $1.7 \times 10^6$ Ramos cells in a volume of 0.10 ml (HBSS) using a 1 cc syringe fitted with 25 g needle. All animals were manipulated in a laminar flow hood and all cages, bedding, food and water were autoclaved. Tumor cells were passaged by excising tumors and passing these through a 40 mesh screen; cells were washed twice with 1× HBSS (50 ml) by centrifugation (1300RPM), resuspended in I× HBSS to $10 \times 10^6$ cells/ml, and frozen at −70° C. until used.

For the experimental conditions, cells from several frozen lots were thawed, pelleted by centrifugation (1300RPM) and washed twice with 1× HBSS. Cells were then resuspended to approximately $2.0 \times 10^6$ cells/ml. Approximately 9 to 12 mice were injected with 0.10 ml of the cell suspension (s.c.) using a 1 cc syringe fitted with a 25 g needle; injections were made on the animal's left side, approximately mid-region. Tumors developed in approximately two weeks. Tumors were excised and processed as described above. Study mice were injected as described above with $1.67 \times 10^6$ cells in 0.10 ml HBSS.

Based on preliminary dosing experiments, it was determined that 200 mg of C2B8 and 100 µCi of Y2B8 would be utilized for the study. Ninety female nu/nu mice (approximately 10 weeks old) were injected with the tumor cells. Approximately ten days later, 24 mice were assigned to four study groups (six mice/group) while attempting to maintain a comparable tumor size distribution in each group (average tumor size, expressed as a product of length x width of the tumor, was approximately 80 mm$^2$). The following groups were treated as indicated via tail-vain injections using a 100 µl Hamilton syringe fitted with a 25 g needle:

A. Normal Saline
B. Y2B8 (100 µCi)
C. C2B8 (200 µg); and
D. Y2B8 (100 µCi)+C2B8 (200 µg)

Groups tested with C2B8 were given a second C2B8 injection (200 µg/mouse) seven days after the initial injection. Tumor measurements were made every two or three days using a caliper.

Preparation of treatment materials were in accordance with the following protocols:

A Preparation of Y2B8

Yttrium-[90] chloride (6 mCi) was transformed to a polypropylene tube and adjusted to pH 4.1-4.4 using metal free 2M sodium acetate. 2B8-MX-DTPA (0.3 mg in normal saline; see above for preparation of 2B8-MX-DTPA) was added and gently mixed by vortexing. After 15 min. incubation, the reaction was quenched by adding 0.05× volume 20 mM EDTA and 0.05× volume 2M sodium acetate. Radioactivity concentration was determined by diluting 5.0 µl of the reaction mixture in 2.5 ml 1× PBS containing 75 mg/ml HSA and 1 mM DTPA ("formulation buffer"); counting was accomplished by adding 10.01 µl to 20 ml of Ecolume™ scintillation cocktail. The remainder of the reactive mixture was added to 3.0 µml formulation buffer, sterile filtered and stored at 2-8° C. until used. Specific activity (14 mCi/mg at time of injection) was calculated using the radioactivity concentration and the calculated protein concentration based upon the amount of antibody added to the reaction mixture. Protein-associated radioactivity was determined using instant thin-layer chromatography. Radioincorporation was 95%. Y2B8 was diluted in formulation buffer immediately before use and sterile-filtered (final radioactivity concentration was 1.0 mCi/ml).

B. Preparation of C2B8

C2B8 was prepared as described above. C2B8 was provided as a sterile reagent in normal saline at 5.0 mg/ml. Prior to injection, the C2B8 was diluted in normal saline to 2.0 mg/ml and sterile filtered.

C. Results

Following treatment, tumor size was expressed as a product of length and width, and measurements were taken on the days indicated in FIG. 11 (Y2B8 vs. Saline); FIG. 12 (C2B8 vs. Saline); and FIG. 13 (Y2B8 +C2B8 vs. Saline). Standard error was also determined.

As indicated in FIG. 13, the combination of Y2B8 and C2B8 exhibited tumoricidal effects comparable to the effects evidenced by either Y2B8 or C2B8.

V. Alternative Therapy Strategies

Alternative therapeutic strategies recognized in view of the foregoing examples are evident. One such strategy employs the use of a therapeutic dose of C2B8 followed within about one week with a combination of either 2B8 and radioabeled 2B8 (eg Y2B8); or 2B8, C2B8 and, eg Y2B8; or C2B8 and, eg Y2B8. An additional strategy is utilization of radiolabeled C2B8—such a strategy allows for utilization of the benefits of the immunologically active portion of C2B8 plus those benefits associated with a radiolabel. Preferred radiolabels include yttrium-90 given the larger circulating half-life of C2B8 versus the murine antibody 2B8. Because of the ability of C2B8 to deplete B-cells, and the benefits to be derived from the use of a radiolabel, a preferred alternative strategy is to treat the patient with C2B8 (either with a single dose or multiple doses) such that most, if not all, peripheral B cells have been depleted. This would then be followed with the use of radiolabeled 2B8; because of the depletion of peripheral B cells, the radiolabeled 2B8 stands an increased chance of targeting tumor cells. Iodine [131] labeled 2B8 is preferably utilized, given the types of results reported in the literature with this label (see Kaminski). An alternative preference involves the use of a radiolabeled 2B8 (or C2B8) first in an effort to increase the permeability of a tumor, followed by single or multiple treatments with C2B8; the intent of this strategy is to increase the chances of the C2B8 in getting both outside and inside the tumor mass. A further strategy involved the use of chemotherapeutic agenst in combination with C2B8. These strategies include so-called "staggered" treatments, ie, treatment with chemo-therapeutic agent, followed by treatment with C2B8, followed by a repetition of this protocol. Alternatively, initial treatment with a single or multiple doses of C2B8, thereafter followed with chemotherapeutic treatment, is viable. Preferred chemotherapeutic agents include, but are not limited to: cyclophlsphamide; doxorubicin; vincristine; and prednisone, See Armitage, J. O. et al., *Cancer* 50:1695 (1982), incorporated herein by reference.

The foregoing alternative therapy strategies are not intended to be limiting, but rather are presented as being representative.

VI. Deposit Information

Anti-CD20 in TCAE 8 (transformed in *E. coli* for purposes of deposit) was deposited with the American Type Culture Collection (ATCC), 12301 Parklawn Drive, Rockville, Md., 20852, under the provisions of the Budapest Treaty for the International Recognition of the Deposit of Microorganisms for the Purpose of Patent Procedure ("Budapest Treaty"). The microorganism was tested by the ATCC on Nov. 9, 1992, and determined to be viable on that date. The ATCC has assigned this microorganism for the following ATCC deposit number: ATCC 69119 (anti-CD20 in TCAE 8). Hybridoma 2B8 was deposited with the ATCC on Jun. 22, 1993 under the provisions of the Budapest Treaty. The viability of the culture was determined on Jun. 25, 1993 and the ATCC has assigned this hybridoma the following ATCC deposit number: HB 11388.

SEQUENCE LISTING

```
(1) GENERAL INFORMATION:

(iii) NUMBER OF SEQUENCES: 9

(2) INFORMATION FOR SEQ ID NO: 1:

(i) SEQUENCE CHARACTERISTICS:
        (A) LENGTH: 27 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 1:

27

(2) INFORMATION FOR SEQ ID NO: 2:
            se pairs
        (B) TYPE: nucleic acid
        (C) STRANDEDNESS: single
        (D) TOPOLOGY: circular (ii) MOLECULE TYPE: DNA (genomic)

(iii) HYPOTHETICAL: NO (iv) ANTI-SENSE: NO (xi) SEQUENCE DESCRIPTION: SEQ ID NO: 2:

CCGCTCTAGG CCTCCAAAAA AGCCTCCTCA CTACTTCTGG AATAGCTCAG AATAGCTCAG        60

AGGCCGAGGC GGCCTCGGCC TCTGCATAAA TAAAAAAAAT TAGTCAGCCA TGCATGGGGC       120

GGAGAATGGG CGGAACTGGG CGGAGTTAGG GGCGGGATGG GCGGAGTTAG GGGCGGGACT       180

ATGGTTGCTG ACTAATTGAG ATGCATGCTT TGCATACTTC TGCCTGCTGG GGAGCCTGGG       240

GACTTTCCAC ACCTGGTTGC TGACTAATTG AGATGCATGC TTTGCATACT TCTGCCTGCT       300

GGGGAGCCTG GGACTTTCC ACACCCTAAC TGACACACAT TCCACAGAAT TAATTCCCCT       360

AGTTATTAAT AGTAATCAAT TACGGGGTCA TTAGTTCATA GCCCATATAT GGAGTTCCGC       420

GTTACATAAC TTACGGTAAA TGGCCCGCCT GGCTGACCGC CCAACGACCC CCGCCCATTG       480

ACGTCAATAA TGACGTATGT TCCCATAGTA ACGCCAATAG GGACTTTCCA TTGACGTCAA       540

TGGGTGGACT ATTTACGGTA AACTGCCCAC TTGGCAGTAC ATCAAGTGTA TCATATGCCA       600

AGTACGCCCC CTATTGACGT CAATGACGGT AAATGGCCCG CCTGGCATTA TGCCCAGTAC       660

ATGACCTTAT GGGACTTTCC TACTTGGCAG TACATCTACG TATTAGTCAT CGCTATTACC       720

ATGGTGATGC GGTTTTGGCA GTACATCAAT GGGCGTGGAT AGCGGTTTGA CTCACGGGGA       780
```

```
TTTCCAAGTC TCCACCCCAT TGACGTCAAT GGGAGTTTGT TTTGGCACCA AAATCAACGG     840

GACTTTCCAA AATGTCGTAA CAACTCCGCC CCATTGACGC AAATGGGCGG TAGGCGTGTA     900

CGGTGGGAGG TCTATATAAG CAGAGCTGGG TACGTGAACC GTCAGATCGC CTGGAGACGC     960

CATCACAGAT CTCTCACCAT GAGGGTCCCC GCTCAGCTCC TGGGGCTCCT GCTGCTCTGG    1020

CTCCCAGGTG CACGATGTGA TGGTACCAAG GTGGAAATCA AACGTACGGT GGCTGCACCA    1080

TCTGTCTTCA TCTTCCCGCC ATCTGATGAG CAGTTGAAAT CTGGAACTGC CTCTGTTGTG    1140

TGCCTGCTGA ATAACTTCTA TCCCAGAGAG GCCAAAGTAC AGTGGAAGGT GGATAACGCC    1200

CTCCAATCGG GTAACTCCCA GGAGAGTGTC ACAGAGCAGG ACAGCAAGGA CAGCACCTAC    1260

AGCCTCAGCA GCACCCTGAC GCTGAGCAAA GCAGACTACG AGAAACACAA AGTCTACGCC    1320

TGCGAAGTCA CCCATCAGGG CCTGAGCTCG CCCGTCACAA AGAGCTTCAA CAGGGGAGAG    1380

TGTTGAATTC AGATCCGTTA ACGGTTACCA ACTACCTAGA CTGGATTCGT GACAACATGC    1440

GGCCGTGATA TCTACGTATG ATCAGCCTCG ACTGTGCCTT CTAGTTGCCA GCCATCTGTT    1500

GTTTGCCCCT CCCCCGTGCC TTCCTTGACC CTGGAAGGTG CCACTCCCAC TGTCCTTTCC    1560

TAATAAAATG AGGAAATTGC ATCGCATTGT CTGAGTAGGT GTCATTCTAT TCTGGGGGGT    1620

GGGGTGGGGC AGGACAGCAA GGGGGAGGAT TGGGAAGACA ATAGCAGGCA TGCTGGGGAT    1680

GCGGTGGGCT CTATGGAACC AGCTGGGGCT CGACAGCTAT GCCAAGTACG CCCCCTATTG    1740

ACGTCAATGA CGGTAAATGG CCCGCCTGGC ATTATGCCCA GTACATGACC TTATGGGACT    1800

TTCCTACTTG GCAGTACATC TACGTATTAG TCATCGCTAT TACCATGGTG ATGCGGTTTT    1860

GGCAGTACAT CAATGGGCGT GGATAGCGGT TTGACTCACG GGGATTTCCA AGTCTCCACC    1920

CCATTGACGT CAATGGGAGT TTGTTTTGGC ACCAAAATCA ACGGGACTTT CCAAAATGTC    1980

GTAACAACTC CGCCCCATTG ACGCAAATGG GCGGTAGGCG TGTACGGTGG GAGGTCTATA    2040

TAAGCAGAGC TGGGTACGTC CTCACATTCA GTGATCAGCA CTGAACACAG ACCCGTCGAC    2100

ATGGGTTGGA GCCTCATCTT GCTCTTCCTT GTCGCTGTTG CTACGCGTGT CGCTAGCACC    2160

AAGGGCCCAT CGGTCTTCCC CCTGGCACCC TCCTCCAAGA GCACCTCTGG GGGCACAGCG    2220

GCCCTGGGCT GCCTGGTCAA GGACTACTTC CCCGAACCGG TGACGGTGTC GTGGAACTCA    2280

GGCGCCCTGA CCAGCGGCGT GCACACCTTC CCGGCTGTCC TACAGTCCTC AGGACTCTAC    2340

TCCCTCAGCA GCGTGGTGAC CGTGCCCTCC AGCAGCTTGG GCACCCAGAC CTACATCTGC    2400

AACGTGAATC ACAAGCCCAG CAACACCAAG GTGGACAAGA AAGCAGAGCC CAAATCTTGT    2460

GACAAAACTC ACACATGCCC ACCGTGCCCA GCACCTGAAC TCCTGGGGGG ACCGTCAGTC    2520

TTCCTCTTCC CCCCAAAACC CAAGGACACC CTCATGATCT CCCGGACCCC TGAGGTCACA    2580

TGCGTGGTGG TGGACGTGAG CCACGAAGAC CCTGAGGTCA AGTTCAACTG GTACGTGGAC    2640

GGCGTGGAGG TGCATAATGC CAAGACAAAG CCGCGGGAGG AGCAGTACAA CAGCACGTAC    2700

CGTGTGGTCA GCGTCCTCAC CGTCCTGCAC CAGGACTGGC TGAATGGCAA GGACTACAAG    2760

TGCAAGGTCT CCAACAAAGC CCTCCCAGCC CCCATCGAGA AAACCATCTC CAAAGCCAAA    2820

GGGCAGCCCC GAGAACCACA GGTGTACACC CTGCCCCCAT CCCGGGATGA GCTGACCAGG    2880

AACCAGGTCA GCCTGACCTG CCTGGTCAAA GGCTTCTATC CAGCGACAT CGCCGTGGAG    2940

TGGGAGAGCA ATGGGCAGCC GGAGAACAAC TACAAGACCA CGCCTCCCGT GCTGGACTCC    3000

GACGGCTCCT TCTTCCTCTA CAGCAAGCTC ACCGTGGACA AGAGCAGGTG GCAGCAGGGG    3060

AACGTCTTCT CATGCTCCGT GATGCATGAG GCTCTGCACA ACCACTACAC GCAGAAGAGC    3120
```

```
CTCTCCCTGT CTCCGGGTAA ATGAGGATCC GTTAACGGTT ACCAACTACC TAGACTGGAT    3180
TCGTGACAAC ATGCGGCCGT GATATCTACG TATGATCAGC CTCGACTGTG CCTTCTAGTT    3240
GCCAGCCATC TGTTGTTTGC CCCTCCCCCG TGCCTTCCTT GACCCTGGAA GGTGCCACTC    3300
CCACTGTCCT TTCCTAATAA AATGAGGAAA TTGCATCGCA TTGTCTGAGT AGGTGTCATT    3360
CTATTCTGGG GGGTGGGGTG GGGCAGGACA GCAAGGGGGA GGATTGGGAA GACAATAGCA    3420
GGCATGCTGG GGATGCGGTG GGCTCTATGG AACCAGCTGG GGCTCGACAG CGCTGGATCT    3480
CCCGATCCCC AGCTTTGCTT CTCAATTTCT TATTTGCATA ATGAGAAAAA AGGAAAATT     3540
AATTTTAACA CCAATTCAGT AGTTGATTGA GCAAATGCGT TGCCAAAAAG GATGCTTTAG    3600
AGACAGTGTT CTCTGCACAG ATAAGGACAA ACATTATTCA GAGGGAGTAC CCAGAGCTGA    3660
GACTCCTAAG CCAGTGAGTG GCACAGCATT CTAGGGAGAA ATATGCTTGT CATCACCGAA    3720
GCCTGATTCC GTAGAGCCAC ACCTTGGTAA GGGCCAATCT GCTCACACAG GATAGAGAGG    3780
GCAGGAGCCA GGGCAGAGCA TATAAGGTGA GGTAGGATCA GTTGCTCCTC ACATTTGCTT    3840
CTGACATAGT TGTGTTGGGA GCTTGGATAG CTTGGACAGC TCAGGGCTGC GATTTCGCGC    3900
CAAACTTGAC GGCAATCCTA GCGTGAAGGC TGGTAGGATT TTATCCCCGC TGCCATCATG    3960
GTTCGACCAT TGAACTGCAT CGTCGCCGTG TCCCAAAATA TGGGGATTGG CAAGAACGGA    4020
GACCTACCCT GGCCTCCGCT CAGGAACGAG TTCAAGTACT TCCAAAGAAT GACCACAACC    4080
TCTTCAGTGG AAGGTAAACA GAATCTGGTG ATTATGGGTA GGAAAACCTG GTTCTCCATT    4140
CCTGAGAACA ATCGACCTTT AAAGGACAGA ATTAATATAG TTCTCAGTAG AGAACTCAAA    4200
GAACCACCAC GAGGAGCTCA TTTTCTTGCC AAAAGTTTGG ATGATGCCTT AAGACTTATT    4260
GAACAACCGG AATTGGCAAG TAAAGTAGAC ATGGTTTGGA TAGTCGGAGG CAGTTCTGTT    4320
TACCAGGAAG CCATGAATCA ACCAGGCCAC CTTAGACTCT TTGTGACAAG GATCATGCAG    4380
GAATTTGAAA GTGACACGTT TTTCCCAGAA ATTGATTTGG GGAAATATAA ACTTCTCCCA    4440
GAATACCCAG GCGTCCTCTC TGAGGTCCAG GAGGAAAAAG GCATCAAGTA TAAGTTTGAA    4500
GTCTACGAGA AGAAAGACTA ACAGGAAGAT GCTTTCAAGT CTCTGCTCC CCTCCTAAAG    4560
TCATGCATTT TTATAAGACC ATGGGACTTT TGCTGGCTTT AGATCAGCCT CGACTGTGCC    4620
TTCTAGTTGC CAGCCATCTG TTGTTTGCCC CTCCCCGTG CCTTCCTTGA CCCTGGAAGG    4680
TGCCACTCCC ACTGTCCTTT CCTAATAAAA TGAGGAAATT GCATCGCATT GTCTGAGTAG    4740
GTGTCATTCT ATTCTGGGGG GTGGGGTGGG GCAGGACAGC AAGGGGGAGG ATTGGGAAGA    4800
CAATAGCAGG CATGCTGGGG ATGCGGTGGG CTCTATGGAA CCAGCTGGGG CTCGAGCTAC    4860
TAGCTTTGCT TCTCAATTTC TTATTTGCAT AATGAGAAAA AAGGAAAAT  TAATTTTAAC    4920
ACCAATTCAG TAGTTGATTG AGCAAATGCG TTGCCAAAAA GGATGCTTTA GAGACAGTGT    4980
TCTCTGCACA GATAAGGACA AACATTATTC AGAGGGAGTA CCCAGAGCTG AGACTCCTAA    5040
GCCAGTGAGT GGCACAGCAT TCTAGGGAGA AATATGCTTG TCATCACCGA AGCCTGATTC    5100
CGTAGAGCCA CACCTTGGTA AGGGCCAATC TGCTCACACA GGATAGAGAG GCAGGAGCC     5160
AGGGCAGAGC ATATAAGGTG AGGTAGGATC AGTTGCTCCT CACATTTGCT CTGACATAG     5220
TTGTGTTGGG AGCTTGGATC GATCCTCTAT GGTTGAACAA GATGGATTGC ACGCAGGTTC    5280
TCCGGCCGCT TGGGTGGAGA GGCTATTCGG CTATGACTGG GCACAACAGA CAATCGGCTG    5340
CTCTGATGCC GCCGTGTTCC GGCTGTCAGC GCAGGGGCGC CCGGTTCTTT TGTCAAGAC     5400
CGACCTGTCC GGTGCCCTGA ATGAACTGCA GGACGAGGCA GCGCGGCTAT CGTGGCTGGC    5460
CACGACGGGC GTTCCTTGCG CAGCTGTGCT CGACGTTGTC ACTGAAGCGG GAAGGGACTG    5520
```

```
GCTGCTATTG GGCGAAGTGC CGGGGCAGGA TCTCCTGTCA TCTCACCTTG CTCCTGCCGA    5580

GAAAGTATCC ATCATGGCTG ATGCAATGCG GCGGCTGCAT ACGCTTGATC CGGCTACCTG    5640

CCCATTCGAC CACCAAGCGA ACATCGCAT CGAGCGAGCA CGTACTCGGA TGGAAGCCGG     5700

TCTTGTCGAT CAGGATGATC TGGACGAAGA GCATCAGGGG CTCGCGCCAG CCGAACTGTT    5760

CGCCAGGCTC AAGGCGCGCA TGCCCGACGG CGAGGATCTC GTCGTGACCC ATGGCGATGC    5820

CTGCTTGCCG AATATCATGG TGGAAAATGG CCGCTTTTCT GGATTCATCG ACTGTGGCCG    5880

GCTGGGTGTG GCGGACCGCT ATCAGGACAT AGCGTTGGCT ACCCGTGATA TTGCTGAAGA    5940

GCTTGGCGGC GAATGGGCTG ACCGCTTCCT CGTGCTTTAC GGTATCGCCG CTTCCCGATT    6000

CGCAGCGCAT CGCCTTCTAT CGCCTTCTTG ACGAGTTCTT CTGAGCGGGA CTCTGGGGTT    6060

CGAAATGACC GACCAAGCGA CGCCCAACCT GCCATCACGA GATTTCGATT CCACCGCCGC    6120

CTTCTATGAA AGGTTGGGCT TCGGAATCGT TTTCCGGGAC GCCGGCTGGA TGATCCTCCA    6180

GCGCGGGGAT CTCATGCTGG AGTTCTTCGC CCACCCCAAC TTGTTTATTG CAGCTTATAA    6240

TGGTTACAAA TAAAGCAATA GCATCACAAA TTTCACAAAT AAAGCATTTT TTCACTGCA     6300

TTCTAGTTGT GGTTTGTCCA AACTCATCAA TCTATCTTAT CATGTCTGGA TCGCGGCCGC    6360

GATCCCGTCG AGAGCTTGGC GTAATCATGG TCATAGCTGT TTCCTGTGTG AAATTGTTAT    6420

CCGCTCACAA TTCCACACAA CATACGAGCC GGAGCATAAA GTGTAAAGCC TGGGGTGCCT    6480

AATGAGTGAG CTAACTCACA TTAATTGCGT TGCGCTCACT GCCCGCTTTC CAGTCGGGAA    6540

ACCTGTCGTG CCAGCTGCAT TAATGAATCG GCCAACGCGC GGGGAGAGGC GGTTTGCGTA    6600

TTGGGCGCTC TTCCGCTTCC TCGCTCACTG ACTCGCTGCG CTCGGTCGTT CGGCTGCGGC    6660

GAGCGGTATC AGCTCACTCA AAGGCGGTAA TACGGTTATC CACAGAATCA GGGGATAACG    6720

CAGGAAAGAA CATGTGAGCA AAAGGCCAGC AAAAGGCCAG GAACCGTAAA AAGGCCGCGT    6780

TGCTGGCGTT TTTCCATAGG CTCCGCCCCC CTGACGAGCA TCACAAAAAT CGACGCTCAA    6840

GTCAGAGGTG GCGAAACCCG ACAGGACTAT AAAGATACCA GGCGTTTCCC CCTGGAAGCT    6900

CCCTCGTGCG CTCTCCTGTT CCGACCCTGC CGCTTACCGG ATACCTGTCC GCCTTTCTCC    6960

CTTCGGGAAG CGTGGCGCTT TCTCAATGCT CACGCTGTAG GTATCTCAGT TCGGTGTAGG    7020

TCGTTCGCTC CAAGCTGGGC TGTGTGCACG AACCCCCCGT TCAGCCCGAC CGCTGCGCCT    7080

TATCCGGTAA CTATCGTCTT GAGTCCAACC CGGTAAGACA CGACTTATCG CCACTGGCAG    7140

CAGCCACTGG TAACAGGATT AGCAGAGCGA GGTATGTAGG CGGTGCTACA GAGTTCTTGA    7200

AGTGGTGGCC TAACTACGGC TACACTAGAA GGACAGTATT TGGTATCTGC GCTCTGCTGA    7260

AGCCAGTTAC CTTCGGAAAA AGAGTTGGTA GCTCTTGATC CGGCAAACAA ACCACCGCTG    7320

GTAGCGGTGG TTTTTTTGTT TGCAAGCAGC AGATTACGCG CAGAAAAAAA GGATCTCAAG    7380

AAGATCCTTT GATCTTTTCT ACGGGGTCTG ACGCTCAGTG GAACGAAAAC TCACGTTAAG    7440

GGATTTTGGT CATGAGATTA TCAAAAGGA TCTTCACCTA GATCCTTTTA AATTAAAAAT     7500

GAAGTTTTAA ATCAATCTAA AGTATATATG AGTAAACTTG GTCTGACAGT TACCAATGCT    7560

TAATCAGTGA GGCACCTATC TCAGCGATCT GTCTATTTCG TTCATCCATA GTTGCCTGAC    7620

TCCCCGTCGT GTAGATAACT ACGATACGGG AGGGCTTACC ATCTGGCCCC AGTGCTGCAA    7680

TGATACCGCG AGACCCACGC TCACCGGCTC CAGATTTATC AGCAATAAAC CAGCCAGCCG    7740

GAAGGGCCGA GCGCAGAAGT GGTCCTGCAA CTTTATCCGC CTCCATCCAG TCTATTAATT    7800

GTTGCCGGGA AGCTAGAGTA AGTAGTTCGC CAGTTAATAG TTTGCGCAAC GTTGTTGCCA    7860
```

```
TTGCTACAGG CATCGTGGTG TCACGCTCGT CGTTTGGTAT GGCTTCATTC AGCTCCGGTT   7920

CCCAACGATC AAGGCGAGTT ACATGATCCC CCATGTTGTG CAAAAAAGCG GTTAGCTCCT   7980

TCGGTCCTCC GATCGTTGTC AGAAGTAAGT TGGCCGCAGT GTTATCACTC ATGGTTATGG   8040

CAGCACTGCA TAATTCTCTT ACTGTCATGC CATCCGTAAG ATGCTTTTCT GTGACTGGTG   8100

AGTACTCAAC CAAGTCATTC TGAGAATAGT GTATGCGGCG ACCGAGTTGC TCTTGCCCGG   8160

CGTCAATACG GGATAATACC GCGCCACATA GCAGAACTTT AAAAGTGCTC ATCATTGGAA   8220

AACGTTCTTC GGGGCGAAAA CTCTCAAGGA TCTTACCGCT GTTGAGATCC AGTTCGATGT   8280

AACCCACTCG TGCACCCAAC TGATCTTCAG CATCTTTTAC TTTCACCAGC GTTTCTGGGT   8340

GAGCAAAAAC AGGAAGGCAA AATGCCGCAA AAAGGGAAT AAGGGCGACA CGGAAATGTT   8400

GAATACTCAT ACTCTTCCTT TTTCAATATT ATTGAAGCAT TTATCAGGGT TATTGTCTCA   8460

TGAGCGGATA CATATTTGAA TGTATTTAGA AAAATAAACA AATAGGGGTT CCGCGCACAT   8520

TTCCCCGAAA AGTGCCACCT                                                8540
```

(2) INFORMATION FOR SEQ ID NO: 3:
         ase pairs
     (B) TYPE: nucleic acid
     (C) STRANDEDNESS: single
     (D) TOPOLOGY: circular (ii) MOLECULE TYPE: DNA (genomic)

(iii) HYPOTHETICAL: NO (iv) ANTI-SENSE: NO (xi) SEQUENCE DESCRIPTION: SEQ ID NO: 3:

```
CCGCTCTAGG CCTCCAAAAA AGCCTCCTCA CTACTTCTGG AATAGCTCAG AATAGCTCAG     60

AGGCCGAGGC GGCCTCGGCC TCTGCATAAA TAAAAAAAAT TAGTCAGCCA TGCATGGGGC    120

GGAGAATGGG CGGAACTGGG CGGAGTTAGG GGCGGGATGG GCGGAGTTAG GGGCGGGACT    180

ATGGTTGCTG ACTAATTGAG ATGCATGCTT TGCATACTTC TGCCTGCTGG GGAGCCTGGG    240

GACTTTCCAC ACCTGGTTGC TGACTAATTG AGATGCATGC TTTGCATACT TCTGCCTGCT    300

GGGGAGCCTG GGACTTTCC ACACCCTAAC TGACACACAT TCCACAGAAT TAATTCCCCT    360

AGTTATTAAT AGTAATCAAT TACGGGGTCA TTAGTTCATA GCCCATATAT GGAGTTCCGC    420

GTTACATAAC TTACGGTAAA TGGCCCGCCT GGCTGACCGC CCAACGACCC CCGCCCATTG    480

ACGTCAATAA TGACGTATGT TCCCATAGTA ACGCCAATAG GGACTTTCCA TTGACGTCAA    540

TGGGTGGACT ATTTACGGTA AACTGCCCAC TTGGCAGTAC ATCAAGTGTA TCATATGCCA    600

AGTACGCCCC CTATTGACGT CAATGACGGT AAATGGCCCG CCTGGCATTA TGCCCAGTAC    660

ATGACCTTAT GGGACTTTCC TACTTGGCAG TACATCTACG TATTAGTCAT CGCTATTACC    720

ATGGTGATGC GGTTTTGGCA GTACATCAAT GGGCGTGGAT ACCGGTTTGA CTCACGCGGA    780

TTTCCAAGTC TCCACCCCAT TGACGTCAAT GGGAGTTTGT TTTGGCACCA AAATCAACGG    840

GACTTTCCAA AATGTCGTAA CAACTCCGCC CCATTGACGC AAATGGGCGG TAGGCGTGTA    900

CGGTGGGAGG TCTATATAAG CAGAGCTGGG TACGTGAACC GTCAGATCGC CTGGAGACGC    960

CATCACAGAT CTCTCACTAT GGATTTTCAG GTGCAGATTA TCAGCTTCCT GCTAATCAGT   1020

GCTTCAGTCA TAATGTCCAG AGGACAAATT GTTCTCTCCC AGTCTCCAGC AATCCTGTCT   1080

GCATCTCCAG GGGAGAAGGT CACAATGACT TGCAGGGCCA GCTCAAGTGT AAGTTACATC   1140

CACTGGTTCC AGCAGAAGCC AGGATCCTCC CCCAAACCCT GGATTTATGC CACATCCAAC   1200
```

```
CTGGCTTCTG GAGTCCCTGT TCGCTTCAGT GGCAGTGGGT CTGGGACTTC TTACTCTCTC    1260
ACAATCAGCA GAGTGGAGGC TGAAGATGCT GCCACTTATT ACTGCCAGCA GTGGACTAGT    1320
AACCCACCCA CGTTCGGAGG GGGGACCAAG CTGGAAATCA AACGTACGGT GGCTGCACCA    1380
TCTGTCTTCA TCTTCCCGCC ATCTGATGAG CAGTTGAAAT CTGGAACTGC CTCTGTTGTG    1440
TGCCTGCTGA ATAACTTCTA TCCCAGAGAG GCCAAAGTAC AGTGGAAGGT GGATAACGCC    1500
CTCCAATCGG GTAACTCCCA GGAGAGTGTC ACAGAGCAGG ACAGCAAGGA CAGCACCTAC    1560
AGCCTCAGCA GCACCCTGAC GCTGAGCAAA GCAGACTACG AGAAACACAA AGTCTACGCC    1620
TGCGAAGTCA CCCATCAGGG CCTGAGCTCG CCCGTCACAA AGAGCTTCAA CAGGGGAGAG    1680
TGTTGAATTC AGATCCGTTA ACGGTTACCA ACTACCTAGA CTGGATTCGT GACAACATGC    1740
GGCCGTGATA TCTACGTATG ATCAGCCTCG ACTGTGCCTT CTAGTTGCCA GCCATCTGTT    1800
GTTTGCCCCT CCCCCGTGCC TTCCTTGACC CTGGAAGGTG CCACTCCCAC TGTCCTTTCC    1860
TAATAAAATG AGGAAATTGC ATCGCATTGT CTGAGTAGGT GTCATTCTAT TCTGGGGGGT    1920
GGGGTGGGGC AGGACAGCAA GGGGGAGGAT TGGGAAGACA ATAGCAGGCA TGCTGGGGAT    1980
GCGGTGGGCT CTATGGAACC AGCTGGGGCT CGACAGCTAT GCCAAGTACG CCCCCTATTG    2040
ACGTCAATGA CGGTAAATGG CCCGCCTGGC ATTATGCCCA GTACATGACC TTATGGGACT    2100
TTCCTACTTG GCAGTACATC TACGTATTAG TCATCGCTAT TACCATGGTG ATGCGGTTTT    2160
GGCAGTACAT CAATGGGCGT GGATAGCGGT TTGACTCACG GGGATTTCCA AGTCTCCACC    2220
CCATTGACGT CAATGGGAGT TTGTTTTGGC ACCAAAATCA ACGGGACTTT CCAAAATGTC    2280
GTAACAACTC CGCCCCATTG ACGCAAATGG GCGGTAGGCG TGTACGGTGG GAGGTCTATA    2340
TAAGCAGAGC TGGGTACGTC CTCACATTCA GTGATCAGCA CTGAACACAG ACCCGTCGAC    2400
ATGGGTTGGA GCCTCATCTT GCTCTTCCTT GTCGCTGTTG CTACGCGTGT CCTGTCCCAG    2460
GTACAACTGC AGCAGCCTGG GGCTGAGCTG GTGAAGCCTG GGGCCTCAGT GAAGATGTCC    2520
TGCAAGGCTT CTGGCTACAC ATTTACCAGT TACAATATGC ACTGGGTAAA ACAGACACCT    2580
GGTCGGGGCC TGGAATGGAT TGGAGCTATT TATCCCGGAA ATGGTGATAC TTCCTACAAT    2640
CAGAAGTTCA AGGCAAGGC CACATTGACT GCAGACAAAT CCTCCAGCAC AGCCTACATG    2700
CAGCTCAGCA GCCTGACATC TGAGGACTCT GCGGTCTATT ACTGTGCAAG ATCGACTTAC    2760
TACGGCGGTG ACTGGTACTT CAATGTCTGG GGCGCAGGGA CCACGGTCAC CGTCTCTGCA    2820
GCTAGCACCA AGGGCCCATC GGTCTTCCCC CTGGCACCCT CCTCCAAGAG CACCTCTGGG    2880
GGCACAGCGG CCCTGGGCTG CCTGGTCAAG GACTACTTCC CCGAACCGGT GACGGTGTCG    2940
TGGAACTCAG GCGCCCTGAC CAGCGGCGTG CACACCTTCC CGGCTGTCCT ACAGTCCTCA    3000
GGACTCTACT CCCTCAGCAG CGTGGTGACC GTGCCCTCCA GCAGCTTGGG CACCCAGACC    3060
TACATCTGCA ACGTGAATCA CAAGCCCAGC AACACCAAGG TGGACAAGAA AGCAGAGCCC    3120
AAATCTTGTG ACAAAACTCA CACATGCCCA CCGTGCCCAG CACCTGAACT CCTGGGGGGA    3180
CCGTCAGTCT TCCTCTTCCC CCCAAAACCC AAGGACACCC TCATGATCTC CCGGACCCCT    3240
GAGGTCACAT GCGTGGTGGT GGACGTGAGC CACGAAGACC CTGAGGTCAA GTTCAACTGG    3300
TACGTGGACG GCGTGGAGGT GCATAATGCC AAGACAAAGC CGCGGGAGGA GCAGTACAAC    3360
AGCACGTACC GTGTGGTCAG CGTCCTCACC GTCCTGCACC AGGACTGGCT GAATGGCAAG    3420
GAGTACAAGT GCAAGGTCTC CAACAAAGCC CTCCCAGCCC CCATCGAGAA AACCATCTCC    3480
AAAGCCAAAG GGCAGCCCCG AGAACCACAG GTGTACACCC TGCCCCCATC CCGGGATGAG    3540
CTGACCAAGA ACCAGGTCAG CCTGACCTGC CTGGTCAAAG GCTTCTATCC CAGCGACATC    3600
```

```
GCCGTGGAGT GGGAGAGCAA TGGGCAGCCG GAGAACAACT ACAAGACCAC GCCTCCCGTG    3660

CTGGACTCCG ACGGCTCCTT CTTCCTCTAC AGCAAGCTCA CCGTGGACAA GAGCAGGTGG    3720

CAGCAGGGGA ACGTCTTCTC ATGCTCCGTG ATGCATGAGG CTCTGCACAA CCACTACACG    3780

CAGAAGAGCC TCTCCCTGTC TCCGGGTAAA TGAGGATCCG TTAACGGTTA CCAACTACCT    3840

AGACTGGATT CGTGACAACA TGCGGCCGTG ATATCTACGT ATGATCAGCC TCGACTGTGC    3900

CTTCTAGTTG CCAGCCATCT GTTGTTTGCC CCTCCCCCGT GCCTTCCTTG ACCCTGGAAG    3960

GTGCCACTCC CACTGTCCTT TCCTAATAAA ATGAGGAAAT TGCATCGCAT TGTCTGAGTA    4020

GGTGTCATTC TATTCTGGGG GGTGGGGTGG GGCAGGACAG CAAGGGGGAG GATTGGGAAG    4080

ACAATAGCAG GCATGCTGGG GATGCGGTGG GCTCTATGGA ACCAGCTGGG GCTCGACAGC    4140

GCTGGATCTC CCGATCCCCA GCTTTGCTTC TCAATTTCTT ATTTGCATAA TGAGAAAAAA    4200

AGGAAAATTA ATTTTAACAC CAATTCAGTA GTTGATTGAG CAAATGCGTT GCCAAAAAGG    4260

ATGCTTTAGA GACAGTGTTC TCTGCACAGA TAAGGACAAA CATTATTCAG AGGGAGTACC    4320

CAGAGCTGAG ACTCCTAAGC CAGTGAGTGG CACAGCATTC TAGGGAGAAA TATGCTTGTC    4380

ATCACCGAAG CCTGATTCCG TAGAGCCACA CCTTGGTAAG GGCCAATCTG CTCACACAGG    4440

ATAGAGAGGG CAGGAGCCAG GGCAGAGCAT ATAAGGTGAG GTAGGATCAG TTGCTCCTCA    4500

CATTTGCTTC TGACATAGTT GTGTTGGGAG CTTGGATAGC TTGGACAGCT CAGGGCTGCG    4560

ATTTCGCGCC AAACTTGACG GCAATCCTAG CGTGAAGGCT GGTAGGATTT TATCCCCGCT    4620

GCCATCATGG TTCGACCATT GAACTGCATC GTCGCCGTGT CCCAAAATAT GGGGATTGGC    4680

AAGAACGGAG ACCTACCCTG GCCTCCGCTC AGGAACGAGT TCAAGTACTT CCAAAGAATG    4740

ACCACAACCT CTTCAGTGGA AGGTAAACAG AATCTGGTGA TTATGGGTAG GAAAACCTGG    4800

TTCTCCATTC CTGAGAAGAA TCGACCTTTA AAGGACAGAA TTAATATAGT TCTCAGTAGA    4860

GAACTCAAAG AACCACCACG AGGAGCTCAT TTTCTTGCCA AAAGTTTGGA TGATGCCTTA    4920

AGACTTATTG AACAACCGGA ATTGGCAAGT AAAGTAGACA TGGTTTGGAT AGTCGGAGGC    4980

AGTTCTGTTT ACCAGGAAGC CATGAATCAA CCAGGCCACC TTAGACTCTT TGTGACAAGG    5040

ATCATGCAGG AATTTGAAAG TGACACGTTT TTCCCAGAAA TTGATTTGGG GAAATATAAA    5100

CTTCTCCCAG AATACCCAGG CGTCCTCTCT GAGGTCCAGG AGGAAAAAGG CATCAAGTAT    5160

AAGTTTGAAG TCTACGAGAA GAAAGACTAA CAGGAAGATG CTTTCAAGTT CTCTGCTCCC    5220

CTCCTAAAGC TATGCATTTT TATAAGACCA TGGGACTTTT GCTGGCTTTA GATCAGCCTC    5280

GACTGTGCCT TCTAGTTGCC AGCCATCTGT TGTTTGCCCC TCCCCCGTGC CTTCCTTGAC    5340

CCTGGAAGGT GCCACTCCCA CTGTCCTTTC CTAATAAAAT GAGGAAATTG CATCGCATTG    5400

TCTGAGTAGG TGTCATTCTA TTCTGGGGGG TGGGGTGGGG CAGGACAGCA AGGGGGAGGA    5460

TTGGGAAGAC AATAGCAGGC ATGCTGGGGA TGCGGTGGGC TCTATGGAAC CAGCTGGGGC    5520

TCGAGCTACT AGCTTTGCTT CTCAATTTCT TATTTGCATA ATGAGAAAAA AAGGAAAATT    5580

AATTTTAACA CCAATTCAGT AGTTGATTGA GCAAATGCGT TGCCAAAAAG GATGCTTTAG    5640

AGACAGTGTT CTCTGCACAG ATAAGGACAA ACATTATTCA GAGGGAGTAC CCAGAGCTGA    5700

GACTCCTAAG CCAGTGAGTG GCACAGCATT CTAGGGAGAA ATATGCTTGT CATCACCGAA    5760

GCCTGATTCC GTAGAGCCAC ACCTTGGTAA GGGCCAATCT GCTCACACAG GATAGAGAGG    5820

GCAGGAGCCA GGGCAGAGCA TATAAGGTGA GGTAGGATCA GTTGCTCCTC ACATTTGCTT    5880

CTGACATAGT TGTGTTGGGA GCTTGGATCG ATCCTCTATG GTTGAACAAG ATGGATTGCA    5940
```

| | |
|---|---|
| CGCAGGTTCT CCGGCCGCTT GGGTGGAGAG GCTATTCGGC TATGACTGGG CACAACAGAC | 6000 |
| AATCGGCTGC TCTGATGCCG CCGTGTTCCG GCTGTCAGCG CAGGGGCGCC CGGTTCTTTT | 6060 |
| TGTCAAGACC GACCTGTCCG GTGCCCTGAA TGAACTGCAG GACGAGGCAG CGCGGCTATC | 6120 |
| GTGGCTGGCC ACGACGGGCG TTCCTTGCGC AGCTGTGCTC GACGTTGTCA CTGAAGCGGG | 6180 |
| AAGGGACTGG CTGCTATTGG GCGAAGTGCC GGGGCAGGAT CTCCTGTCAT CTCACCTTGC | 6240 |
| TCCTGCCGAG AAAGTATCCA TCATGGCTGA TGCAATGCGG CGGCTGCATA CGCTTGATCC | 6300 |
| GGCTACCTGC CCATTCGACC ACCAAGCGAA ACATCGCATC GAGCGAGCAC GTACTCGGAT | 6360 |
| GGAAGCCGGT CTTGTCGATC AGGATGATCT GGACGAAGAG CATCAGGGGC TCGCGCCAGC | 6420 |
| CGAACTGTTC GCCAGGCTCA AGGCGCGCAT GCCCGACGGC GAGGATCTCG TCGTGACCCA | 6480 |
| TGGCGATGCC TGCTTGCCGA ATATCATGGT GGAAAATGGC CGCTTTTCTG GATTCATCGA | 6540 |
| CTGTGGCCGG CTGGGTGTGG CGGACCGCTA TCAGGACATA GCGTTGGCTA CCCGTGATAT | 6600 |
| TGCTGAAGAG CTTGGCGGCG AATGGGCTGA CCGCTTCCTC GTGCTTTACG GTATCGCCGC | 6660 |
| TCCCGATTCG CAGCGCATCG CCTTCTATCG CCTTCTTGAC GAGTTCTTCT GAGCGGGACT | 6720 |
| CTGGGGTTCG AAATGACCGA CCAAGCGACG CCCAACCTGC CATCACGAGA TTTCGATTCC | 6780 |
| ACCGCCGCCT TCTATGAAAG GTTGGGCTTC GGAATCGTTT TCCGGGACGC CGGCTGGATG | 6840 |
| ATCCTCCAGC GCGGGGATCT CATGCTGGAG TTCTTCGCCC ACCCCAACTT GTTTATTGCA | 6900 |
| GCTTATAATG GTTACAAATA AAGCAATAGC ATCACAAATT TCACAAATAA AGCATTTTTT | 6960 |
| TCACTGCATT CTAGTTGTGG TTTGTCCAAA CTCATCAATC TATCTTATCA TGTCTGGATC | 7020 |
| GCGGCCGCGA TCCCGTCGAG AGCTTGGCGT AATCATGGTC ATAGCTGTTT CCTGTGTGAA | 7080 |
| ATTGTTATCC GCTCACAATT CCACACAACA TACGAGCCGG AAGCATAAAG TGTAAAGCCT | 7140 |
| GGGGTGCCTA ATGAGTGAGC TAACTCACAT TAATTGCGTT GCGCTCACTG CCCGCTTTCC | 7200 |
| AGTCGGGAAA CCTGTCGTGC CAGCTGCATT AATGAATCGG CCAACGCGCG GGGAGAGGCG | 7260 |
| GTTTGCGTAT TGGGCGCTCT TCCGCTTCCT CGCTCACTGA CTCGCTGCGC TCGGTCGTTC | 7320 |
| GGCTGCGGCG AGCGGTATCA GCTCACTCAA AGGCGGTAAT ACGGTTATCC ACAGAATCAG | 7380 |
| GGGATAACGC AGGAAAGAAC ATGTGAGCAA AAGGCCAGCA AAAGGCCAGG AACCGTAAAA | 7440 |
| AGGCCGCGTT GCTGGCGTTT TTCCATAGGC TCCGCCCCCC TGACGAGCAT CACAAAAATC | 7500 |
| GACGCTCAAG TCAGAGGTGG CGAAACCCGA CAGGACTATA AAGATACCAG GCGTTTCCCC | 7560 |
| CTGGAAGCTC CCTCGTGCGC TCTCCTGTTC CGACCCTGCC GCTTACCGGA TACCTGTCCG | 7620 |
| CCTTTCTCCC TTCGGGAAGC GTGGCGCTTT CTCAATGCTC ACGCTGTAGG TATCTCAGTT | 7680 |
| CGGTGTAGGT CGTTCGCTCC AAGCTGGGCT GTGTGCACGA ACCCCCCGTT CAGCCCGACC | 7740 |
| GCTGCGCCTT ATCCGGTAAC TATCGTCTTG AGTCCAACCC GGTAAGACAC GACTTATCGC | 7800 |
| CACTGGCAGC AGCCACTGGT AACAGGATTA GCAGAGCGAG GTATGTAGGC GGTGCTACAG | 7860 |
| AGTTCTTGAA GTGGTGGCCT AACTACGGCT ACACTAGAAG GACAGTATTT GGTATCTGCG | 7920 |
| CTCTGCTGAA GCCAGTTACC TTCGGAAAAA GAGTTGGTAG CTCTTGATCC GGCAAACAAA | 7980 |
| CCACCGCTGG TAGCGGTGGT TTTTTTGTTT GCAAGCAGCA GATTACGCGC AGAAAAAAAG | 8040 |
| GATCTCAAGA AGATCCTTTG ATCTTTTCTA CGGGGTCTGA CGCTCAGTGG AACGAAAACT | 8100 |
| CACGTTAAGG GATTTTGGTC ATGAGATTAT CAAAAAGGAT CTTCACCTAG ATCCTTTTAA | 8160 |
| ATTAAAAATG AAGTTTTAAA TCAATCTAAA GTATATATGA GTAAACTTGG TCTGACAGTT | 8220 |
| ACCAATGCTT AATCAGTGAG GCACCTATCT CAGCGATCTG TCTATTTCGT TCATCCATAG | 8280 |
| TTGCCTGACT CCCCGTCGTG TAGATAACTA CGATACGGGA GGGCTTACCA TCTGGCCCCA | 8340 |

-continued

```
GTGCTGCAAT GATACCGCGA GACCCACGCT CACCGGCTCC AGATTTATCA GCAATAAACC    8400

AGCCAGCCGG AAGGGCCGAG CGCAGAAGTG GTCCTGCAAC TTTATCCGCC TCCATCCAGT    8460

CTATTAATTG TTGCCGGGAA GCTAGAGTAA GTAGTTCGCC AGTTAATAGT TTGCGCAACG    8520

TTGTTGCCAT TGCTACAGGC ATCGTGGTGT CACGCTCGTC GTTTGGTATG GCTTCATTCA    8580

GCTCCGGTTC CCAACGATCA AGGCGAGTTA CATGATCCCC CATGTTGTGC AAAAAAGCGG    8640

TTAGCTCCTT CGGTCCTCCG ATCGTTGTCA GAAGTAAGTT GGCCGCAGTG TTATCACTCA    8700

TGGTTATGGC AGCACTGCAT AATTCTCTTA CTGTCATGCC ATCCGTAAGA TGCTTTTCTG    8760

TGACTGGTGA GTACTCAACC AAGTCATTCT GAGAATAGTG TATGCGGCGA CCGAGTTGCT    8820

CTTGCCCGGC GTCAATACGG GATAATACCG CGCCACATAG CAGAACTTTA AAAGTGCTCA    8880

TCATTGGAAA ACGTTCTTCG GGGCGAAAAC TCTCAAGGAT CTTACCGCTG TTGAGATCCA    8940

GTTCGATGTA ACCCACTCGT GCACCCAACT GATCTTCAGC ATCTTTTACT TTCACCAGCG    9000

TTTCTGGGTG AGCAAAAACA GGAAGGCAAA ATGCCGCAAA AAAGGGAATA AGGGCGACAC    9060

GGAAATGTTG AATACTCATA CTCTTCCTTT TTCAATATTA TTGAAGCATT TATCAGGGTT    9120

ATTGTCTCAT GAGCGGATAC ATATTTGAAT GTATTTAGAA AAATAAACAA ATAGGGGTTC    9180

CGCGCACATT TCCCCGAAAA GTGCCACCT                                    9209

(2) INFORMATION FOR SEQ ID NO: 4:
            TYPE: nucleic acid
        (C) STRANDEDNESS: single
        (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO: 4:

TCTCACCATG GATTTTCAGG TGCAGATTAT CAGCTTC                                   47

(2) INFORMATION FOR SEQ ID NO: 5:
            CE CHARACTERISTICS:
        (A) LENGTH: 30 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (iv) ANTI-SENSE: YES (xi) SEQUENCE DESCRIPTION: SEQ ID NO: 5:

TACGTTTGA TTTCCAGCTT                                                       30

(2) INFORMATION FOR SEQ ID NO: 6:
            CHARACTERISTICS:
        (A) LENGTH: 384 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (iv) ANTI-SENSE: NO
```

(ix) FEATURE:
            (A) NAME/KEY: CDS
            (B) LOCATION: 1..384

(ix) FEATURE:
            (A) NAME/KEY: mat_peptide
            (B) LOCATION: 67..384

(xi) SEQUENCE DESCRIPTION: SEQ ID NO: 6:

```
CAG ATT ATC AGC TTC CTG CTA ATC AGT GCT TCA                          48
Met Asp Phe Gln Val Gln Ile Ile Ser Phe Leu Leu Ile Ser Ala Ser
-22         -20                 -15                 -10

GTC ATA ATG TCC AGA GGG CAA ATT GTT CTC TCC CAG TCT CCA GCA ATC      96
Val Ile Met Ser Arg Gly Gln Ile Val Leu Ser Gln Ser Pro Ala Ile
     -5                  -1   1                   5                  10

CTG TCT GCA TCT CCA GGG GAG AAG GTC ACA ATG ACT TGC AGG GCC AGC     144
Leu Ser Ala Ser Pro Gly Glu Lys Val Thr Met Thr Cys Arg Ala Ser
                15                  20                  25

TCA AGT GTA AGT TAC ATC CAC TGG TTC CAG CAG AAG CCA GGA TCC TCC     192
Ser Ser Val Ser Tyr Ile His Trp Phe Gln Gln Lys Pro Gly Ser Ser
            30                  35                  40

CCC AAA CCC TGG ATT TAT GCC ACA TCC AAC CTG GCT TCT GGA GTC CCT     240
Pro Lys Pro Trp Ile Tyr Ala Thr Ser Asn Leu Ala Ser Gly Val Pro
        45                  50                  55

GTT CGC TTC AGT GGC AGT GGG TCT GGG ACT TCT TAC TCT CTC ACA ATC     288
Val Arg Phe Ser Gly Ser Gly Ser Gly Thr Ser Tyr Ser Leu Thr Ile
    60                  65                  70

AGC AGA GTG GAG GCT GAA GAT GCT GCC ACT TAT TAC TGC CAG CAG TGG     336
Ser Arg Val Glu Ala Glu Asp Ala Ala Thr Tyr Tyr Cys Gln Gln Trp
75                  80                  85                  90

ACT AGT AAC CCA CCC ACG TTC GGA GGG GGG ACC AAG CTG GAA ATC AAA     384
Thr Ser Asn Pro Pro Thr Phe Gly Gly Gly Thr Lys Leu Glu Ile Lys
                95                 100                 105
```

(2) INFORMATION FOR SEQ ID NO: 7:
    :
        (A) LENGTH: 27 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO: 7:

```
GCGTGTCCT GTCCCAG                                                    27
```

(2) INFORMATION FOR SEQ ID NO: 8:
            CHARACTERISTICS:
        (A) LENGTH: 29 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (iv) ANTI-SENSE: YES (ix) FEATURE:
            (A) NAME/KEY: misc_feature
            (B) LOCATION: 3
            (D) OTHER INFORMATION: /note= "Nucleotide 3 is N wherein N
                is G or C."

```
    (ix) FEATURE:
          (A) NAME/KEY: misc_feature
          (B) LOCATION: 18
          (D) OTHER INFORMATION: /note= "Nucleotide 18 is N wherein
              N is A or C."

(ix) FEATURE:
          (A) NAME/KEY: misc_feature
          (B) LOCATION: 19
          (D) OTHER INFORMATION: /note= "Nucleotide 19 is N wherein
              N is A or G."

(ix) FEATURE:
          (A) NAME/KEY: misc_feature
          (B) LOCATION: 25
          (D) OTHER INFORMATION: /note= "Nucleotide 25 is N wherein
              N is G or A."

(xi) SEQUENCE DESCRIPTION: SEQ ID NO: 8:

erein

N is G or A."

(2) INFORMATION FOR SEQ ID NO: 9:

(i) SEQUENCE CHARACTERISTICS:
        (A) LENGTH: 420 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (iv) ANTI-SENSE: NO (ix) FEATURE:
          (A) NAME/KEY: CDS
          (B) LOCATION: 1..420

(ix) FEATURE:
          (A) NAME/KEY: mat_peptide
          (B) LOCATION: 58..420

(xi) SEQUENCE DESCRIPTION: SEQ ID NO: 9:

xi) SEQUENCE DESCRIPTION: SEQ ID NO:9:

ATG GGT TGG AGC CTC ATC TTG CTC TTC CTT GTC GCT GTT GCT ACG CGT        48
Met Gly Trp Ser Leu Ile Leu Leu Phe Leu Val Ala Val Ala Thr Arg
-19             -15              -10              -5

GTC CTG TCC CAG GTA CAA CTG CAG CAG CCT GGG GCT GAG CTG GTG AAG        96
Val Leu Ser Gln Val Gln Leu Gln Gln Pro Gly Ala Glu Leu Val Lys
    -1   1               5                   10

CCT GGG GCC TCA GTG AAG ATG TCC TGC AAG GCT TCT GGC TAC ACA TTT       144
Pro Gly Ala Ser Val Lys Met Ser Cys Lys Ala Ser Gly Tyr Thr Phe
    15                  20                  25

ACC AGT TAC AAT ATG CAC TGG GTA AAA CAG ACA CCT GGT CGG GGC CTG       192
Thr Ser Tyr Asn Met His Trp Val Lys Gln Thr Pro Gly Arg Gly Leu
    30                  35                  40                  45

GAA TGG ATT GGA GCT ATT TAT CCC GGA AAT GGT GAT ACT TCC TAC AAT       240
Glu Trp Ile Gly Ala Ile Tyr Pro Gly Asn Gly Asp Thr Ser Tyr Asn
                    50                  55                  60

CAG AAG TTC AAA GGC AAG GCC ACA TTG ACT GCA GAC AAA TCC TCC AGC       288
Gln Lys Phe Lys Gly Lys Ala Thr Leu Thr Ala Asp Lys Ser Ser Ser
                65                  70                  75

ACA GCC TAC ATG CAG CTC AGC AGC CTG ACA TCT GAG GAC TCT GCG GTC       336
Thr Ala Tyr Met Gln Leu Ser Ser Leu Thr Ser Glu Asp Ser Ala Val
            80                  85                  90
```

-continued

```
TAT TAC TGT GCA AGA TCG ACT TAC TAC GGC GGT GAC TGG TAC TTC AAT      384
Tyr Tyr Cys Ala Arg Ser Thr Tyr Tyr Gly Gly Asp Trp Tyr Phe Asn
        95                  100                 105

GTC TGG GGC GCA GGG ACC ACG GTC ACC GTC TCT GCA                      420
Val Trp Gly Ala Gly Thr Thr Val Thr Val Ser Ala
110             115             120
```

What is claimed is:

1. A host cell comprising nucleic acid sequences encoding the light chain and the heavy chain of an immunologically active chimeric anti-CD20 antibody, wherein the sequence encoding the light chain comprises a nucleotide sequence encoding amino acid residues 23 to 128 of SEQ ID NO: 4, and the sequence encoding the heavy chain comprises a nucleotide sequence encoding amino acid residues 20 to 140 of SEQ ID NO: 6, wherein the cell is capable of expressing and secreting an immunologically active chimeric anti-CD20 antibody.

2. The host cell of claim 1 wherein the sequence encoding the light chain further comprises a nucleotide sequence encoding a human kappa light chain constant region, and the sequence encoding the heavy chain further comprises a nucleotide sequence encoding a human gamma 1 heavy chain constant region.

3. A method of making a purified antibody comprising expressing the light and heavy chains encoded by the nucleic acid sequences in the host cell of claim 1 and purifying the antibody produced by the host cell.

4. The method of claim 3 further comprising combining the purified antibody with a pharmaceutically acceptable buffer.

5. The method of claim 3 further comprising combining the purified antibody with a pharmaceutical carrier.

6. The host cell of claim 1, wherein the host cell comprises an expression vector or separate expression vectors comprising the nucleic acid sequences encoding the light chain and the heavy chain.

7. The host cell of claim 1, wherein the host cell comprises an expression plasmid or separate expression plasmids comprising the nucleic acid sequences encoding the light chain and the heavy chain.

8. The host cell of claim 1 which is a mammalian cell.

9. The host cell of claim 1 which is a Chinese Hamster Ovary (CHO) cell.

10. The host cell of claim 1 which is an SP2/0 cell.

* * * * *

UNITED STATES PATENT AND TRADEMARK OFFICE
CERTIFICATE OF CORRECTION

PATENT NO.        : 7,381,560 B2
APPLICATION NO.   : 09/911692
DATED             : June 3, 2008
INVENTOR(S)       : D. R. Anderson et al.

It is certified that error appears in the above-identified patent and that said Letters Patent is hereby corrected as shown below:

Strike the entire sequence listing (col. 31/32, line 15, through col. 53/54, line 10) and replace it with the following

```
--                        SEQUENCE LISTING

<160>  NUMBER OF SEQ ID NOS: 11

<210>  SEQ ID NO 1
     <211>  LENGTH: 8540
     <212>  TYPE: DNA
     <213>  ORGANISM: Artificial Sequence <220>  FEATURE:
     <223>  OTHER INFORMATION: vector <220>  FEATURE:
     <223>  OTHER INFORMATION: sense orientation <400>  SEQUENCE: 1
     gacgtcgcgg ccgctctagg cctccaaaaa agcctcctca ctacttctgg aatagctcag        60
     aggccgaggc ggcctcggcc tctgcataaa taaaaaaaat tagtcagcca tgcatggggc       120
     ggagaatggg cggaactggg cggagttagg ggcgggatgg gcggagttag gggcgggact       180
     atggttgctg actaattgag atgcatgctt tgcatacttc tgcctgctgg ggagcctggg       240
     gactttccac acctggttgc tgactaattg agatgcatgc tttgcatact tctgcctgct       300
```

UNITED STATES PATENT AND TRADEMARK OFFICE
CERTIFICATE OF CORRECTION

PATENT NO.       : 7,381,560 B2
APPLICATION NO.  : 09/911692
DATED            : June 3, 2008
INVENTOR(S)      : D. R. Anderson et al.

It is certified that error appears in the above-identified patent and that said Letters Patent is hereby corrected as shown below:

```
ggggagcctg gggactttcc acaccctaac tgacacacat tccacagaat taattcccct   360
agttattaat agtaatcaat tacggggtca ttagttcata gcccatatat ggagttccgc   420
gttacataac ttacggtaaa tggcccgcct ggctgaccgc ccaacgaccc ccgcccattg   480
acgtcaataa tgacgtatgt tcccatagta acgccaatag ggactttcca ttgacgtcaa   540
tgggtggact atttacggta aactgcccac ttggcagtac atcaagtgta tcatatgcca   600
agtacgcccc ctattgacgt caatgacggt aaatggcccg cctggcatta tgcccagtac   660
atgaccttat gggactttcc tacttggcag tacatctacg tattagtcat cgctattacc   720
atggtgatgc ggttttggca gtacatcaat gggcgtggat agcggtttga ctcacgggga   780
tttccaagtc tccaccccat tgacgtcaat gggagtttgt tttggcacca aaatcaacgg   840
gactttccaa aatgtcgtaa caactccgcc ccattgacgc aaatgggcgg taggcgtgta   900
cggtgggagg tctatataag cagagctggg tacgtgaacc gtcagatcgc ctggagacgc   960
catcacagat ctctcaccat gagggtcccc gctcagctcc tggggctcct gctgctctgg  1020
ctccaggtg cacgatgtga tggtaccaag gtggaaatca acgtacggt ggctgcacca  1080
tctgtcttca tcttcccgcc atctgatgag cagttgaaat ctggaactgc ctctgttgtg  1140
tgcctgctga ataacttcta tcccagagag gccaaagtac agtggaaggt ggataacgcc  1200
ctccaatcgg gtaactccca ggagagtgtc acagagcagg acagcaagga cagcacctac  1260
agcctcagca gcaccctgac gctgagcaaa gcagactacg agaaacacaa agtctacgcc  1320
tgcgaagtca cccatcaggg cctgagctcg cccgtcacaa agagcttcaa cagggagag  1380
tgttgaattc agatccgtta acggttacca actacctaga ctggattcgt gacaacatgc  1440
ggccgtgata tctacgtatg atcagcctcg actgtgcctt ctagttgcca gccatctgtt  1500
gtttgcccct ccccgtgcc ttccttgacc ctggaaggtg ccactccac tgtcctttcc  1560
taataaaatg aggaaattgc atcgcattgt ctgagtaggt gtcattctat tctgggggt  1620
ggggtggggc aggacagcaa gggggaggat tggaagaca atagcaggca tgctggggat  1680
gcggtgggct ctatggaacc agctggggct cgacagctat gccaagtacg cccctattg  1740
acgtcaatga cggtaaatgg cccgcctggc attatgccca gtacatgacc ttatgggact  1800
ttcctacttg gcagtacatc tacgtattag tcatcgctat taccatggtg atgcggtttt  1860
```

Page 2 of 24

UNITED STATES PATENT AND TRADEMARK OFFICE
CERTIFICATE OF CORRECTION

PATENT NO.      : 7,381,560 B2
APPLICATION NO. : 09/911692
DATED           : June 3, 2008
INVENTOR(S)     : D. R. Anderson et al.

It is certified that error appears in the above-identified patent and that said Letters Patent is hereby corrected as shown below:

```
ggcagtacat caatgggcgt ggatagcggt ttgactcacg gggatttcca agtctccacc 1920
ccattgacgt caatgggagt ttgttttggc accaaaatca acgggacttt ccaaaatgtc 1980
gtaacaactc cgccccattg acgcaaatgg gcggtaggcg tgtacggtgg gaggtctata 2040
taagcagagc tgggtacgtc ctcacattca gtgatcagca ctgaacacag acccgtcgac 2100
atgggttgga gcctcatctt gctcttcctt gtcgctgttg ctacgcgtgt cgctagcacc 2160
aagggcccat cggtcttccc cctggcaccc tcctccaaga gcacctctgg gggcacagcg 2220
gccctgggct gcctggtcaa ggactacttc cccgaaccgg tgacggtgtc gtggaactca 2280
ggcgccctga ccagcggcgt gcacaccttc ccggctgtcc tacagtcctc aggactctac 2340
tccctcagca gcgtggtgac cgtgccctcc agcagcttgg gcacccagac ctacatctgc 2400
aacgtgaatc acaagcccag caacaccaag gtggacaaga agcagagcc caaatcttgt 2460
gacaaaactc acacatgccc accgtgccca gcacctgaac tcctgggggg accgtcagtc 2520
ttcctcttcc ccccaaaacc caaggacacc ctcatgatct cccggacccc tgaggtcaca 2580
tgcgtggtgg tggacgtgag ccacgaagac cctgaggtca agttcaactg gtacgtggac 2640
ggcgtggagg tgcataatgc caagacaaag ccgcgggagg agcagtacaa cagcacgtac 2700
cgtgtggtca gcgtcctcac cgtcctgcac caggactggc tgaatggcaa ggactacaag 2760
tgcaaggtct ccaacaaagc cctcccagcc cccatcgaga aaaccatctc caaagccaaa 2820
gggcagcccc gagaaccaca ggtgtacacc ctgcccccat cccgggatga gctgaccagg 2880
aaccaggtca gcctgacctg cctggtcaaa ggcttctatc ccagcgacat cgccgtggag 2940
tgggagagca atgggcagcc ggagaacaac tacaagacca cgcctcccgt gctggactcc 3000
gacggctcct tcttcctcta cagcaagctc accgtggaca agagcaggtg gcagcagggg 3060
aacgtcttct catgctccgt gatgcatgag gctctgcaca accactacac gcagaagagc 3120
ctctccctgt ctccgggtaa atgaggatcc gttaacggtt accaactacc tagactggat 3180
tcgtgacaac atgcggccgt gatatctacg tatgatcagc ctcgactgtg ccttctagtt 3240
gccagccatc tgttgtttgc cctccccccg tgccttcctt gaccctggaa ggtgccactc 3300
ccactgtcct ttcctaataa aatgaggaaa ttgcatcgca ttgtctgagt aggtgtcatt 3360
ctattctggg gggtggggtg gggcaggaca gcaagggga ggattgggaa gacaatagca 3420
```

UNITED STATES PATENT AND TRADEMARK OFFICE
CERTIFICATE OF CORRECTION

PATENT NO. : 7,381,560 B2
APPLICATION NO. : 09/911692
DATED : June 3, 2008
INVENTOR(S) : D. R. Anderson et al.

It is certified that error appears in the above-identified patent and that said Letters Patent is hereby corrected as shown below:

```
ggcatgctgg ggatgcggtg ggctctatgg aaccagctgg ggctcgacag cgctggatct   3480
cccgatcccc agctttgctt ctcaatttct tatttgcata atgagaaaaa aaggaaaatt   3540
aattttaaca ccaattcagt agttgattga gcaaatgcgt tgccaaaaag gatgctttag   3600
agacagtgtt ctctgcacag ataaggacaa acattattca gagggagtac ccagagctga   3660
gactcctaag ccagtgagtg gcacagcatt ctagggagaa atatgcttgt catcaccgaa   3720
gcctgattcc gtagagccac accttggtaa gggccaatct gctcacacag gatagagagg   3780
gcaggagcca gggcagagca tataaggtga ggtaggatca gttgctcctc acatttgctt   3840
ctgacatagt tgtgttggga gcttggatag cttggacagc tcagggctgc gatttcgcgc   3900
caaacttgac ggcaatccta gcgtgaaggc tggtaggatt ttatccccgc tgccatcatg   3960
gttcgaccat tgaactgcat cgtcgccgtg tccaaaata tggggattgg caagaacgga   4020
gacctaccct ggcctccgct caggaacgag ttcaagtact tccaaagaat gaccacaacc   4080
tcttcagtgg aaggtaaaca gaatctggtg attatgggta ggaaaacctg gttctccatt   4140
cctgagaaca atcgaccttt aaaggacaga attaatatag ttctcagtag agaactcaaa   4200
gaaccaccac gaggagctca ttttcttgcc aaaagtttgg atgatgcctt aagacttatt   4260
gaacaaccgg aattggcaag taaagtagac atggtttgga tagtcggagg cagttctgtt   4320
taccaggaag ccatgaatca accaggccac cttagactct ttgtgacaag gatcatgcag   4380
gaatttgaaa gtgacacgtt tttcccagaa attgatttgg ggaaatataa acttctccca   4440
gaatacccag gcgtcctctc tgaggtccag gaggaaaaag gcatcaagta taagtttgaa   4500
gtctacgaga agaaagacta acaggaagat gctttcaagt tctctgctcc cctcctaaag   4560
tcatgcattt ttataagacc atgggacttt tgctggcttt agatcagcct cgactgtgcc   4620
ttctagttgc cagccatctg ttgtttgccc ctccccgtg ccttccttga ccctggaagg   4680
tgccactccc actgtccttt cctaataaaa tgaggaaatt gcatcgcatt gtctgagtag   4740
gtgtcattct attctggggg gtggggtggg gcaggacagc aaggggagg attgggaaga   4800
caatagcagg catgctgggg atgcggtggg ctctatggaa ccagctgggg ctcgagctac   4860
tagctttgct tctcaatttc ttatttgcat aatgagaaaa aaaggaaaat taattttaac   4920
accaattcag tagttgattg agcaaatgcg ttgccaaaaa ggatgcttta gagacagtgt   4980
```

UNITED STATES PATENT AND TRADEMARK OFFICE
CERTIFICATE OF CORRECTION

PATENT NO. : 7,381,560 B2  Page 5 of 24
APPLICATION NO. : 09/911692
DATED : June 3, 2008
INVENTOR(S) : D. R. Anderson et al.

It is certified that error appears in the above-identified patent and that said Letters Patent is hereby corrected as shown below:

```
tctctgcaca gataaggaca aacattattc agagggagta cccagagctg agactcctaa 5040
gccagtgagt ggcacagcat tctagggaga aatatgcttg tcatcaccga agcctgattc 5100
cgtagagcca caccttggta agggccaatc tgctcacaca ggatagagag ggcaggagcc 5160
agggcagagc atataaggtg aggtaggatc agttgctcct cacatttgct tctgacatag 5220
ttgtgttggg agcttggatc gatcctctat ggttgaacaa gatggattgc acgcaggttc 5280
tccggccgct tgggtggaga ggctattcgg ctatgactgg gcacaacaga caatcggctg 5340
ctctgatgcc gccgtgttcc ggctgtcagc gcaggggcgc ccggttcttt ttgtcaagac 5400
cgacctgtcc ggtgccctga atgaactgca ggacgaggca gcgcggctat cgtggctggc 5460
cacgacgggc gttccttgcg cagctgtgct cgacgttgtc actgaagcgg aagggactg  5520
gctgctattg ggcgaagtgc cggggcagga tctcctgtca tctcaccttg ctcctgccga 5580
gaaagtatcc atcatggctg atgcaatgcg gcggctgcat acgcttgatc cggctacctg 5640
cccattcgac caccaagcga aacatcgcat cgagcgagca cgtactcgga tggaagccgg 5700
tcttgtcgat caggatgatc tggacgaaga gcatcagggg ctcgcgccag ccgaactgtt 5760
cgccaggctc aaggcgcgca tgcccgacgg cgaggatctc gtcgtgaccc atggcgatgc 5820
ctgcttgccg aatatcatgg tggaaaatgg ccgcttttct ggattcatcg actgtggccg 5880
gctgggtgtg gcggaccgct atcaggacat agcgttggct acccgtgata ttgctgaaga 5940
gcttggcggc gaatgggctg accgcttcct cgtgctttac ggtatcgccg ctcccgattc 6000
gcagcgcatc gccttctatc gccttcttga cgagttcttc tgagcgggac tctggggttc 6060
gaaatgaccg accaagcgac gcccaacctg ccatcacgag atttcgattc caccgccgcc 6120
ttctatgaaa ggttgggctt cggaatcgtt ttccgggacg ccggctggat gatcctccag 6180
cgcgggatc tcatgctgga gttcttcgcc cacccaact tgtttattgc agcttataat 6240
ggttacaaat aaagcaatag catcacaaat ttcacaaata aagcattttt tcactgcat  6300
tctagttgtg gtttgtccaa actcatcaat ctatcttatc atgtctggat cgcggccgcg 6360
atcccgtcga gagcttggcg taatcatggt catagctgtt tcctgtgtga aattgttatc 6420
cgctcacaat tccacacaac atacgagccg gaagcataaa gtgtaaagcc tggggtgcct 6480
aatgagtgag ctaactcaca ttaattgcgt tgcgtcact gcccgctttc cagtcgggaa 6540
```

UNITED STATES PATENT AND TRADEMARK OFFICE
CERTIFICATE OF CORRECTION

PATENT NO. : 7,381,560 B2  Page 6 of 24
APPLICATION NO. : 09/911692
DATED : June 3, 2008
INVENTOR(S) : D. R. Anderson et al.

It is certified that error appears in the above-identified patent and that said Letters Patent is hereby corrected as shown below:

```
acctgtcgtg ccagctgcat taatgaatcg gccaacgcgc ggggagaggc ggtttgcgta   6600
ttgggcgctc ttccgcttcc tcgctcactg actcgctgcg ctcggtcgtt cggctgcggc   6660
gagcggtatc agctcactca aaggcggtaa tacggttatc cacagaatca ggggataacg   6720
caggaaagaa catgtgagca aaaggccagc aaaaggccag gaaccgtaaa aaggccgcgt   6780
tgctggcgtt ttccataggc tccgccccc ctgacgagca tcacaaaaat cgacgctcaa   6840
gtcagaggtg gcgaaacccg acaggactat aaagatacca ggcgtttccc cctggaagct   6900
ccctcgtgcg ctctcctgtt ccgaccctgc cgcttaccgg atacctgtcc gcctttctcc   6960
cttcgggaag cgtggcgctt tctcaatgct cacgctgtag gtatctcagt tcggtgtagg   7020
tcgttcgctc caagctgggc tgtgtgcacg aaccccccgt tcagcccgac cgctgcgcct   7080
tatccggtaa ctatcgtctt gagtccaacc cggtaagaca cgacttatcg ccactggcag   7140
cagccactgg taacaggatt agcagagcga ggtatgtagg cggtgctaca gagttcttga   7200
agtggtggcc taactacggc tacactagaa ggacagtatt tggtatctgc gctctgctga   7260
agccagttac cttcggaaaa agagttggta gctcttgatc cggcaaacaa accaccgctg   7320
gtagcggtgg ttttttgtt tgcaagcagc agattacgcg cagaaaaaaa ggatctcaag   7380
aagatccttt gatcttttct acggggtctg acgctcagtg gaacgaaaac tcacgttaag   7440
ggattttggt catgagatta tcaaaaagga tcttcaccta gatccttta aattaaaaat   7500
gaagttttaa atcaatctaa agtatatatg agtaaacttg gtctgacagt taccaatgct   7560
taatcagtga ggcacctatc tcagcgatct gtctatttcg ttcatccata gttgcctgac   7620
tccccgtcgt gtagataact acgatacggg agggcttacc atctggcccc agtgctgcaa   7680
tgataccgcg agacccacgc tcaccggctc cagatttatc agcaataaac cagccagccg   7740
gaagggccga gcgcagaagt ggtcctgcaa ctttatccgc ctccatccag tctattaatt   7800
gttgccggga agctagagta agtagttcgc cagttaatag tttgcgcaac gttgttgcca   7860
ttgctacagg catcgtggtg tcacgctcgt cgtttggtat ggcttcattc agctccggtt   7920
cccaacgatc aaggcgagtt acatgatccc ccatgttgtg caaaaaagcg gttagctcct   7980
tcggtcctcc gatcgttgtc agaagtaagt tggccgcagt gttatcactc atggttatgg   8040
cagcactgca taattctctt actgtcatgc catccgtaag atgcttttct gtgactggtg   8100
```

UNITED STATES PATENT AND TRADEMARK OFFICE
CERTIFICATE OF CORRECTION

| | | |
|---|---|---|
| PATENT NO. | : 7,381,560 B2 | |
| APPLICATION NO. | : 09/911692 | |
| DATED | : June 3, 2008 | |
| INVENTOR(S) | : D. R. Anderson et al. | |

It is certified that error appears in the above-identified patent and that said Letters Patent is hereby corrected as shown below:

```
agtactcaac caagtcattc tgagaatagt gtatgcggcg accgagttgc tcttgcccgg   8160
cgtcaatacg ggataatacc gcgccacata gcagaacttt aaaagtgctc atcattggaa   8220
aacgttcttc ggggcgaaaa ctctcaagga tcttaccgct gttgagatcc agttcgatgt   8280
aacccactcg tgcacccaac tgatcttcag catctttac tttcaccagc gtttctgggt    8340
gagcaaaaac aggaaggcaa aatgccgcaa aaagggaat aagggcgaca cggaaatgtt    8400
gaatactcat actcttcctt tttcaatatt attgaagcat ttatcagggt tattgtctca   8460
tgagcggata catatttgaa tgtatttaga aaataaaca aatagggtt ccgcgcacat     8520
ttccccgaaa agtgccacct                                               8540
```

UNITED STATES PATENT AND TRADEMARK OFFICE
CERTIFICATE OF CORRECTION

PATENT NO.      : 7,381,560 B2
APPLICATION NO. : 09/911692
DATED           : June 3, 2008
INVENTOR(S)     : D. R. Anderson et al.

It is certified that error appears in the above-identified patent and that said Letters Patent is hereby corrected as shown below:

```
<210>  SEQ ID NO 2
<211>  LENGTH: 9209
<212>  TYPE: DNA
<213>  ORGANISM: Artificial Sequence <220>  FEATURE:
<223>  OTHER INFORMATION: vector with chimeric antibody sequence <220>  FEATURE:
<223>  OTHER INFORMATION: sense orientation <400>  SEQUENCE: 2
gacgtcgcgg ccgctctagg cctccaaaaa agcctcctca ctacttctgg aatagctcag     60
aggccgaggc ggcctcggcc tctgcataaa taaaaaaaat tagtcagcca tgcatggggc    120
ggagaatggg cggaactggg cggagttagg ggcgggatgg gcggagttag gggcgggact    180
atggttgctg actaattgag atgcatgctt tgcatacttc tgcctgctgg ggagcctggg    240
gactttccac acctggttgc tgactaattg agatgcatgc tttgcatact tctgcctgct    300
ggggagcctg gggactttcc acaccctaac tgacacacat ccacagaat taattcccct    360
agttattaat agtaatcaat tacggggtca ttagttcata gcccatatat ggagttccgc    420
gttacataac ttacggtaaa tggcccgcct ggctgaccgc ccaacgaccc ccgcccattg    480
acgtcaataa tgacgtatgt tcccatagta acgccaatag ggactttcca ttgacgtcaa    540
tgggtggact atttacggta aactgcccac ttggcagtac atcaagtgta tcatatgcca    600
agtacgcccc ctattgacgt caatgacggt aaatggcccg cctggcatta tgcccagtac    660
atgaccttat gggactttcc tacttggcag tacatctacg tattagtcat cgctattacc    720
atggtgatgc ggttttggca gtacatcaat gggcgtggat accggtttga ctcacgcgga    780
tttccaagtc tccaccccat tgacgtcaat gggagtttgt tttggcacca aaatcaacgg    840
```

UNITED STATES PATENT AND TRADEMARK OFFICE
CERTIFICATE OF CORRECTION

PATENT NO.       : 7,381,560 B2
APPLICATION NO.  : 09/911692
DATED            : June 3, 2008
INVENTOR(S)      : D. R. Anderson et al.

It is certified that error appears in the above-identified patent and that said Letters Patent is hereby corrected as shown below:

```
gactttccaa aatgtcgtaa caactccgcc ccattgacgc aaatgggcgg taggcgtgta    900
cggtgggagg tctatataag cagagctggg tacgtgaacc gtcagatcgc ctggagacgc    960
catcacagat ctctcactat ggattttcag gtgcagatta tcagcttcct gctaatcagt   1020
gcttcagtca taatgtccag aggacaaatt gttctctccc agtctccagc aatcctgtct   1080
gcatctccag gggagaaggt cacaatgact tgcagggcca gctcaagtgt aagttacatc   1140
cactggttcc agcagaagcc aggatcctcc cccaaaccct ggatttatgc cacatccaac   1200
ctggcttctg gagtccctgt tcgcttcagt ggcagtgggt ctgggacttc ttactctctc   1260
acaatcagca gagtggaggc tgaagatgct gccacttatt actgccagca gtggactagt   1320
aacccaccca cgttcggagg ggggaccaag ctggaaatca aacgtacggt ggctgcacca   1380
tctgtcttca tcttcccgcc atctgatgag cagttgaaat ctggaactgc ctctgttgtg   1440
tgcctgctga ataacttcta tcccagagag gccaaagtac agtggaaggt ggataacgcc   1500
ctccaatcgg gtaactccca ggagagtgtc acagagcagg acagcaagga cagcacctac   1560
agcctcagca gcaccctgac gctgagcaaa gcagactacg agaaacacaa agtctacgcc   1620
tgcgaagtca cccatcaggg cctgagctcg cccgtcacaa agagcttcaa caggggagag   1680
tgttgaattc agatccgtta acggttacca actacctaga ctggattcgt gacaacatgc   1740
ggccgtgata tctacgtatg atcagcctcg actgtgcctt ctagttgcca gccatctgtt   1800
gtttgcccct ccccgtgcc ttccttgacc ctggaaggtg ccactccac  tgtcctttcc    1860
taataaaatg aggaaattgc atcgcattgt ctgagtaggt gtcattctat tctgggggt    1920
ggggtgggc aggacagcaa ggggaggat tgggaagaca atagcaggca tgctgggat      1980
gcggtgggct ctatggaacc agctggggct cgacagctat gccaagtacg cccctattg    2040
acgtcaatga cggtaaatgg cccgcctggc attatgccca gtacatgacc ttatgggact   2100
ttcctacttg gcagtacatc tacgtattag tcatcgctat taccatggtg atgcggtttt   2160
ggcagtacat caatgggcgt ggatagcggt ttgactcacg gggatttcca agtctccacc   2220
ccattgacgt caatgggagt ttgttttggc accaaaatca acgggacttt ccaaaatgtc   2280
gtaacaactc cgccccattg acgcaaatgg cggtaggcg tgtacggtgg gaggtctata    2340
taagcagagc tgggtacgtc ctcacattca gtgatcagca ctgaacacag acccgtcgac   2400
```

UNITED STATES PATENT AND TRADEMARK OFFICE
CERTIFICATE OF CORRECTION

PATENT NO. : 7,381,560 B2
APPLICATION NO. : 09/911692
DATED : June 3, 2008
INVENTOR(S) : D. R. Anderson et al.

It is certified that error appears in the above-identified patent and that said Letters Patent is hereby corrected as shown below:

```
atgggttgga gcctcatctt gctcttcctt gtcgctgttg ctacgcgtgt cctgtcccag 2460
gtacaactgc agcagcctgg ggctgagctg gtgaagcctg gggcctcagt gaagatgtcc 2520
tgcaaggctt ctggctacac atttaccagt tacaatatgc actgggtaaa acagacacct 2580
ggtcggggcc tggaatggat tggagctatt tatcccggaa atggtgatac ttcctacaat 2640
cagaagttca aggcaaggc cacattgact gcagacaaat cctccagcac agcctacatg 2700
cagctcagca gcctgacatc tgaggactct gcggtctatt actgtgcaag atcgacttac 2760
tacggcggtg actggtactt caatgtctgg ggcgcaggga ccacggtcac cgtctctgca 2820
gctagcacca agggcccatc ggtcttcccc ctggcaccct cctccaagag cacctctggg 2880
ggcacagcgg ccctgggctg cctggtcaag gactacttcc ccgaaccggt gacggtgtcg 2940
tggaactcag gcgccctgac cagcggcgtg cacaccttcc cggctgtcct acagtcctca 3000
ggactctact ccctcagcag cgtggtgacc gtgccctcca gcagcttggg cacccagacc 3060
tacatctgca acgtgaatca caagcccagc aacaccaagg tggacaagaa agcagagccc 3120
aaatcttgtg acaaaactca cacatgccca ccgtgcccag cacctgaact cctgggggga 3180
ccgtcagtct tcctcttccc cccaaaaccc aaggacaccc tcatgatctc ccggacccct 3240
gaggtcacat gcgtggtggt ggacgtgagc cacgaagacc ctgaggtcaa gttcaactgg 3300
tacgtggacg gcgtggaggt gcataatgcc aagacaaagc cgcgggagga gcagtacaac 3360
agcacgtacc gtgtggtcag cgtcctcacc gtcctgcacc aggactggct gaatggcaag 3420
gagtacaagt gcaaggtctc caacaaagcc ctcccagccc ccatcgagaa aaccatctcc 3480
aaagccaaag gcagccccg agaaccacag gtgtacaccc tgcccccatc ccgggatgag 3540
ctgaccaaga accaggtcag cctgacctgc ctggtcaaag gcttctatcc cagcgacatc 3600
gccgtggagt gggagagcaa tgggcagccg gagaacaact acaagaccac gcctcccgtg 3660
ctggactccg acggctcctt cttcctctac agcaagctca ccgtggacaa gagcaggtgg 3720
cagcagggga acgtcttctc atgctccgtg atgcatgagg ctctgcacaa ccactacacg 3780
cagaagagcc tctccctgtc tccgggtaaa tgaggatccg ttaacggtta ccaactacct 3840
agactggatt cgtgacaaca tgcggccgtg atatctacgt atgatcagcc tcgactgtgc 3900
cttctagttg ccagccatct gttgtttgcc cctccccgt gccttccttg accctggaag 3960
```

UNITED STATES PATENT AND TRADEMARK OFFICE
CERTIFICATE OF CORRECTION

PATENT NO.       : 7,381,560 B2
APPLICATION NO.  : 09/911692
DATED            : June 3, 2008
INVENTOR(S)      : D. R. Anderson et al.

It is certified that error appears in the above-identified patent and that said Letters Patent is hereby corrected as shown below:

```
gtgccactcc cactgtcctt tcctaataaa atgaggaaat tgcatcgcat tgtctgagta 4020
ggtgtcattc tattctgggg ggtggggtgg ggcaggacag caaggggag gattgggaag 4080
acaatagcag gcatgctggg gatgcggtgg gctctatgga accagctggg gctcgacagc 4140
gctggatctc ccgatcccca gctttgcttc tcaatttctt atttgcataa tgagaaaaaa 4200
aggaaaatta atttttaacac caattcagta gttgattgag caaatgcgtt gccaaaaagg 4260
atgctttaga gacagtgttc tctgcacaga taaggacaaa cattattcag agggagtacc 4320
cagagctgag actcctaagc cagtgagtgg cacagcattc tagggagaaa tatgcttgtc 4380
atcaccgaag cctgattccg tagagccaca ccttggtaag ggccaatctg ctcacacagg 4440
atagagaggg caggagccag ggcagagcat ataaggtgag gtaggatcag ttgctcctca 4500
catttgcttc tgacatagtt gtgttgggag cttggatagc ttggacagct cagggctgcg 4560
atttcgcgcc aaacttgacg gcaatcctag cgtgaaggct ggtaggattt tatcccgct 4620
gccatcatgg ttcgaccatt gaactgcatc gtcgccgtgt cccaaaatat ggggattggc 4680
aagaacggag acctaccctg gcctccgctc aggaacgagt tcaagtactt ccaaagaatg 4740
accacaacct cttcagtgga aggtaaacag aatctggtga ttatgggtag gaaaacctgg 4800
ttctccattc ctgagaagaa tcgacctta aaggacagaa ttaatatagt tctcagtaga 4860
gaactcaaag aaccaccacg aggagctcat tttcttgcca aaagtttgga tgatgcctta 4920
agacttattg aacaaccgga attggcaagt aaagtagaca tggtttggat agtcggaggc 4980
agttctgttt accaggaagc catgaatcaa ccaggccacc ttagactctt tgtgacaagg 5040
atcatgcagg aatttgaaag tgacacgttt ttcccagaaa ttgatttggg gaaatataaa 5100
cttctcccag aatacccagg cgtcctctct gaggtccagg aggaaaaagg catcaagtat 5160
aagtttgaag tctacgagaa gaaagactaa caggaagatg ctttcaagtt ctctgctccc 5220
ctcctaaagc tatgcatttt tataagacca tgggactttt gctggcttta gatcagcctc 5280
gactgtgcct tctagttgcc agccatctgt tgtttgcccc tccccgtgc cttccttgac 5340
cctggaaggt gccactccca ctgtcctttc ctaataaaat gaggaaattg catcgcattg 5400
tctgagtagg tgtcattcta ttctggggg tggggtgggg caggacagca aggggagga 5460
ttgggaagac aatagcaggc atgctgggga tgcggtgggc tctatggaac cagctgggc 5520
```

Page 11 of 24

UNITED STATES PATENT AND TRADEMARK OFFICE
CERTIFICATE OF CORRECTION

PATENT NO. : 7,381,560 B2
APPLICATION NO. : 09/911692
DATED : June 3, 2008
INVENTOR(S) : D. R. Anderson et al.

It is certified that error appears in the above-identified patent and that said Letters Patent is hereby corrected as shown below:

```
tcgagctact agctttgctt ctcaatttct tatttgcata atgagaaaaa aaggaaaatt    5580
aattttaaca ccaattcagt agttgattga gcaaatgcgt tgccaaaaag gatgctttag    5640
agacagtgtt ctctgcacag ataaggacaa acattattca gagggagtac ccagagctga    5700
gactcctaag ccagtgagtg gcacagcatt ctagggagaa atatgcttgt catcaccgaa    5760
gcctgattcc gtagagccac accttggtaa gggccaatct gctcacacag gatagagagg    5820
gcaggagcca gggcagagca tataaggtga ggtaggatca gttgctcctc acatttgctt    5880
ctgacatagt tgtgttggga gcttggatcg atcctctatg gttgaacaag atggattgca    5940
cgcaggttct ccggccgctt gggtggagag gctattcggc tatgactggg cacaacagac    6000
aatcggctgc tctgatgccg ccgtgttccg gctgtcagcg caggggcgcc cggttctttt    6060
tgtcaagacc gacctgtccg gtgccctgaa tgaactgcag gacgaggcag cgcggctatc    6120
gtggctggcc acgacgggcg ttccttgcgc agctgtgctc gacgttgtca ctgaagcggg    6180
aagggactgg ctgctattgg gcgaagtgcc ggggcaggat ctcctgtcat ctcaccttgc    6240
tcctgccgag aaagtatcca tcatggctga tgcaatgcgg cggctgcata cgcttgatcc    6300
ggctacctgc ccattcgacc accaagcgaa acatcgcatc gagcgagcac gtactcggat    6360
ggaagccggt cttgtcgatc aggatgatct ggacgaagag catcagggc tcgcgccagc    6420
cgaactgttc gccaggctca aggcgcgcat gcccgacggc gaggatctcg tcgtgaccca    6480
tggcgatgcc tgcttgccga atatcatggt ggaaaatggc cgcttttctg gattcatcga    6540
ctgtggccgg ctgggtgtgg cggaccgcta tcaggacata gcgttggcta cccgtgatat    6600
tgctgaagag cttggcggcg aatgggctga ccgcttcctc gtgctttacg gtatcgccgc    6660
tcccgattcg cagcgcatcg ccttctatcg ccttcttgac gagttcttct gagcgggact    6720
ctggggttcg aaatgaccga ccaagcgacg cccaacctgc catcacgaga tttcgattcc    6780
accgccgcct tctatgaaag gttggccttc ggaatcgttt tccgggacgc cggctggatg    6840
atcctccagc gcggggatct catgctggag ttcttcgccc acccaactt gtttattgca    6900
gcttataatg gttacaaata aagcaatagc atcacaaatt tcacaaataa agcattttt    6960
tcactgcatt ctagttgtgg tttgtccaaa ctcatcaatc tatcttatca tgtctggatc    7020
gcggccgcga tcccgtcgag agcttggcgt aatcatggtc atagctgttt cctgtgtgaa    7080
```

Page 12 of 24

UNITED STATES PATENT AND TRADEMARK OFFICE
CERTIFICATE OF CORRECTION

PATENT NO. : 7,381,560 B2 Page 13 of 24
APPLICATION NO. : 09/911692
DATED : June 3, 2008
INVENTOR(S) : D. R. Anderson et al.

It is certified that error appears in the above-identified patent and that said Letters Patent is hereby corrected as shown below:

```
attgttatcc gctcacaatt ccacacaaca tacgagccgg aagcataaag tgtaaagcct   7140
ggggtgccta atgagtgagc taactcacat taattgcgtt gcgctcactg cccgctttcc   7200
agtcgggaaa cctgtcgtgc cagctgcatt aatgaatcgg ccaacgcgcg gggagaggcg   7260
gtttgcgtat tgggcgctct tccgcttcct cgctcactga ctcgctgcgc tcggtcgttc   7320
ggctgcggcg agcggtatca gctcactcaa aggcggtaat acggttatcc acagaatcag   7380
gggataacgc aggaaagaac atgtgagcaa aaggccagca aaaggccagg aaccgtaaaa   7440
aggccgcgtt gctggcgttt ttccataggc tccgccccc tgacgagcat cacaaaaatc   7500
gacgctcaag tcagaggtgg cgaaacccga caggactata aagataccag gcgtttcccc   7560
ctggaagctc cctcgtgcgc tctcctgttc cgaccctgcc gcttaccgga tacctgtccg   7620
cctttctccc ttcgggaagc gtggcgcttt ctcaatgctc acgctgtagg tatctcagtt   7680
cggtgtaggt cgttcgctcc aagctgggct gtgtgcacga accccccgtt cagcccgacc   7740
gctgcgcctt atccggtaac tatcgtcttg agtccaaccc ggtaagacac gacttatcgc   7800
cactggcagc agccactggt aacaggatta gcagagcgag gtatgtaggc ggtgctacag   7860
agttcttgaa gtggtggcct aactacggct acactagaag gacagtattt ggtatctgcg   7920
ctctgctgaa gccagttacc ttcggaaaaa gagttggtag ctcttgatcc ggcaaacaaa   7980
ccaccgctgg tagcggtggt ttttttgttt gcaagcagca gattacgcgc agaaaaaaag   8040
gatctcaaga agatcctttg atcttttcta cggggtctga cgctcagtgg aacgaaaact   8100
cacgttaagg gattttggtc atgagattat caaaaaggat cttcacctag atccttttaa   8160
attaaaaatg aagttttaaa tcaatctaaa gtatatatga gtaaacttgg tctgacagtt   8220
accaatgctt aatcagtgag gcacctatct cagcgatctg tctatttcgt tcatccatag   8280
ttgcctgact ccccgtcgtg tagataacta cgatacggga gggcttacca tctggcccca   8340
gtgctgcaat gataccgcga gacccacgct caccggctcc agatttatca gcaataaacc   8400
agccagccgg aagggccgag cgcagaagtg gtcctgcaac tttatccgcc tccatccagt   8460
ctattaattg ttgccgggaa gctagagtaa gtagttcgcc agttaatagt ttgcgcaacg   8520
ttgttgccat tgctacaggc atcgtggtgt cacgctcgtc gtttggtatg gcttcattca   8580
gctccggttc ccaacgatca aggcgagtta catgatcccc catgttgtgc aaaaaagcgg   8640
```

UNITED STATES PATENT AND TRADEMARK OFFICE
CERTIFICATE OF CORRECTION

PATENT NO.       : 7,381,560 B2
APPLICATION NO.  : 09/911692
DATED            : June 3, 2008
INVENTOR(S)      : D. R. Anderson et al.

It is certified that error appears in the above-identified patent and that said Letters Patent is hereby corrected as shown below:

```
ttagctcctt cggtcctccg atcgttgtca gaagtaagtt ggccgcagtg ttatcactca   8700
tggttatggc agcactgcat aattctctta ctgtcatgcc atccgtaaga tgcttttctg   8760
tgactggtga gtactcaacc aagtcattct gagaatagtg tatgcggcga ccgagttgct   8820
cttgcccggc gtcaatacgg gataataccg cgccacatag cagaacttta aaagtgctca   8880
tcattggaaa acgttcttcg gggcgaaaac tctcaaggat cttaccgctg ttgagatcca   8940
gttcgatgta acccactcgt gcacccaact gatcttcagc atctttact ttcaccagcg   9000
tttctgggtg agcaaaaaca ggaaggcaaa atgccgcaaa aaagggaata agggcgacac   9060
ggaaatgttg aatactcata ctcttccttt ttcaatatta ttgaagcatt tatcagggtt   9120
attgtctcat gagcggatac atatttgaat gtatttagaa aaataaacaa atagggggttc   9180
cgcgcacatt tccccgaaaa gtgccacct                                      9209
```

UNITED STATES PATENT AND TRADEMARK OFFICE
CERTIFICATE OF CORRECTION

PATENT NO. : 7,381,560 B2
APPLICATION NO. : 09/911692
DATED : June 3, 2008
INVENTOR(S) : D. R. Anderson et al.

It is certified that error appears in the above-identified patent and that said Letters Patent is hereby corrected as shown below:

```
<210> SEQ ID NO 3
<211> LENGTH: 384
<212> TYPE: DNA
<213> ORGANISM: Mus musculus
<220> FEATURE:
<223> OTHER INFORMATION: sense orientation
<400> SEQUENCE: 3
atggattttc aggtgcagat tatcagcttc ctgctaatca gtgcttcagt cataatgtcc    60
agagggcaaa ttgttctctc ccagtctcca gcaatcctgt ctgcatctcc aggggagaag   120
gtcacaatga cttgcagggc cagcctgtct gcatctccag gggagaaggt cacaatgact   180
tgcagggcca gccccaaacc ctggatttat gccacatcca acctggcttc tggagtccct   240
gttcgcttca gtggcagtgg gtctgggact tcttactctc tcacaatcag cagagtggag   300
gctgaagatg ctgccactta ttactgccag cagtggacta gtaacccacc cacgttcgga   360
gggggaccaa agctggaaat caaa                                          384
```

UNITED STATES PATENT AND TRADEMARK OFFICE
CERTIFICATE OF CORRECTION

PATENT NO. : 7,381,560 B2
APPLICATION NO. : 09/911692
DATED : June 3, 2008
INVENTOR(S) : D. R. Anderson et al.

It is certified that error appears in the above-identified patent and that said Letters Patent is hereby corrected as shown below:

```
<210>  SEQ ID NO 4
<211>  LENGTH: 128
<212>  TYPE: PRT
<213>  ORGANISM: Mus musculus <400>  SEQUENCE: 4
Met Asp Phe Gln Val Gln Ile Ile Ser Phe Leu Leu Ile Ser Ala Ser
 1               5                  10                  15
Val Ile Met Ser Arg Gly Gln Ile Val Leu Ser Gln Ser Pro Ala Ile
                20                  25                  30
Leu Ser Ala Ser Pro Gly Glu Lys Val Thr Met Thr Cys Arg Ala Ser
                35                  40                  45
Ser Ser Val Ser Tyr Ile His Trp Phe Gln Gln Lys Pro Gly Ser Ser
                50                  55                  60
Pro Lys Pro Trp Ile Tyr Ala Thr Ser Asn Leu Ala Ser Gly Val Pro
65                  70                  75                  80
Val Arg Phe Ser Gly Ser Gly Ser Gly Thr Ser Tyr Ser Leu Thr Ile
                85                  90                  95
Ser Arg Val Glu Ala Glu Asp Ala Ala Thr Tyr Tyr Cys Gln Gln Trp
                100                 105                 110
Thr Ser Asn Pro Pro Thr Phe Gly Gly Gly Thr Lys Leu Glu Ile Lys
                115                 120                 125
```

UNITED STATES PATENT AND TRADEMARK OFFICE
CERTIFICATE OF CORRECTION

PATENT NO. : 7,381,560 B2
APPLICATION NO. : 09/911692
DATED : June 3, 2008
INVENTOR(S) : D. R. Anderson et al.

It is certified that error appears in the above-identified patent and that said Letters Patent is hereby corrected as shown below:

```
<210>  SEQ ID NO 5
<211>  LENGTH: 420
<212>  TYPE: DNA
<213>  ORGANISM: Mus musculus <220>  FEATURE:
<223>  OTHER INFORMATION: sense orientation <400>  SEQUENCE: 5
atgggttgga gcctcatctt gctcttcctt gtcgctgttg ctacgcgtgt cctgtcccag    60
gtacaactgc agcagcctgg ggctgagctg gtgaagcctg gggcctcagt gaagatgtcc   120
tgcaaggctt ctggctacac atttaccagt tacaatatgc actgggtaaa acagacacct   180
ggtcggggcc tggaatggat tggagctatt tatcccggaa atggtgatac ttcctacaat   240
cagaagttca aaggcaaggc cacattgact gcagacaaat cctccagcac agcctacatg   300
cagctcagca gcctgacatc tgaggactct gcggtctatt actgtgcaag atcgacttac   360
tacggcggtg actggtactt caatgtctgg ggcgcaggga ccacggtcac cgtctctgca   420
```

UNITED STATES PATENT AND TRADEMARK OFFICE
CERTIFICATE OF CORRECTION

| | | |
|---|---|---|
| PATENT NO. | : 7,381,560 B2 | Page 18 of 24 |
| APPLICATION NO. | : 09/911692 | |
| DATED | : June 3, 2008 | |
| INVENTOR(S) | : D. R. Anderson et al. | |

It is certified that error appears in the above-identified patent and that said Letters Patent is hereby corrected as shown below:

```
<210>  SEQ ID NO 6
<211>  LENGTH: 140
<212>  TYPE: PRT
<213>  ORGANISM: Mus musculus <400>  SEQUENCE: 6
Met Gly Trp Ser Leu Ile Leu Leu Phe Leu Val Ala Val Ala Thr Arg
1               5                   10                  15
Val Leu Ser Gln Val Gln Leu Gln Gln Pro Gly Ala Glu Leu Val Lys
            20                  25                  30
Pro Gly Ala Ser Val Lys Met Ser Cys Lys Ala Ser Gly Tyr Thr Phe
        35                  40                  45
Thr Ser Tyr Asn Met His Trp Val Lys Gln Thr Pro Gly Arg Gly Leu
    50                  55                  60
Glu Trp Ile Gly Ala Ile Tyr Pro Gly Asn Gly Asp Thr Ser Tyr Asn
65                  70                  75                  80
Gln Lys Phe Lys Gly Lys Ala Thr Leu Thr Ala Asp Lys Ser Ser Ser
                85                  90                  95
Thr Ala Tyr Met Gln Leu Ser Ser Leu Thr Ser Glu Asp Ser Ala Val
            100                 105                 110
Tyr Tyr Cys Ala Arg Ser Thr Tyr Tyr Gly Gly Asp Trp Tyr Phe Asn
        115                 120                 125
Val Trp Gly Ala Gly Thr Thr Val Thr Val Ser Ala
    130                 135                 140
```

UNITED STATES PATENT AND TRADEMARK OFFICE
CERTIFICATE OF CORRECTION

| | | |
|---|---|---|
| PATENT NO. | : 7,381,560 B2 | |
| APPLICATION NO. | : 09/911692 | |
| DATED | : June 3, 2008 | |
| INVENTOR(S) | : D. R. Anderson et al. | |

It is certified that error appears in the above-identified patent and that said Letters Patent is hereby corrected as shown below:

```
<210>  SEQ ID NO 7
<211>  LENGTH: 27
<212>  TYPE: DNA
<213>  ORGANISM: Artificial Sequence <220>  FEATURE:
<223>  OTHER INFORMATION: impaired Kozak sequence and restriction enzyme
site <220>  FEATURE:
<223>  OTHER INFORMATION: sense orientation <400>  SEQUENCE: 7
gggagcttgg atcgatcctc tatggtt                                       27
```

UNITED STATES PATENT AND TRADEMARK OFFICE
CERTIFICATE OF CORRECTION

| | |
|---|---|
| PATENT NO. | : 7,381,560 B2 |
| APPLICATION NO. | : 09/911692 |
| DATED | : June 3, 2008 |
| INVENTOR(S) | : D. R. Anderson et al. |

It is certified that error appears in the above-identified patent and that said Letters Patent is hereby corrected as shown below:

```
<210>  SEQ ID NO 8
<211>  LENGTH: 47
<212>  TYPE: DNA
<213>  ORGANISM: Artificial Sequence <220>  FEATURE:
<223>  OTHER INFORMATION: PCR Primer <220>  FEATURE:
<223>  OTHER INFORMATION: sense orientation <400>  SEQUENCE: 8
atcacagatc tctcaccatg gattttcagg tgcagattat cagcttc            47
```

UNITED STATES PATENT AND TRADEMARK OFFICE
CERTIFICATE OF CORRECTION

| | |
|---|---|
| PATENT NO. | : 7,381,560 B2 |
| APPLICATION NO. | : 09/911692 |
| DATED | : June 3, 2008 |
| INVENTOR(S) | : D. R. Anderson et al. |

It is certified that error appears in the above-identified patent and that said Letters Patent is hereby corrected as shown below:

```
<210>  SEQ ID NO 9
<211>  LENGTH: 30
<212>  TYPE: DNA
<213>  ORGANISM: Artificial Sequence <220>  FEATURE:
<223>  OTHER INFORMATION: PCR Primer <220>  FEATURE:
<223>  OTHER INFORMATION: antisense orientation <400>  SEQUENCE: 9
tgcagcatcc gtacgtttga tttccagctt                           30
```

UNITED STATES PATENT AND TRADEMARK OFFICE
CERTIFICATE OF CORRECTION

PATENT NO. : 7,381,560 B2
APPLICATION NO. : 09/911692
DATED : June 3, 2008
INVENTOR(S) : D. R. Anderson et al.

It is certified that error appears in the above-identified patent and that said Letters Patent is hereby corrected as shown below:

```
<210>  SEQ ID NO 10
<211>  LENGTH: 27
<212>  TYPE: DNA
<213>  ORGANISM: Artificial Sequence <220>  FEATURE:
<223>  OTHER INFORMATION: PCR Primer <220>  FEATURE:
<223>  OTHER INFORMATION: sense orientation <400>  SEQUENCE: 10
gcggctccca cgcgtgtcct gtcccag                                27
```

UNITED STATES PATENT AND TRADEMARK OFFICE
CERTIFICATE OF CORRECTION

PATENT NO. : 7,381,560 B2
APPLICATION NO. : 09/911692
DATED : June 3, 2008
INVENTOR(S) : D. R. Anderson et al.

It is certified that error appears in the above-identified patent and that said Letters Patent is hereby corrected as shown below:

```
<210>   SEQ ID NO 11
<211>   LENGTH: 29
<212>   TYPE: DNA
<213>   ORGANISM: Artificial Sequence <220>   FEATURE:
<223>   OTHER INFORMATION: PCR Primer <220>   FEATURE:
<223>   OTHER INFORMATION: antisense orientation <220>   FEATURE:
<221>   misc_feature
<222>   LOCATION: (1)..(29)
<223>   OTHER INFORMATION: s is g or c <220>   FEATURE:
<221>   misc_feature
<222>   LOCATION: (1)..(29)
<223>   OTHER INFORMATION: m is a or c <220>   FEATURE:
<221>   misc_feature
<222>   LOCATION: (1)..(29)
<223>   OTHER INFORMATION: r is g or a
```

UNITED STATES PATENT AND TRADEMARK OFFICE
CERTIFICATE OF CORRECTION

PATENT NO. : 7,381,560 B2
APPLICATION NO. : 09/911692
DATED : June 3, 2008
INVENTOR(S) : D. R. Anderson et al.

It is certified that error appears in the above-identified patent and that said Letters Patent is hereby corrected as shown below:

```
<400>  SEQUENCE: 11                                                 --
ggstgttgtg ctagctgmrg agacrgtga.                               29
```

Signed and Sealed this

Second Day of September, 2008

JON W. DUDAS
*Director of the United States Patent and Trademark Office*

UNITED STATES PATENT AND TRADEMARK OFFICE
CERTIFICATE OF CORRECTION

| | | |
|---|---|---|
| PATENT NO. | : 7,381,560 B2 | Page 1 of 1 |
| APPLICATION NO. | : 09/911692 | |
| DATED | : June 3, 2008 | |
| INVENTOR(S) | : Anderson et al. | |

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 2078 days.

Signed and Sealed this
Eighteenth Day of October, 2011

David J. Kappos
*Director of the United States Patent and Trademark Office*